United States Patent
Bell et al.

(10) Patent No.: US 11,649,482 B2
(45) Date of Patent: May 16, 2023

(54) DROPLET-BASED SINGLE CELL GENOMIC DNA SEQUENCING

(71) Applicant: PRESIDENT AND FELLOWS OF HARVARD COLLEGE, Cambridge, MA (US)

(72) Inventors: Avery Davis Bell, Cambridge, MA (US); Steven A. McCarroll, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 109 days.

(21) Appl. No.: 17/053,418

(22) PCT Filed: Apr. 26, 2019

(86) PCT No.: PCT/US2019/029427
§ 371 (c)(1),
(2) Date: Nov. 6, 2020

(87) PCT Pub. No.: WO2019/217099
PCT Pub. Date: Nov. 14, 2019

(65) Prior Publication Data
US 2021/0230667 A1   Jul. 29, 2021

Related U.S. Application Data

(60) Provisional application No. 62/668,334, filed on May 8, 2018.

(51) Int. Cl.
*C12Q 1/68* (2018.01)
*C12Q 1/6806* (2018.01)

(52) U.S. Cl.
CPC ................ *C12Q 1/6806* (2013.01)

(58) Field of Classification Search
CPC .................................. C12Q 1/6806
See application file for complete search history.

(56) References Cited

U.S. PATENT DOCUMENTS

| 5,780,230 A | * | 7/1998 | Li | .................. | C07K 14/463 435/317.1 |
| 2009/0111184 A1 | | 4/2009 | Hillis et al. | | |

(Continued)

FOREIGN PATENT DOCUMENTS

| WO | 198808728 A1 | 11/1988 | | |
| WO | WO-2012083225 A2 | * | 6/2012 | ............. C07K 16/00 |

(Continued)

OTHER PUBLICATIONS

Samocha-Bone et al., In-vitro human spermatozoa nuclear decondensation assessed by flow cytometry, 1998, Mol. Human. Rep., 4 (2), 133-7. (Year: 1998).*

(Continued)

*Primary Examiner* — Aaron A Priest
(74) *Attorney, Agent, or Firm* — Withers Bergman LLP; Christopher R. Cowles

(57) ABSTRACT

The present disclosure relates to compositions and methods for performing droplet-based high throughput sequencing upon genomic DNA of single cells (e.g., individual sperm). The instant disclosure provides a droplet that includes: i) a mammalian cell nucleus; and ii) a microbead presenting attached oligonucleotides, where the attached oligonucleotides include a nucleic acid sequence capable of hybridization and capture of genomic DNA and a microbead identification sequence that is common to all oligonucleotides attached to the microbead, where the mammalian cell nucleus is accessible to the microbead-attached oligonucle- (Continued)

otides to an extent sufficient to allow for genomic DNA capture and amplification of genomic DNA to occur within the droplet.

18 Claims, 27 Drawing Sheets

Specification includes a Sequence Listing.

(56) References Cited

U.S. PATENT DOCUMENTS

| | | | |
|---|---|---|---|
| 2015/0005199 A1* | 1/2015 | Hindson | B01J 19/0046 |
| | | | 506/16 |
| 2015/0005200 A1 | 1/2015 | Hindson et al. | |
| 2016/0370266 A1 | 12/2016 | White et al. | |

FOREIGN PATENT DOCUMENTS

| | | | | |
|---|---|---|---|---|
| WO | WO-2014144495 A1 * | 9/2014 | | C07K 16/00 |
| WO | WO-2016077750 A1 * | 5/2016 | | C12Q 1/6881 |
| WO | WO-2016123692 A1 * | 8/2016 | | B01L 3/502761 |
| WO | 2017164936 A1 | 9/2017 | | |
| WO | WO-2019157529 A1 * | 8/2019 | | C07K 14/70539 |

OTHER PUBLICATIONS

Yokota et al., Effects of Heparin on Polymerase Chain Reaction for Blood White Cells, 1999, J. Clin. Lab. Anal., 13, 133-40. (Year: 1999).*

Shirazi et al. "Male Pronuclear Formation and Embryo Development Following Intracytoplasmic Injection of Ovine Pretreated Sperm," Avicenna J Med Biotechnol, Jan. 1, 2018 (Jan. 1, 2018), vol. 10, Iss. 1, pp. 41-48. entire document.

Habib et al. "Massively parallel single-nucleus RNA-seq with DroNc-seq," Nat Methods, Aug. 28, 2017 (Aug. 28, 2017), vol. 14, pp. 955-958. entire document.

International Search Report dated Jul. 18, 2019 for related Application No. PCT/US2019/029427.

International Search Report dated Nov. 19, 2020 for related Application No. PCT/US2019/029427.

* cited by examiner

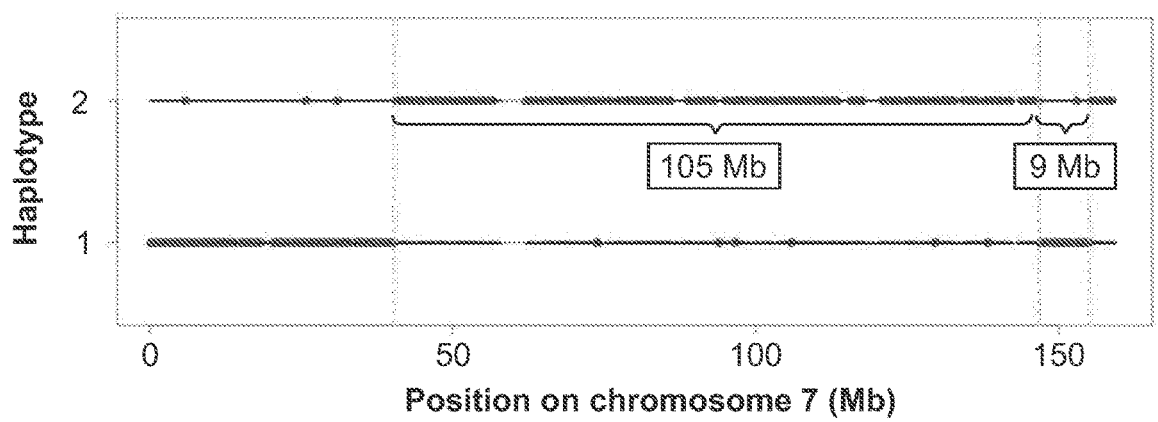
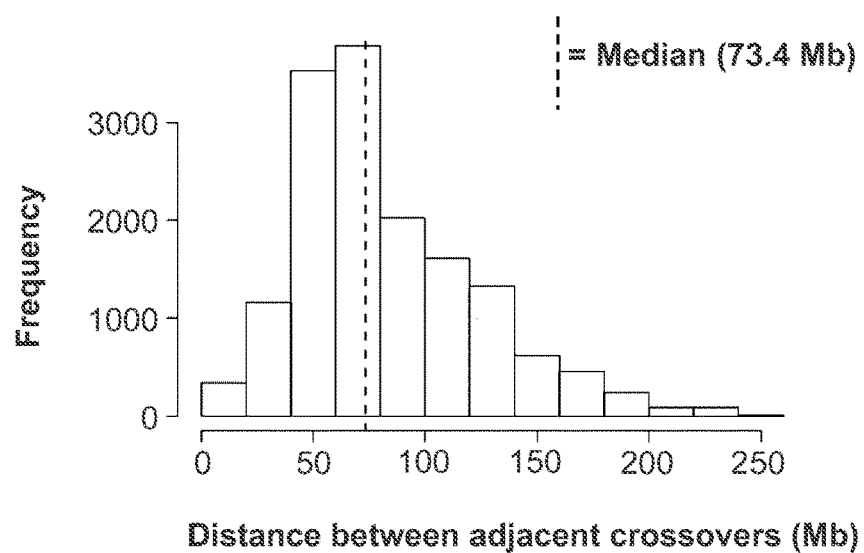
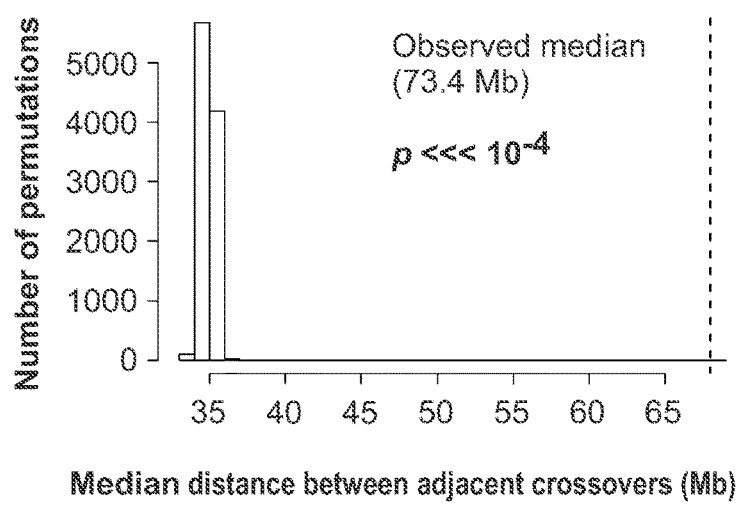
FIG. 8

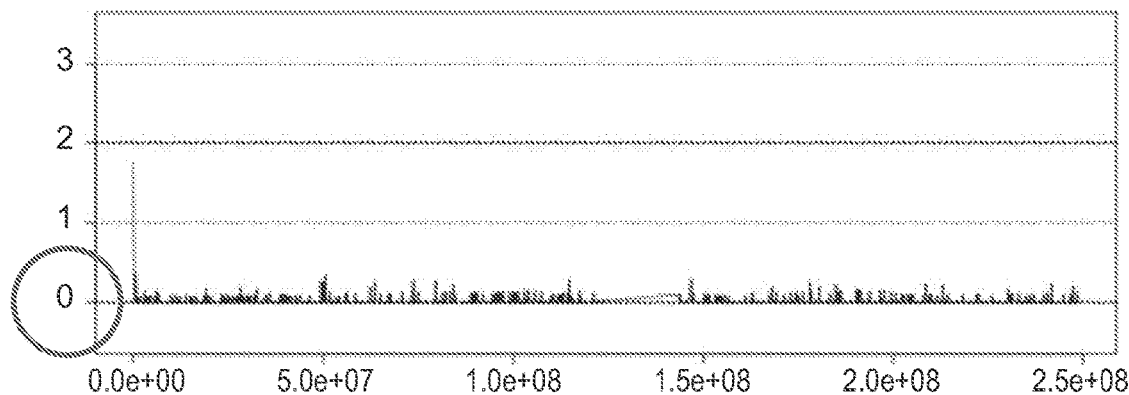
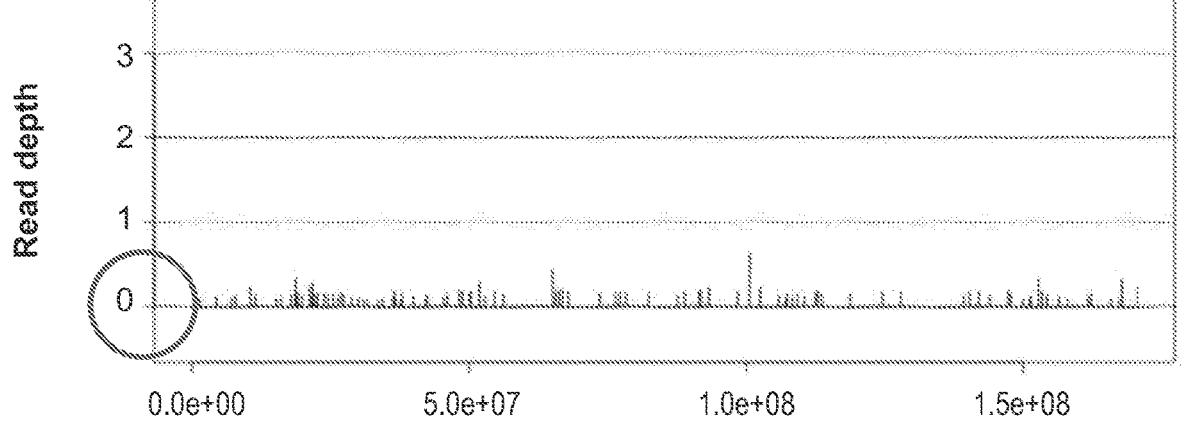
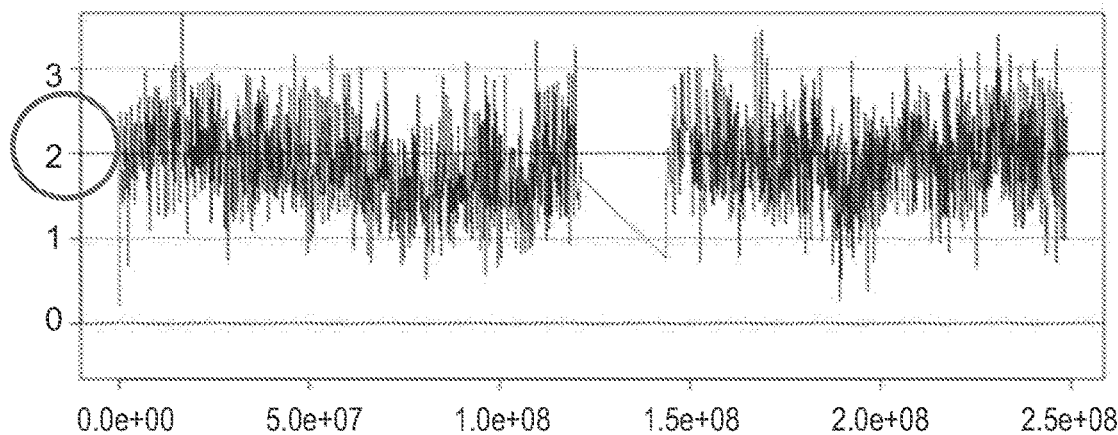
FIG. 18

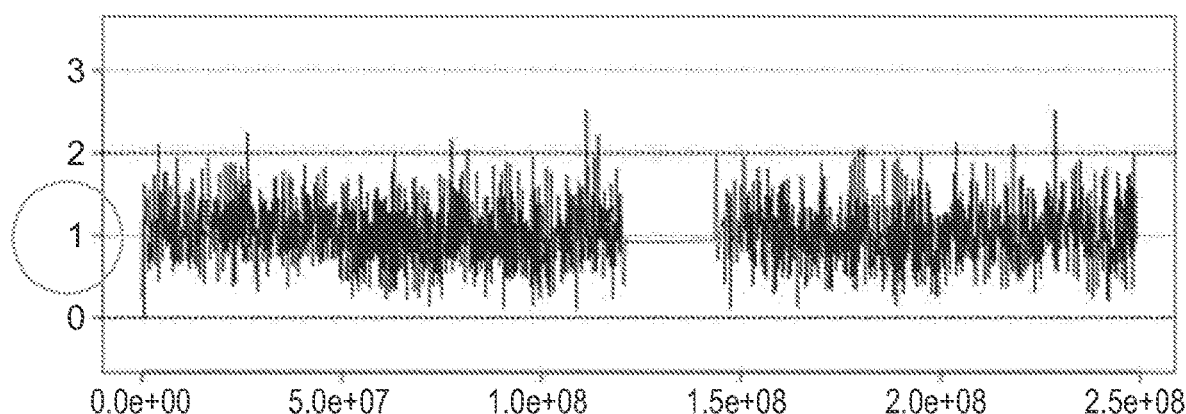
Loss of chr6
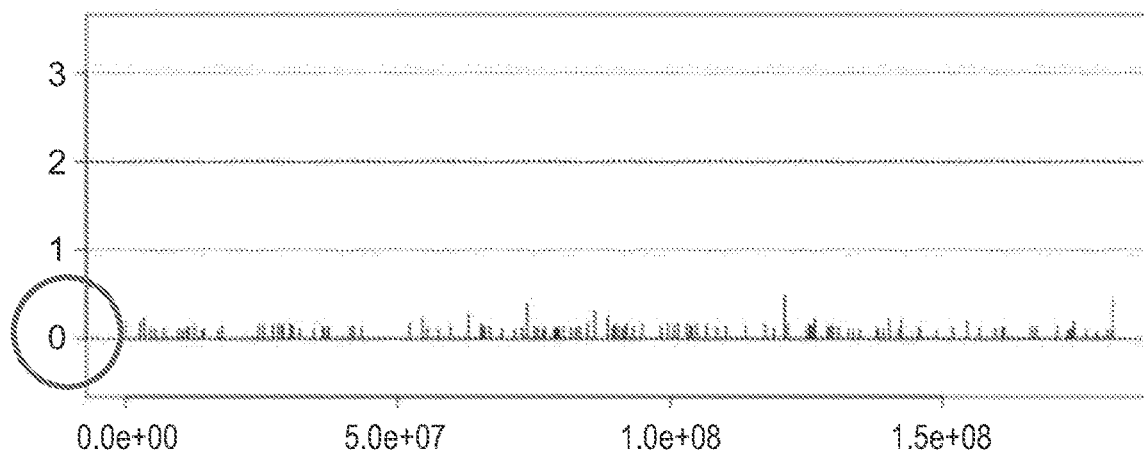
Gain of chr4
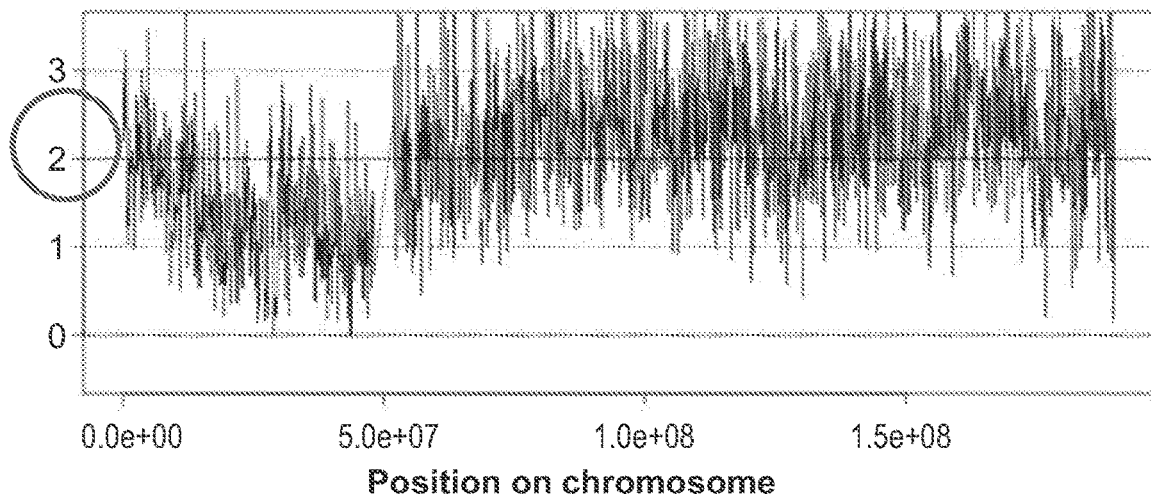
Position on chromosome
FIG. 18 (cont.)

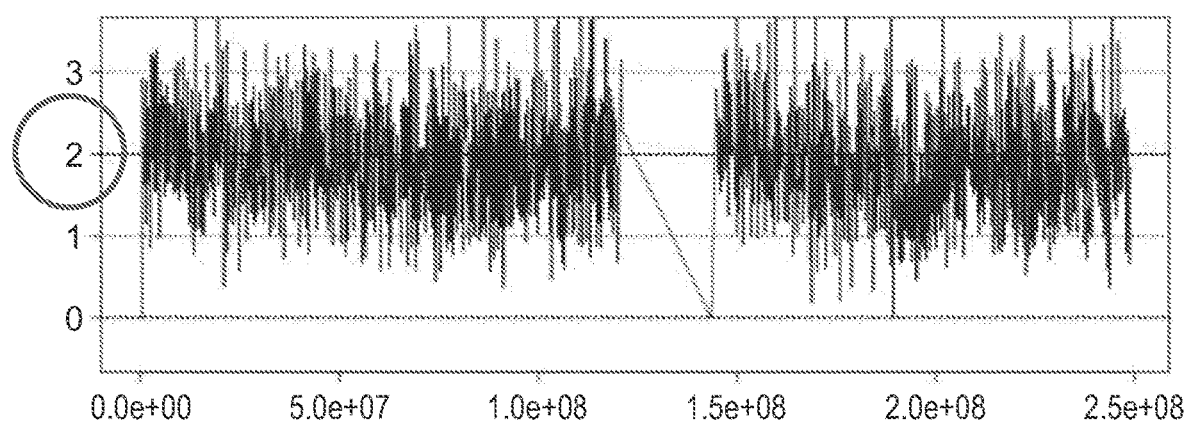
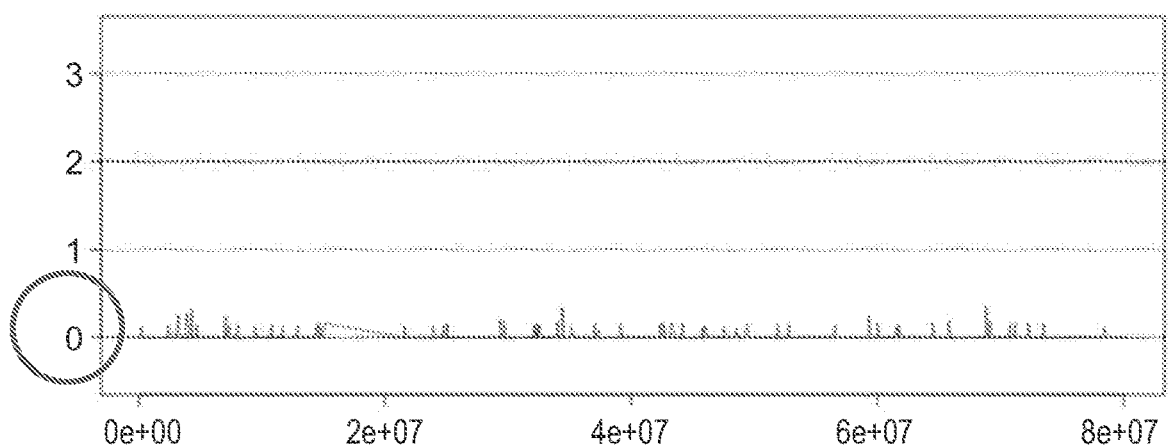
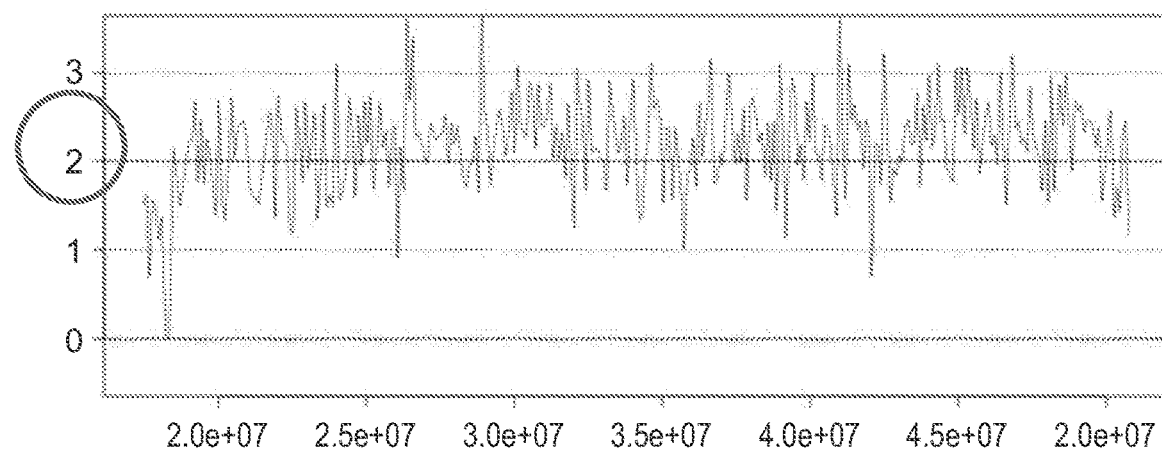
FIG. 18 (cont.)

| Donor | Cells (number excluding cell and bead doublets) | Reads per cell (median, thousands) | Genome covered per cell (median, percent) | Heterozygous SNPs in genome (millions) | Unique heterozygous SNP alleles observed per cell (median, thousands) | Crossovers observed (total, thousands) | Crossovers per cell (mean) | Resolution of crossovers (kb, median) | Autosomal aneuploidy events (percent of cells)# | Sex chromosome aneuploidy events (percent of cells)# |
|---|---|---|---|---|---|---|---|---|---|---|
| Overall | 31,228[a] | 211[b] | 1.0[c] | -- | 24.6[b] | 813[a] | 26.11[c] | 240[d] | 1.6[b] | 0.9[b] |
| NC1 | 982 | 284 | 1.4 | 1.95 | 31.6 | 26 | 26.31 | 189 | 1.5 | 0.6 |
| NC2 | 1,680 | 163 | 0.8 | 1.98 | 18.2 | 37 | 22.19 | 307 | 2.0 | 0.7 |
| NC3 | 1,289 | 190 | 0.9 | 1.94 | 21.5 | 36 | 28.13 | 260 | 1.7 | 0.7 |
| NC4 | 1,482 | 243 | 1.1 | 1.98 | 26.8 | 40 | 26.98 | 243 | 1.1 | 0.5 |
| NC6 | 1,370 | 154 | 0.8 | 2.53 | 23.8 | 38 | 27.57 | 253 | 0.7 | 0.3 |
| NC8 | 1,663 | 304 | 1.5 | 1.81 | 30.9 | 45 | 26.98 | 229 | 3.1 | 0.5 |
| NC9 | 1,894 | 245 | 1.2 | 1.79 | 25.6 | 53 | 27.98 | 231 | 0.8 | 1.5 |
| NC10 | 1,154 | 224 | 1.1 | 1.82 | 23.3 | 29 | 24.99 | 257 | 1.5 | 0.3 |
| NC11 | 1,930 | 202 | 1.0 | 1.92 | 22.8 | 50 | 25.82 | 242 | 1.3 | 0.4 |
| NC12 | 2,145 | 179 | 0.9 | 1.91 | 20.6 | 51 | 23.76 | 270 | 1.2 | 1.7 |
| NC13 | 1,514 | 259 | 1.2 | 1.92 | 28.3 | 41 | 27.19 | 202 | 0.9 | 1.0 |
| NC14 | 1,336 | 296 | 1.4 | 1.92 | 32.4 | 36 | 26.65 | 175 | 2.5 | 1.2 |
| NC15 | 1,702 | 211 | 1.0 | 1.93 | 23.2 | 42 | 24.80 | 268 | 1.0 | 0.9 |
| NC16 | 1,785 | 241 | 1.2 | 1.92 | 26.9 | 42 | 23.78 | 227 | 2.2 | 1.3 |
| NC17 | 1,504 | 220 | 1.0 | 1.94 | 23.8 | 39 | 25.92 | 250 | 2.1 | 0.7 |
| NC18 | 1,589 | 170 | 0.8 | 1.93 | 18.4 | 42 | 26.48 | 317 | 1.2 | 0.6 |
| NC22 | 1,693 | 195 | 0.9 | 2.53 | 29.7 | 44 | 25.96 | 205 | 1.4 | 0.7 |
| NC25 | 2,274 | 175 | 0.8 | 2.47 | 25.8 | 62 | 27.31 | 211 | 2.8 | 1.8 |
| NC26 | 974 | 120 | 0.6 | 2.55 | 18.0 | 26 | 26.67 | 355 | 1.3 | 0.4 |
| NC27 | 1,268 | 267 | 1.3 | 1.96 | 29.2 | 34 | 26.80 | 199 | 1.7 | 0.6 |

FIG. 20

DROPLET-BASED SINGLE CELL GENOMIC DNA SEQUENCING

CROSS-REFERENCE TO RELATED APPLICATIONS

This application is a national stage application, filed under 35 U.S.C. § 371, of International Patent Application No. PCT/US19/29427, filed Apr. 26, 2019, entitled "Droplet-Based Single Cell Genomic DNA Sequencing" and published Nov. 14, 2019 as WO 2019/217099, which claims the benefit of priority under 35 U.S.C. § 119(e) to U.S. Provisional Application No. 62/668,334, filed on May 8, 2018, entitled, "Droplet-Based Single Cell Genomic DNA Sequencing." The entire contents of these patent applications are hereby incorporated by reference herein.

STATEMENT REGARDING FEDERALLY SPONSORED RESEARCH

This invention was made with government support under Grant No. 2R01 HG006855, awarded by the National Institutes of Health. The government has certain rights in the invention.

FIELD OF THE INVENTION

The invention relates generally to methods and compositions for obtaining nucleic acid sequence from a population of cells, including gametes.

SEQUENCE LISTING

The instant application contains a Sequence Listing which has been filed electronically in ASCII format and is hereby incorporated by reference in its entirety. Said ASCII copy, created on Sep. 12, 2022, is named BN00007_0342_BI10347_SeqListing_ST25.txt and is 2 KB in size.

BACKGROUND OF THE INVENTION

Droplet-based sequencing approaches that employ microbead-attached oligonucleotides for nucleic acid capture, such as those set forth in WO 2016/040476 (PCT/US2015/049178), as well as, e.g., in WO 2018/075693, WO 2017/139690 and WO 2017/096158, have been previously used with great success to obtain single-cell RNA expression data across a population of cells. Such droplet-based approaches act in both a scalable and cost-efficient manner, as compared, e.g., to plate-based expression profiling approaches. Droplet-based sequencing methods commonly rely upon introduction of an oligonucleotide-supplied "barcode" nucleic acid to amplicons produced from captured nucleic acids (e.g., captured poly-A-tailed RNAs), where the introduced barcode aids in identification of a single bead, droplet, and/or cell from whence an individual amplified sequence derived.

While such droplet-based oligonucleotide capture and sequencing approaches have been successfully employed with regularity to obtain single-cell RNA expression data across large populations of individual cells by employing barcoding and bead-based "next-gen" sequencing techniques, such approaches have not been readily adaptable to obtainment of genomic DNA sequences from single cells across a large population. Notably, genomic DNA is densely packed, highly protein-associated (wrapped around histones, etc.) and is encapsulated within the nucleus, creating access issues for droplet- and bead-based approaches to obtain single-cell, high-throughput sequencing across a large population of cells. A need therefore exists for processes and compositions that can be used to successfully assess the genomes of thousands of individual mammalian cells at one time in a scalable and affordable manner.

BRIEF SUMMARY OF THE INVENTION

The current disclosure relates, at least in part, to discovery of an approach for droplet-based genomic DNA capture, amplification and sequencing that is capable of obtaining high-throughput single-cell sequence from individual mammalian cells, notably including sperm cells, as specifically exemplified herein. To access the advantages of cost efficiency and throughput imparted by droplet- and associated bead-based/microfluidics approaches to the processes of nucleic acid capture, amplification and next-generation sequencing, the instant disclosure specifically provides for treatment of mammalian nuclei using a method that maintains the integrity of an individual nucleus (thereby retaining the ability to sort an individual nucleus using microfluidic droplet-formation processes) while also relaxing the native condensation of the mammalian genome ("decondensing" mammalian genomic DNA) harbored within the nucleus, allowing not only for generation of single-nucleus-containing droplets but also accessibility of the genomic DNA of such nuclei to microbead-attached oligonucleotides that are co-incorporated into such droplets.

In one aspect, the instant disclosure provides a droplet that includes: i) a mammalian cell nucleus; and ii) a microbead presenting attached oligonucleotides, where the attached oligonucleotides include a nucleic acid sequence capable of hybridization and capture of genomic DNA and a microbead identification sequence that is common to all oligonucleotides attached to the microbead, where the mammalian cell nucleus is accessible to the microbead-attached oligonucleotides to an extent sufficient to allow for genomic DNA capture and amplification of genomic DNA to occur within the droplet.

In one embodiment, the mammalian cell is a sperm cell.

In certain embodiments, the mammalian cell has been rapidly freeze-thawed to provide an accessible nucleus.

Optionally, the sperm cell has been contacted with β-mercaptoethanol and heparin in an aqueous salt buffer, heated, then contacted with heparinase, thereby producing a sperm cell nucleus having genomic DNA that is accessible to the microbead-attached oligonucleotides.

In some embodiments, the microbead presenting attached oligonucleotides presents at least 100 attached oligonucleotides, where the at least 100 attached oligonucleotides include a nucleic acid sequence capable of hybridization and capture of genomic DNA and a microbead identification sequence that is common to all at least 100 oligonucleotides on the microbead.

Optionally, the microbead-attached oligonucleotides are attached to the microbead via a cleavable linker, optionally via a photocleavable linker.

In certain embodiments, the droplet is oil-encapsulated.

In one embodiment, the instant disclosure provides a droplet population that includes a plurality of droplets of the instant disclosure as described above or elsewhere herein.

In related embodiments, a majority of the droplet population is made up of droplets of the instant disclosure as described above or elsewhere herein.

In certain embodiments, each microbead presents at least 100 attached oligonucleotides having a microbead identification sequence that is common to all at least 100 oligonucleotides on each microbead, where the microbead identification sequence that is common to all at least 100 oligonucleotides on each microbead is either a microbead identification sequence that is unique to each microbead within each droplet of the droplet population or is a microbead identification sequence that is a member of a population of microbead identification sequences that is sufficiently degenerate to the population of microbeads within the droplet population that a majority of microbeads within the droplet population each possesses a unique microbead identification sequence.

Optionally, the nucleic acid sequence capable of hybridization and capture of genomic DNA is a random sequence.

In one embodiment, the droplet or droplet population is subjected to a slow-ramping amplification process to perform amplification of genomic DNA.

Optionally, the mammalian cell is a human cell.

In certain embodiments, the microbead(s) is of 1-100 μm in diameter, optionally the microbead(s) is approximately 10 μm in diameter.

Another aspect of the instant disclosure provides a method for making a droplet that includes a mammalian cell nucleus and a microbead presenting attached oligonucleotides, the method including: i) obtaining a mammalian cell; ii) freeze-thawing the mammalian cell; iii) contacting the mammalian cell with β-mercaptoethanol and heparin in an aqueous salt buffer and applying heat; iv) contacting the mammalian cell with heparinase in an amount sufficient to inactivate heparin, where steps (i)-(iv) thereby produce a mammalian cell nucleus having genomic DNA that is accessible to microbead-attached oligonucleotides, and v) combining within a droplet the mammalian cell nucleus and a microbead presenting attached oligonucleotides, thereby making a droplet that includes a mammalian cell nucleus and a microbead presenting attached oligonucleotides.

In one embodiment, the mammalian cell is a sperm cell.

In certain embodiments, the droplet includes a single mammalian cell nucleus and a single microbead presenting microbead-attached oligonucleotides.

Optionally, the droplet further includes reagents for mammalian genomic DNA amplification.

In certain embodiments, the droplet is subjected to an amplification process to perform amplification of genomic DNA, optionally where the amplification process is a slow-ramping amplification process.

In one embodiment, the mammalian cell nucleus genomic DNA is subjected to a next-generation sequencing technique, optionally where the mammalian cell nucleus genomic DNA is sequenced to at least 1% genomic coverage, optionally where the next-generation sequencing technique is solid-phase, reversible dye-terminator sequencing; massively parallel signature sequencing; pyro-sequencing; sequencing-by-ligation; ion semiconductor sequencing; nanopore sequencing or DNA nanoball sequencing, optionally where the next-generation sequencing technique is solid-phase, reversible dye-terminator sequencing.

Optionally, the sequence obtained via next-generation sequencing reveals the presence of aneuploidy in a sequenced mammalian cell. In certain embodiments, the sequence obtained via next-generation sequencing reveals the presence and/or elevated frequency (as compared to an appropriate, e.g., fertile or presumed fertile, control male) of aneuploidy in a sperm cell of a male partner of an infertile couple, optionally of aneuploidy in a sperm cell chromosome that is not a chromosome commonly assessed for presence of aneuploidy (e.g., aneuploidy in chromosomes other than chromosomes 21, 18 and/or 13).

In certain embodiments, the sequence obtained via next-generation sequencing reveals meiotic crossover patterns of a male partner of an infertile couple, which can optionally be compared to an appropriate control (optionally including appropriate control crossover frequencies and patterns).

Another aspect of the instant disclosure provides a kit for obtaining sperm genomic DNA sequence, the kit including: i) β-mercaptoethanol, heparin and heparinase; and ii) a population of microbeads presenting attached oligonucleotides, where the attached oligonucleotides include a nucleic acid sequence capable of hybridization and capture of sperm genomic DNA and a microbead identification sequence that is common to all oligonucleotides attached to each individual microbead of the population of microbeads, and instructions for use of the kit.

In one embodiment, the kit further includes reagents for mammalian genomic DNA amplification.

In another embodiment, the kit further includes reagents for next-generation sequencing optionally where the next-generation sequencing technique is solid-phase, reversible dye-terminator sequencing; massively parallel signature sequencing; pyro-sequencing; sequencing-by-ligation; ion semiconductor sequencing; nanopore sequencing or DNA nanoball sequencing, optionally where the next-generation sequencing technique is solid-phase, reversible dye-terminator sequencing.

Definitions

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value.

In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Unless otherwise clear from context, all numerical values provided herein are modified by the term "about."

As used herein, the term "amplicon," when used in reference to a nucleic acid, means the product of copying the nucleic acid, wherein the product has a nucleotide sequence that is the same as or complementary to at least a portion of the nucleotide sequence of the nucleic acid. An amplicon can be produced by any of a variety of amplification methods that use the nucleic acid, or an amplicon thereof, as a template including, for example, polymerase extension, polymerase chain reaction (PCR), rolling circle amplification (RCA), multiple displacement amplification (MBA), ligation extension, or ligation chain reaction. An amplicon can be a nucleic acid molecule having a single copy of a particular nucleotide sequence (e.g. a PCR product) or multiple copies of the nucleotide sequence (e.g. a concatameric product of RCA). A first amplicon of a target nucleic acid is typically a complementary copy. Subsequent amplicons are copies that are created, after generation of the first amplicon, from the target nucleic acid or from the first amplicon. A subsequent amplicon can have a sequence that is substantially complementary to the target nucleic acid or substantially identical to the target nucleic acid.

As used herein, the term "attached" refers to the state of two things being joined, fastened, adhered, connected or bound to each other. For example, an analyte, such as a nucleic acid, can be attached to a material, such as a gel or solid support, by a covalent or non-covalent bond. A covalent bond is characterized by the sharing of pairs of electrons between atoms. A non-covalent bond is a chemical bond that does not involve the sharing of pairs of electrons and can include, for example, hydrogen bonds, ionic bonds, van der Waals forces, hydrophilic interactions and hydrophobic interactions.

As used herein, the term "barcode sequence" is intended to mean a series of nucleotides in a nucleic acid that can be used to identify the nucleic acid, a characteristic of the nucleic acid (e.g., the identity and optionally the location of a bead to which the nucleic acid is attached), or a manipulation that has been carried out on the nucleic acid. The barcode sequence can be a naturally occurring sequence or a sequence that does not occur naturally in the organism from which the barcoded nucleic acid was obtained. A barcode sequence can be unique to a single nucleic acid species in a population or a barcode sequence can be shared by several different nucleic acid species in a population (e.g., all nucleic acid species attached to a single bead might possess the same barcode sequence, while different beads present a different shared barcode sequence that serves to identify each such different bead). By way of further example, each nucleic acid probe in a population can include different barcode sequences from all other nucleic acid probes in the population. Alternatively, each nucleic acid probe in a population can include different barcode sequences from some or most other nucleic acid probes in a population. For example, each probe in a population can have a barcode that is present for several different probes in the population even though the probes with the common barcode differ from each other at other sequence regions along their length. In particular embodiments, one or more barcode sequences that are used with a biological specimen (e.g., a sperm within a droplet) are not present in the genome, transcriptome or other nucleic acids of the biological specimen. For example, barcode sequences can have less than 80%, 70%, 60%, 50% or 40% sequence identity to the nucleic acid sequences in a particular biological specimen.

As used herein, "beads", "microbeads", "microspheres" or "particles" or grammatical equivalents can include small discrete particles. The composition of the beads can vary, depending upon the class of capture probe, the method of synthesis, and other factors. In certain embodiments of the instant disclosure, the sizes of the beads (microbeads) of the instant disclosure tend to range from about 1 µm to about 200 µm in diameter (with all subranges within this range expressly contemplated), e.g., depending upon droplet size, depth of sequencing coverage desired for individual cells, sequencing processes (e.g., flow cell sequencing) to be employed, as well as other factors.

As used herein, the term "biological specimen" is intended to mean one or more cell, tissue, organism or portion thereof. A biological specimen can be obtained from any of a variety of organisms. Exemplary organisms include, but are not limited to, a mammal such as a rodent, mouse, rat, rabbit, guinea pig, ungulate, horse, sheep, pig, goat, cow, cat, dog, primate (i.e. human or non-human primate); a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a Dictyostelium discoideum; a fungi such as *Pneumocystis carinii*, *Takifugu rubripes*, yeast, *Saccharamoyces cerevisiae* or *Schizosaccharomyces pombe*; or a *Plasmodium falciparum*. Target nucleic acids can also be derived from a prokaryote such as a bacterium, *Escherichia coli*, Staphylococci or *Mycoplasma pneumoniae*; an archae; a virus such as Hepatitis C virus or human immunodeficiency virus; or a viroid. Specimens can be derived from a homogeneous culture or population of the above organisms or alternatively from a collection of several different organisms, for example, in a community or ecosystem.

As used herein, the term "cleavage site" is intended to mean a location in a nucleic acid molecule that is susceptible to bond breakage. The location can be specific to a particular chemical, enzymatic or physical process that results in bond breakage. For example, the location can be a nucleotide that is abasic or a nucleotide that has a base that is susceptible to being removed to create an abasic site. Examples of nucleotides that are susceptible to being removed include uracil and 8-oxo-guanine. The location can also be at or near a recognition sequence for a restriction endonuclease such as a nicking enzyme.

By "control" or "reference" is meant a standard of comparison. Methods to select and test control samples are within the ability of those in the art. Determination of statistical significance is within the ability of those skilled in the art, e.g., the number of standard deviations from the mean that constitute a positive result.

As used herein, the term "different", when used in reference to nucleic acids, means that the nucleic acids have nucleotide sequences that are not the same as each other. Two or more nucleic acids can have nucleotide sequences that are different along their entire length. Alternatively, two or more nucleic acids can have nucleotide sequences that are different along a substantial portion of their length. For example, two or more nucleic acids can have target nucleotide sequence portions that are different for the two or more molecules while also having a universal sequence portion that is the same on the two or more molecules. Two beads can be different from each other by virtue of being attached to different nucleic acids.

As used herein, the term "each," when used in reference to a collection of items, is intended to identify an individual item in the collection but does not necessarily refer to every item in the collection. Exceptions can occur if explicit disclosure or context clearly dictates otherwise.

As used herein, the term "extend," when used in reference to a nucleic acid, is intended to mean addition of at least one nucleotide or oligonucleotide to the nucleic acid. In particular embodiments one or more nucleotides can be added to the 3' end of a nucleic acid, for example, via polymerase catalysis (e.g., DNA polymerase, RNA polymerase or reverse transcriptase). Chemical or enzymatic methods can be used to add one or more nucleotide to the 3' or 5' end of a nucleic acid. One or more oligonucleotides can be added to the 3' or 5' end of a nucleic acid, for example, via chemical or enzymatic (e.g., ligase catalysis) methods. A nucleic acid can be extended in a template directed manner, whereby the product of extension is complementary to a template nucleic acid that is hybridized to the nucleic acid that is extended.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation.

As used herein, the term "next-generation sequencing" or "NGS" can refer to sequencing technologies that have the capacity to sequence polynucleotides at speeds that were unprecedented using conventional sequencing methods (e.g., standard Sanger or Maxam-Gilbert sequencing methods). These unprecedented speeds are achieved by performing and reading out thousands to millions of sequencing reactions in parallel. NGS sequencing platforms include, but are not limited to, the following: Massively Parallel Signature Sequencing (Lynx Therapeutics™); 454 pyro-sequencing (454 Life Sciences/Roche Diagnostics™); solid-phase, reversible dye-terminator sequencing (Solexa™/Illumina™); SOLiD™ technology (Applied Biosystems™); Ion semiconductor sequencing (Ion Torrent™); and DNA nanoball sequencing (Complete Genomics™). Descriptions of certain NGS platforms can be found in the following: Shendure, et al., "Next-generation DNA sequencing," Nature, 2008, vol. 26, No. 10, 135-1 145; Mardis, "The impact of next-generation sequencing technology on genetics," Trends in Genetics, 2007, vol. 24, No. 3, pp. 133-141; Su, et al., "Next-generation sequencing and its applications in molecular diagnostics" Expert Rev Mol Diagn, 2011, 11 (3):333-43; and Zhang et al., "The impact of next-generation sequencing on genomics", J Genet Genomics, 201, 38(3): 95-109.

As used herein, the terms "nucleic acid" and "nucleotide" are intended to be consistent with their use in the art and to include naturally occurring species or functional analogs thereof. Particularly useful functional analogs of nucleic acids are capable of hybridizing to a nucleic acid in a sequence specific fashion or capable of being used as a template for replication of a particular nucleotide sequence. Naturally occurring nucleic acids generally have a backbone containing phosphodiester bonds. An analog structure can have an alternate backbone linkage including any of a variety of those known in the art. Naturally occurring nucleic acids generally have a deoxyribose sugar (e.g found in deoxyribonucleic acid (DNA)) or a ribose sugar (e.g. found in ribonucleic acid (RNA)). A nucleic acid can contain nucleotides having any of a variety of analogs of these sugar moieties that are known in the art. A nucleic acid can include native or non-native nucleotides. In this regard, a native deoxyribonucleic acid can have one or more bases selected from the group consisting of adenine, thymine, cytosine or guanine and a ribonucleic acid can have one or more bases selected from the group consisting of uracil, adenine, cytosine or guanine. Useful non-native bases that can be included in a nucleic acid or nucleotide are known in the art. The terms "probe" or "target," when used in reference to a nucleic acid or sequence of a nucleic acid, are intended as semantic identifiers for the nucleic acid or sequence in the context of a method or composition set forth herein and does not necessarily limit the structure or function of the nucleic acid or sequence beyond what is otherwise explicitly indicated. The terms "probe" and "target" can be similarly applied to other analytes such as proteins, small molecules, cells or the like.

As used herein, the term "subject" includes humans and mammals (e.g., mice, rats, pigs, cats, dogs, and horses). In many embodiments, subjects are mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

Unless specifically stated or obvious from context, as used herein, the term "or" is understood to be inclusive. Unless specifically stated or obvious from context, as used herein, the terms "a", "an", and "the" are understood to be singular or plural.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

The transitional term "comprising," which is synonymous with "including," "containing" or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

The embodiments set forth below and recited in the claims can be understood in view of the above definitions.

Other features and advantages of the disclosure will be apparent from the following description of the preferred embodiments thereof, and from the claims. Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All published foreign patents and patent applications cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

The following detailed description, given by way of example, but not intended to limit the disclosure solely to the specific embodiments described, may best be understood in conjunction with the accompanying drawings, in which:

FIG. 8 shows that sequence data obtained using the Sperm-seq approaches of the instant disclosure allowed for identification and quantification of crossover interference in each individual.

FIG. 18 shows examples of detection of aneuploidy in individual sperm cells. On the first row, examples of a sperm cell having chromosome 1 loss, a sperm cell having normal chromosome 1 ploidy and a sperm cell having an extra copy of chromosome 1 are shown (as in FIG. 17 above). On the middle row, examples of a sperm cell exhibiting loss of chromosome 5, a sperm cell exhibiting loss of chromosome 6, and a sperm cell exhibiting loss of chromosome 18 are shown (for this middle row, it is noted than an occasional mis-mapped sequence read produces a blip). On the bottom row, examples of a sperm cell exhibiting an extra copy of chromosome 1, a sperm cell exhibiting an extra copy of chromosome 4, and a sperm cell exhibiting an extra copy of chromosome 22 are shown. Each of these results was obtained for a different sperm, yet all sperm were obtained from the same donor.

FIG. 20 presents a tabulated listing of sperm donor and single-sperm sequencing characteristics and results. All data in FIG. 20 were obtained via the "Sperm-seq" single-sperm sequencing method of the instant disclosure. Key: #=These numbers are the total number of aneuploidy events divided by the total number of cells multiplied by 100; this is not precisely the percentage of cells with aneuploidy events as cells can have more than one event. $^a$=Sum across all cells from all sperm donors. $^b$=Median or mean across all individual cells from all sperm donors (31,228 measurements summarized). $^c$=Median or mean of aggregate metrics across samples (20 measurements summarized). $^d$=Median across all crossovers (813,122 measurements summarized).

FIG. 22A shows examples where chromosomes 2, 20 and 21, respectively, were sometimes present in an otherwise haploid sperm cell in 3 copies (nucleic acid sequences NC2, cell 5'-GTTACGCAATCGCT-3' (SEQ ID NO: 1); NC22, cell 5'-ACGACTAGTCAAGT-3' (SEQ ID NO: 2); and NC25, cell 5'-TTAGCGCAAAGTTG-3' (SEQ ID NO: 3) are shown). FIG. 22B shows an example where chromosome 15 was present in an otherwise haploid sperm cell in 3 copies (nucleic acid sequence NC22, cell 5'-AGTGTCTCGTAGTC-3' (SEQ ID NO: 4) is shown). FIG. 22C shows that a distinct triplication of chromosome 15, from ~33 Mb onwards, was observed in cells from 3 donors (one shown; nucleic acid sequence NC15, cell 5'-CAACTGGTAATCCC-3' (SEQ ID NO: 5) is shown). FIG. 22D shows an observed compound gain of the p arm and loss of the q arm of chromosome 4 (nucleic acid sequence NC9, cell 5'-ATGCCATCCGTGGC-3' (SEQ ID NO: 6) is shown). FIG. 22E shows an observed example of a many-copy (copy number is hard to precisely infer at high numbers) amplification of most of the q arm of chromosome 4 (~127 Mb). Over-representation of this region is observed to have depressed read depth in the rest of the genome to under 1 (nucleic acid sequence NC4, cell 5'-ATCTCTTCAGCCTA-3' (SEQ ID NO: 7) is shown).

DETAILED DESCRIPTION OF THE INVENTION

Figure 1:
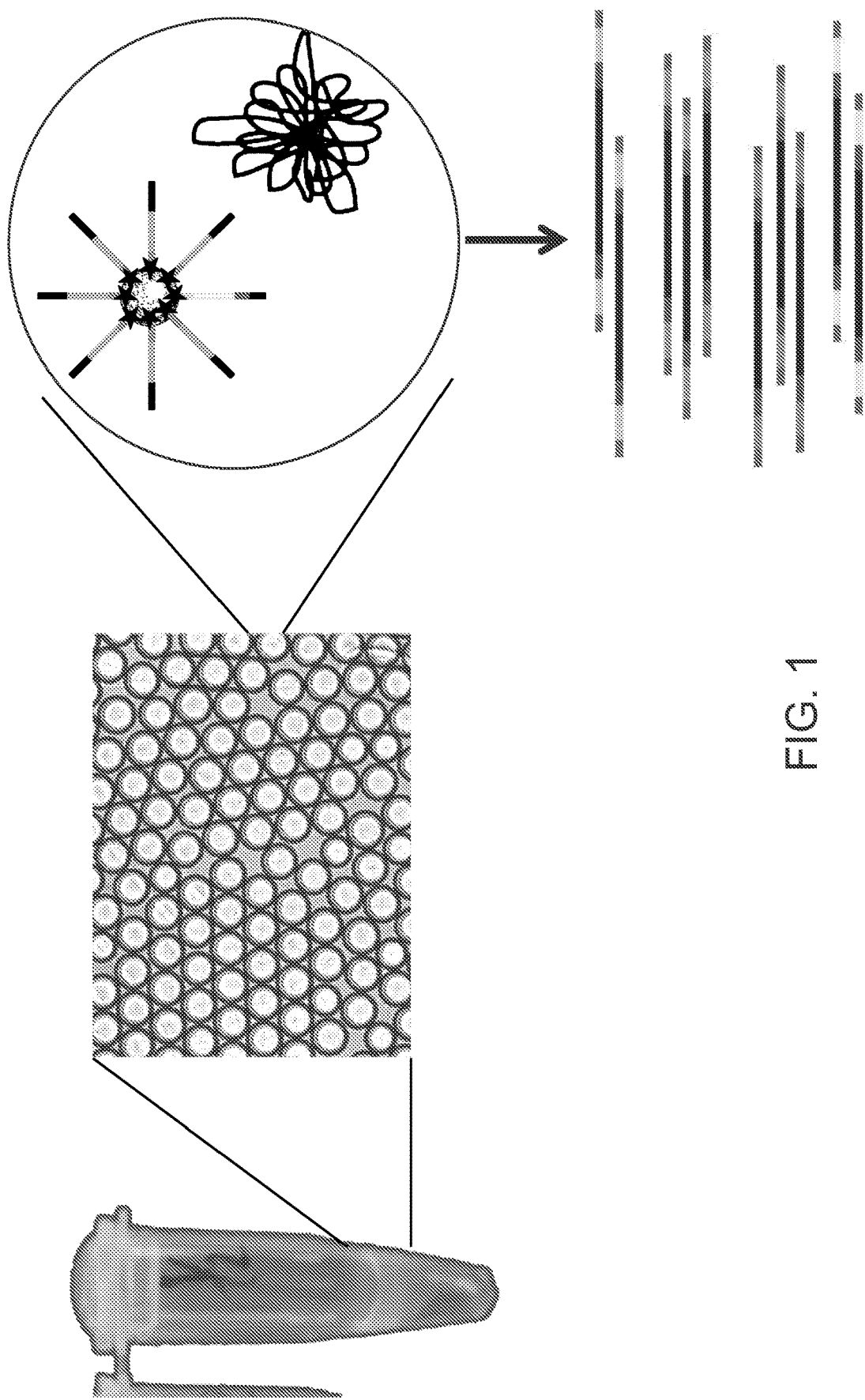
FIG. 1 shows a representative graphic of a droplet-based approach for obtaining genomic sequence from individual cellular genomes, via in-drop bead-based capture and amplification of genomic nucleic acids, with individual beads presenting oligonucleotide sequences that impart barcode labels to cell-derived amplicons.

The present disclosure is directed, at least in part, to the discovery of an approach for forming droplets useful for high-throughput bead-based oligonucleotide capture, amplification and sequencing of genomic DNA from single cells (e.g., single sperm cells) that involves maintaining the compartmental properties of a treated cell's nucleus (and therefore the microfluidic sortability of such a genomic DNA-harboring nucleus) while allowing access to the nuclear-encapsulated genomic DNA for oligonucleotide hybridization-based capture and amplification purposes. In certain aspects of the disclosure, a mammalian cell population is subjected to a rapid freeze-thaw, application of β-mercaptoethanol and heparin in an aqueous salt buffer, heating, and subsequent application of heparinase, which produces a population of cellular nuclei harboring accessible ("decondensed") genomic DNA that can be encapsulated into droplets (and individually paired with beads presenting barcoded capture oligonucleotides) via known microfluidic methods, subjected to massively parallel (in-droplet) genomic DNA capture and amplification, followed by next-generation sequencing of the bead-captured genomic DNA population of (barcode-presenting) amplicons.

The current disclosure solves the problem of quickly and easily sequencing the genomes of thousands of individual haploid sperm cells.

Sperm cells from one individual can be incredibly genetically different from one another, and pools of sperm cells from different individuals also differ. Improved understanding of these differences allows for insight into the crucial and error-prone biological processes that create sperm cells. These processes occur during meiosis, the cell division that generates sperm. Crossing over between chromosomes creates "crossovers" or "recombination events," the number and location of which differ among cells, and the failure of chromosomes to disjoin leads to aneuploidy, or the gain or loss of chromosomes. Aneuploidy is the cause of many miscarriages, and aneuploidies of most chromosomes are incompatible with development past early embryonic stages.

Additionally, infertility is very common, but there are very few diagnostic tests for male partners of couples experiencing infertility beyond gross sperm count and motility. Of cases where sperm count and motility are normal, 60% can be attributed to the female partner, while 40% are idiopathic and probably of male origin. Importantly, it is likely that genetic differences in sperm affect fertility outcomes, especially in idiopathic cases. Until now, there has been no method clinically available to look at the genomes of many individual sperm cells. Males with idiopathic infertility may, for example, have a higher proportion of their sperm with aneuploidy, thus leading to an inability of embryos to develop. This would be detectable upon sequencing many sperm from affected males.

Understanding genetic differences among sperm from one person, across individuals, and determining whether there are genetic abnormalities in sperm from infertile men requires a high-throughput way to sequence many sperm cells at once and analytical methods to glean data of interest from the sequence data. Such methods are described herein.

In particular, the current disclosure enables high-throughput light coverage single cell sequencing of individual sperm cells by creating single-sperm libraries in droplets. Previously, single-cell libraries have been made from sperm that were sorted into 96- or 384-well plates and amplified via various methods (e.g. MALBAC, as was used in Lu et al. 2012 [PMID: 23258895]; other approaches have been set forth in Wang et al. 2012 [PMID: 22817899], and Kirkness et al. 2013 [PMID: 23282328]). This required each single cell to have a full complement of library-generating reagents, within each single-cell-containing well. The methods of the instant disclosure combine enzyme-accessible sperm nuclei with barcoded beads in microfluidic droplets, enabling the creation of 600-1500 single sperm sequencing libraries in one reaction tube. Thus, much smaller total volumes of reagents are required, and hands-on time and difficulty is substantially decreased: previous studies have sequenced at most 100 single sperm; the instant methods have so far been employed to sequence 1000-2500 single sperm from each of 20 individuals (33,527 cells total).

Three specific techniques have been newly developed to combine enzyme-accessible sperm nuclei with barcoded beads in microfluidic droplets. In certain embodiments, a commercially available droplet- and bead-based sequencing kit (10× Genomics™, v1 DNA reagents (GemCode™) [PMID: 26829319], which includes library-generation reagents and barcoded beads; certain of the instant methods notably differ from the 10× Genomics™ kit protocol by changing the input nucleic acid to decondensed sperm nuclei and reducing the bead input 10-12-fold per reaction) has been employed for production of single-cell sequence from decondensed sperm nuclei, and commercially available microfluidic devices (e.g., of 10× Genomics™) have also been used to accomplish such droplet-based sequencing approaches.

A suite of software tools have also been developed and/or adapted, which take single sperm sequence generated using the instant methods of the disclosure through relevant analysis, which has included detecting the phase of the donor's genome at chromosome scale, identifying recombination events that happened in each sperm cell, and identifying gains or losses of chromosomes (aneuploidy) in each cell. These tools have allowed for measurement of aneuploidy frequency (likely of clinical value, particularly in the context of idiopathic male infertility, as described in additional detail elsewhere herein), recombination patterns, and relationships among these and other phenotypes that likely point to shared underlying biology. Previous single-cell sequencing analyses have been performed on largely sporadic, one-off bases, and on a much smaller scale (see, e.g., Lu et al. 2012 [PMID: 23258895], Wang et al. 2012 [PMID: 22817899], and Kirkness et al. 2013 [PMID: 23282328]).

The instant disclosure therefore combines the following key concepts:
1. Making sperm DNA accessible to enzymatic amplification while simultaneously maintaining the single-cell identity of the sperm nucleus. After a number of failed attempts, this has been accomplished by the methods of the instant disclosure by approximately adapting the egg's decondensation of the sperm pronucleus to the initial sperm population treatment methods. Briefly, in certain aspects of the instant disclosure, the sperm's protein coat is cracked via rapid freeze thawing, which is followed by removal of the protamines that tightly pack the DNA via addition of a salt buffer, beta-mercaptoethanol, and heparin and a heat treatment. (This decondensation method was adapted from the methods used in Montag et al. 1992 [PMID: 1449801] and Samocha-Bone et al. [PMID: 9542970].) Heparinase treatment is then applied to the preparation to remove heparin, a potent PCR inhibitor.

2. Combining cells/nuclei with a barcoded bead in a droplet, combining the barcode with the cell-derived nucleic acids inside the droplet (in this case, single-sperm DNA), and creating libraries where cell identity can be determined from this barcode. (Insights from Drop-seq [PMID: 26000488] and 10× Genomics™ [PMID: 26829319]; in certain embodiments as noted above, the instant methods use a commercially available kit (10× Genomics™ first-generation reagents) and tools to generate droplets and libraries; however, useful droplets have also been prepared and used, independent of such commercially available kits.)

The instant disclosure is based, at least in part, upon the identification and combination of these concepts, which has thereby enabled detection of single-cell sequence DNA within droplets. Exemplified genomic DNA has specifically come from sperm; however, it is contemplated that the instant methods can be adapted to other mammalian cell types to achieve in-droplet microbead-directed capture and amplification of genomic DNA, and therefore single-cell genomic DNA sequencing.

In certain embodiments of the instant disclosure, freeze-thaw of cells can be performed at least once, at least twice, or at least three times or more, e.g., via submersion in liquid nitrogen followed by placement in a 37° Celsius water bath.

In some embodiments, decondensation buffer can include any of a range of art-recognized salt buffers, as well as β-mercaptoethanol at about 0.1 mM to about 10 mM, optionally at about 0.2 mM to about 5 mM, optionally at about 0.5 mM to about 2 mM, optionally at about 1 mM, and heparin at a final concentration of about 10 mg/mL to about 100 mg/mL, optionally at about 20 mg/mL to about 70 mg/mL, optionally at about 35 mg/mL to about 45 mg/mL, optionally at about 40.5 mg/mL.

In certain embodiments, heparinase I treatment is performed by adding about 0.1 to about 10 Units of heparinase I per 25 microliters of sperm mixture, optionally about 0.2 to about 2 Units of heparinase I per 25 microliters of sperm mixture, optionally about 0.4 to about 1 Unit of heparinase I per 25 microliters of sperm mixture, optionally about 0.5 Units of heparinase I per 25 microliters of sperm mixture. Optionally, heparinase I treatment is performed at room temperature for a duration of at least 15 min, at least 30 min, at least 45 min, at least an hour, at least two hours, or more.

For non-gamete cells, it is expressly contemplated that the nucleus can be extracted and used as input into droplets for amplification, as exemplified elsewhere herein for sperm cells. A longer period of heat (95° Celsius) prior to the start of amplification is contemplated as likely to make genomic DNA accessible by denaturing the histones that typically pack genomic DNA. A highly processive and displacing polymerase (e.g., bacteriophage T5 polymerase, φ29 DNA polymerase, etc.), as is sometimes already used, is also expressly contemplated to help dislodge histones. It is also contemplated that non-sperm nuclei can be heat-treated prior to emotion in droplets as a means of making the genomic DNA therein more accessible to the instant bead capture methods, without destroying the nucleus.

Clinical Application of the Disclosure

Idiopathic male infertility is common and very poorly understood. It is specifically contemplated that the instant disclosure provides useful methods and compositions for use in diagnosis of cases of idiopathic infertility. If sperm count and motility and female reproductive parameters are normal, sequencing of many single sperm obtained from a male partner may show that the sperm are genetically abnormal (for example, having a much higher frequency of aneuploidy), thus helping clarify the cause of infertility and likely pointing to clinical next steps (such as using donor sperm).

In certain embodiments, the instant single-sperm sequencing methods can be used to sequence >500 single sperm from male partners of couples that exhibit idiopathic infertility. Optionally, analysis methods as set forth herein can be used to determine the patterns of recombination events and aneuploidy events in these sperm. If such results are abnormal, different clinical steps, such as pre-implantation genetic screening and/or using donor sperm, can be advised.

Research Application of the Disclosure

The methods described herein can also be used to understand patterns and variations in recombination, aneuploidy, and, potentially, new mutations in sperm from different individuals. All recombination events in each sperm cell can be identified by finding the transition between these phased haplotypes using a Hidden Markov Model (and possibly other methods). Aneuploidy events can be identified by looking at sequence/read depth across chromosomes (e.g., by using output from the software Genome STRiP [PMID: 25621458]). Patterns of these events and their co-variation can be determined from this information, which can be used to identify shared underlying biology. Specific patient or other populations of interest can be assayed to learn more about inter-individual differences in sperm production.

Additionally, the methods of the instant disclosure can be used to create chromosome-length haplotypes (phased genome) for the donor by using the software HapCUT [PMIDs: 18689818 and 24185094]. Phased genomes, especially at chromosome scale, are difficult to acquire using most short-read sequencing methods.

The methods disclosed herein can also be used to help improve genome assemblies for organisms that do not have excellent reference genomes. By looking at the combination of scaffolds present in individual haploid sperm cells, correct ordering and orientation of scaffolds into chromosomes can be determined. The instant methods have already been applied to demonstrate that this is possible with the marmoset (data not shown); and it is specifically contemplated that other mammals' sperm and genomes will be amenable to similar analyses.

Meiosis and recombination generate genetic diversity and many mutations. Prior work has inferred recombination events from genetic variation in pedigrees and populations (Coop et al. Science 319, 1395-8; Chowdhury et al. PLoS Genet 5, e1000648; Fledel-Alon et al. PLoS One 6, e20321; Hinch et al. Nature 476: 170-5; Kong et al. Nature 467: 1099-103; Kong et al. Nat Genet 46: 11-6) and has investigated a broader set of meiotic phenotypes in studies of 96-122 individual sperm cells (Lu et al. Science 338: 1627-30; Wang et al. Cell 150: 402-12; Kirkness et al. Genome Res 23: 826-32). Such previous studies have demonstrated that recombination varies among individuals, but cost and scalability have limited inferences about variation and co-variation of meiotic outcomes within individuals and across individual cells. (Indeed, Lu et al., Wang et al. and Kirkness et al. 2013 detailed analyses of single-sperm data resembling those exemplified herein, yet in each such method, single-sperm data was generated by methods distinct from those disclosed herein, and on a much smaller scale.)

Furthermore, crossovers are non-randomly distributed, appearing farther apart on chromosomes than would be expected by chance (Muller. The American Naturalist 50: 193-221). This "crossover interference" occurs in humans (Broman & Weber. Am J Hum Gen, 66(6): 1911-1926; Housworth & Stahl. Am J Hum Gen, 73(1): 188-197) and appears to decrease in extent in female meiosis with age (Campbell et al. Nat Comm, 6: 1-7). How and whether crossover interference varies among individuals, especially individual men, has remained, to date, unknown.

Certain aspects of the instant disclosure are directed towards description of "Sperm-seq", which is a droplet-based single-cell DNA sequencing technology for human sperm cells that, among other advantages as described herein, imparts the advantage of greatly expanding the ability to measure and learn from meiotic outcomes in single sperm cells. The methods of the instant disclosure have made it routine to generate sequencing libraries for 1000-2000 individual sperm cells, sequence them to low coverage (generally 0.01-0.02×, though up to 0.1× is permitted by the complexity of currently exemplified Sperm-seq libraries) and infer recombination patterns and chromosomal ploidy for each cell. Complete phasing of human genomes has been made possible using Sperm-seq data, which has been used to produce whole genome sequence data in which all heterozygous SNPs are phased into chromosome-length haplotypes. In exemplified embodiments, crossovers have been identified in each gamete using a Hidden Markov Model to find transitions between haplotypes. Aneuploidy events have also been detected from deviations in sequence coverage and the presence of multiple haplotypes.

The recombination maps produced via use of the methods of the instant disclosure correlate broadly with pedigree- and population-based male recombination maps, including concentration of crossovers near the telomeres, yet they exhibit substantial inter individual differences.

The instant data sets are also being analyzed to characterize meiotic outcomes, such as frequency and meiotic division of origin of aneuploidy and spatial distribution of crossovers, as well as investigating the relationships among them, their inter-individual variation, and their co-variation across cells.

As documented below, inter-individual variation in the extent and pattern of crossover interference—the tendency of crossovers on the same chromosome to occur farther apart from one another than would b e expected by chance—was also examined. Crossover interference was specifically identified in each of the 20 individuals examined (median distance between adjacent crossovers per individual was identified as 68-90 Mb, $p<<<10^{-4}$ in a permutation test randomly assigning crossovers to cells). The magnitude of crossover interference differed among individuals and negatively correlated with recombination rate.

The sperm sequencing and analysis approaches set forth herein have, to date, been used to sequence 33,527 single sperm from 20 donors (1000-2500 sperm per donor) of presumed normal fertility, which has yielded sequence coverage of 0.8-4% of the genome of each of 1,100-2,400 sperm cells per individual. In each haploid cell, a median of 13,000 SNPs that were heterozygous in the sperm donor were genotyped. Phased genomes were obtained for each donor and recombination and aneuploidy events in each sperm cell were thereby identified. The results of these data are presented herein. Further analyses of these data are also ongoing.

As described herein, the instant disclosure provides for routinely making sequencing libraries for 1000-2000 individual sperm cells, sequencing them to low coverage (generally capturing 1-2% of the genome, though up to at least 10% is possible). Complete phasing of human genomes can also be performed using the sequence data obtained using the methods and compositions of the instant disclosure, generating whole genome sequence data in which all heterozygous SNPs are phased into chromosome-length haplotypes (by adapting HapCUT, Bansal & Bafna. Bioinformatics 24, i153-9; Selvaraj et al. Nat Biotechnol 31: 1111-8). Crossovers have been identified in each gamete using a Hidden Markov Model to find transitions between haplotypes. Aneuploidy events have been recognized across all chromosomes and cells from deviations in sequence coverage (determined with Genome STRiP, Handsaker et al. Nat Genet 47: 296-303) and the presence of multiple haplotypes.

In certain embodiments, the instant disclosure enables cost-effective, high-throughput sequencing of sperm obtained from male partners in couples with infertility, e.g., thereby allowing for identification of instances of idiopathic infertility attributable to male sperm characteristics (e.g, increased frequency of aneuploidy events in sperm, etc.).

Various expressly contemplated components of certain compositions and methods of the instant disclosure are considered in additional detail below.

Microbeads

Certain aspects of the instant disclosure employ a collection of microbeads or other particles, to which oligonucleotides are attached. Suitable microbead compositions include those used in peptide, nucleic acid and organic moiety synthesis, including, but not limited to, plastics, ceramics, glass, polystyrene, methylstyrene, acrylic polymers, paramagnetic materials, thoriasol, carbon graphite, titanium dioxide, latex or cross-linked dextrans such as Sepharose, cellulose, nylon, cross-linked micelles and Teflon™ may all be used. "Microsphere Detection Guide" from Bangs Laboratories, Fishers Ind. is a helpful guide, which is incorporated herein by reference in its entirety. The microbeads need not be spherical; irregular particles may be used. In addition, the microbeads may be porous, thus increasing the surface area of the microbead available for either capture probe attachment or tag attachment. The microbead sizes can range from nanometers, for example, 100 nm, to about 200 µm, with microbeads from about 0.2 µm to about 200 µm commonly employed, and from about 5 to about 20 µm being within the range currently exemplified, although in some embodiments smaller or larger beads may be used.

A collection of microbeads can include different microbeads each having a unique (or sufficiently unique and/or near-unique, as described elsewhere herein) oligonucleotide attached. It will however, be understood that the microbeads can be made to include universal primers.

In certain embodiments, the compositions and methods described herein use barcoded oligonucleotide-laden microbeads to capture genomic DNA from individual mammalian cells (e.g, sperm cells as exemplified herein), within droplets (where the use of droplets allows for massively parallel treatment of individual droplet-encapsulated microbead-single cell pairs within droplets, at minimal cost as compared, e.g., to well-based approaches of DNA capture and/or amplification). Exemplified microbeads are synthesized with a unique or sufficiently unique microbead barcode as previously described, e.g., in WO 2016/040476 (PCT/US2015/049178), wherein an exemplary sufficiently unique microbead barcode is one that is a member of a population of barcode sequences that is sufficiently degenerate to a population (e.g., of microbeads) that a majority of individual components (e.g. microbeads) of the barcoded population each possesses a unique barcode sequence, where the remainder (minority) of the population may possess barcodes that are redundant with those of other members within the remainder population, yet such redundancy can either be eliminated or otherwise adjusted for (e.g., normalized, averaged across/between redundant members, etc.) with only minor impact upon, e.g., single-cell genomic DNA sequence derived from a tested cell population.

In certain embodiments, a population of the microbeads can be configured such that each microbead is attached to only one type of barcode (e.g., a barcode that specifically identifies a microbead and/or microbead-associated cell from which a sequence derived) and many different microbeads each with a different barcode are present in the population. In this embodiment, randomly distributing the microbeads to a population of droplets will result in randomly locating the nucleic acid probe-presenting microbeads (and their respective barcode sequences) in the population of droplets. In some cases, there can be multiple microbeads with the same barcode sequence such that there is redundancy in the population. However, randomly distributing a redundancy-comprising population of microbeads to a droplet population—especially one that has a capacity that is greater than the number of unique barcodes in the microbead population—will tend to result in redundancy of barcodes within the droplet population, which will tend to produce a small population of droplets that exhibit redundancies, but it is contemplated that such redundant droplets can simply be eliminated from an ultimate population of single-cell-derived sequences produced by methods of the instant disclosure (for sperm cells especially, it will be clear which barcode sequences are actually associated with multiple sperm cells, rather than single sperm cells, due to an abundance of heterozygous SNPs within such sequences derived from multiple sperm cells), or other modes of adjustment (e.g., normalization and/or averaging of values) may also be employed to address such redundancies). Alternatively, in certain embodiments, the number of different barcodes in a population of microbeads can exceed the droplet population size, thereby producing a population of barcoded reads that does not exhibit redundancy and/or exhibits very little redundancy (i.e., for the vast majority of barcodes, one barcode=a unique cell).

A microbead of the instant disclosure can include or can be made by the methods set forth herein to attach, a plurality of different nucleic acid probes. For example, a microbead can include at least 10, 100, $1 \times 10^3$, $1 \times 10^4$, $1 \times 10^5$, $1 \times 10^6$, $1 \times 10^7$, $1 \times 10^8$, $1 \times 10^9$ or more different probes. Alternatively or additionally, a microbead can include at most $1 \times 10^9$, $1 \times 10^8$, $1 \times 10^7$, $1 \times 10^6$, $1 \times 10^5$, $1 \times 10^4$, $1 \times 10^3$, 100, or fewer different probes. It will be understood that each of the different probes can be present in several copies, for example, when the probes have been amplified to form a cluster. Thus, the above ranges can describe the number of different nucleic acid clusters on a microbead of the instant disclosure. It will also be understood that the above ranges can describe the number of different barcodes, target capture sequences, or other sequence elements set forth herein as being unique (or sufficiently unique) to particular nucleic acid probes. Alternatively or additionally, the ranges can describe the number of extended probes or modified probes created on a microbead of the instant disclosure using a method set forth herein.

Features may be present on a microbead of the instant disclosure prior to contacting the microbead with nucleic acid probes (e.g., oligonucleotides). For example, in embodiments where probes are attached to a microbead via hybridization to primers, the primers can be attached at the features, whereas interstitial areas outside of the features substantially lack any of the primers. Nucleic acid probes can be captured at preformed features on a microbead, and optionally amplified on the microbead, e.g., using methods set forth in U.S. Pat. Nos. 8,895,249 and 8,778,849 and/or U.S. Patent Publication No. 2014/0243224 A1, each of which is incorporated herein by reference. Alternatively, a microbead may have a lawn of primers or may otherwise lack features. In this case, a feature can be formed by virtue of attachment of a nucleic acid probe on the microbead. Optionally, the captured nucleic acid probe can be amplified on the microbead such that the resulting cluster becomes a feature. Although attachment is exemplified above as capture between a primer and a complementary portion of a probe, it will be understood that capture moieties other than primers can be present at pre-formed features or as a lawn. Other exemplary capture moieties include, but are not limited to, chemical moieties capable of reacting with a nucleic acid probe to create a covalent bond or receptors capable of binding non-covalently to a ligand on a nucleic acid probe.

A step of attaching nucleic acid probes (e.g., oligonucleotides) to a microbead can be carried out by providing a fluid that contains a mixture of different nucleic acid probes and contacting this fluidic mixture with the microbead. The contact can result in the fluidic mixture being in contact with a surface to which many different nucleic acid probes from the fluidic mixture will attach. Thus, the probes have random access to the surface (whether the surface has pre-formed features configured to attach the probes or a uniform surface configured for attachment). Accordingly, the probes can be randomly located on the microbead.

The total number and variety of different probes that end up attached to a surface can be selected for a particular application or use. For example, in embodiments where a fluidic mixture of different nucleic acid probes is contacted with a microbead for purposes of attaching the probes to the support, the number of different probe species can exceed the occupancy of the microbead for probes. Thus, the number and variety of different probes that attach to the microbead can be equivalent to the probe occupancy of the microbead.

Alternatively, the number and variety of different probe species on the microbead can be less than the occupancy (i.e. there will be redundancy of probe species such that the microbead may contain multiple features having the same probe species). Such redundancy can be achieved, for example, by contacting the microbead with a fluidic mixture that contains a number and variety of probe species that is substantially lower than the probe occupancy of the microbead.

Attachment of the nucleic acid probes can be mediated by hybridization of the nucleic acid probes to complementary primers that are attached to the microbead, chemical bond formation between a reactive moiety on the nucleic acid probe and the microbead (examples are set forth in U.S. Pat. Nos. 8,895,249 and 8,778,849, and in U.S. Patent Publication No. 2014/0243224 A1, each of which is incorporated herein by reference), affinity interactions of a moiety on the nucleic acid probe with a bead- or other solid support-bound moiety (e.g. between known receptor-ligand pairs such as streptavidin-biotin, antibody-epitope, lectin-carbohydrate and the like), physical interactions of the nucleic acid probes with the microbead (e.g. hydrogen bonding, ionic forces, van der Waals forces and the like), or other interactions known in the art to attach nucleic acids to surfaces.

In some embodiments, attachment of a nucleic acid probe is non-specific with regard to any sequence differences between the nucleic acid probe and other nucleic acid probes that are or will be attached to the microbead. For example, different probes can have a universal sequence that complements surface-attached primers or the different probes can have a common moiety that mediates attachment to the surface. Alternatively, each of the different probes (or a subpopulation of different probes) can have a unique (or sufficiently unique) sequence that complements a unique (or sufficiently unique) primer on the microbead or they can have a unique (or sufficiently unique) moiety that interacts with one or more different reactive moiety on the microbead. In such cases, the unique (or sufficiently unique) primers or unique (or sufficiently unique) moieties can, optionally, be attached at predefined locations in order to selectively capture particular probes, or particular types of probes, at the respective predefined locations.

One or more features on a microbead can each include a single molecule of a particular probe. The features can be configured, in some embodiments, to accommodate no more than a single nucleic acid probe molecule. However, whether or not the feature can accommodate more than one nucleic acid probe molecule, the feature may nonetheless include no more than a single nucleic acid probe molecule. Alternatively, an individual feature can include a plurality of nucleic acid probe molecules, for example, an ensemble of nucleic acid probe molecules having the same sequence as each other. In particular embodiments, the ensemble can be produced by amplification from a single nucleic acid probe template to produce amplicons, for example, as a cluster attached to the surface.

A method set forth herein can use any of a variety of amplification techniques. Exemplary techniques that can be used include, but are not limited to, polymerase chain reaction (PCR), Multiple Annealing and Looping Based Amplification Cycles (a.k.a. MALBAC), rolling circle amplification (RCA), multiple displacement amplification (MDA), or random prime amplification (RPA). In some embodiments the amplification can be carried out in solution.

MALBAC (Optional)

In certain embodiments Multiple Annealing and Looping Based Amplification Cycles (a.k.a. MALBAC) can be used for droplet-based amplification of bead-captured genomic DNA. MALBAC is a quasilinear whole genome amplification method. Unlike conventional DNA amplification methods that are non-linear or exponential (in each cycle, DNA copied can serve as template for subsequent cycles), MALBAC utilizes special primers that allow amplicons to have complementary ends and therefore to loop, preventing DNA from being copied exponentially. This results in amplification of only the original genomic DNA and therefore reduces amplification bias. MALBAC is "used to create overlapped shotgun amplicons covering most of the genome" (Zong et al. Science 338: 1622). For next generation sequencing, MALBAC is followed by regular PCR which is used to further amplify amplicons.

In certain embodiments, MALBAC single-cell whole-genome amplification involves 5 cycles of quenching, extending, melting, and looping.

The major advantage of MALBAC is that DNA is amplified almost linearly. The utilization of specialized primers enables looping of amplicons which then prevents them from being further amplified in subsequent cycles of MALBAC. These primers are 35 nucleotides long, with 8 variable nucleotides that hybridize to the templates and 27 common nucleotides (Zong et al.). The common nucleotide sequence is GTG AGT GAT GGT TGA GGT AGT GTG GAG (SEQ ID NO: 8). The 8 variable nucleotides anneal randomly to the single stranded genomic DNA molecule. After one extension, semi-amplicon, an amplicon containing the common nucleotide sequence on only the 5' end, is made. This semi-amplicon is used as a template for another round of extension, which then results in a full-amplicon, an amplicon where the 3' end is complementary to the sequence on the 5' end.

MALBAC primers have variable components which allow them to randomly bind to the template DNA. This means that on a single fragment at any cycle, there could be multiple primers annealed to the fragment. A DNA polymerase such as one derived from *Bacillus stearothermophilus* (Bst polymerase) is able to displace the 5' end of another upstream strand growing in the same direction (Aviel-Ronen et al. BMC Genomics 7. PMID 17156491). Bst DNA polymerase has an error rate of 1/10000 bases (Ausubel et al. CURRENT PROTOCOLS IN MOLECULAR BIOLOGY, Vol. I., John Wiley & Songs, Inc. 1995. Pp 7.4.18).

A standard MALBAC process involves the following, though it is noted that the instant disclosure has adapted the below process to allow for droplet-based performance of an initial MALBAC amplification process (loading all necessary components for such an initial amplification during droplet formation, and only lysing the droplet once, e.g., a bead-associated barcode has been incorporated into initial genomic DNA-derived amplicons):

1. Single-cell isolation and lysis—pg of genomic DNA fragments (10 to 100 kb) isolated from a single-cell are used as templates. In the methods of the instant disclosure, droplet-encapsulated single-cell nuclei can function as the input DNA in such a MALBAC reaction.
2. Melting—At 94° C., double-stranded DNA molecules are melted into single stranded forms.
3. Quenching—After melting, the reaction is immediately quenched to 0° C., and MALBAC primers are added to the reaction. (Or, in the embodiments of the instant disclosure, such primers are simply present within the droplet at the initiation of genomic DNA capture and subsequent MALBAC primer-mediated amplification.)
4. Extension—Bst DNA Polymerase (Large Fragment) extends the primers at 65° C. for 2 mins, creating semi-amplicons.
5. Melting—The reaction is heated to back to 94° C. to separate the semi-amplicon from the genomic DNA template.
6. Quenching—The reaction is quickly quenched at 0° C., and followed by the addition of the same polymerase mix. The MALBAC primers efficiently bind to both semi-amplicons and genomic DNA template.
7. Extension—Bst DNA Polymerase (Large Fragment) extends the primers at 65° C. for 2 mins. At this step, full-amplicons are made for those that used semi-amplicons as templates, and also semi-amplicons are made for those that used the genomic DNA template as templates.
8. Melting—The reaction is heated to 94° C. to separate the amplicons from the template.
9. Looping—For full amplicons, the 3' end sequence is now complementary to the 5' end. At 58° C., the two ends hybridize forming a looped DNA. This prevents the full amplicon from being used as a template in subsequent MALBAC cycles.
10. Repeat steps 6-9 five times—5 cycles of linear MALBAC amplification.
11. RegularPCR—The MALBAC product is further amplified by PCR. By using the 27 common nucleotides as primers, only the full amplicons are amplified.

At the end of PCR, picograms of genetic material is amplified to microgram of DNA, yielding enough DNA to be sequenced.

RCA techniques can be modified for use in a method of the present disclosure. Exemplary components that can be used in an RCA reaction and principles by which RCA produces amplicons are described, for example, in Lizardi et al., Nat. Genet. 19:225-232 (1998) and U.S. Patent Publication No. 2007/0099208 A1, each of which is incorporated herein by reference. Primers used for RCA can be in solution or attached to a microbead. The primers can be one or more of the universal primers described herein.

MDA techniques can be modified for use in a method of the present disclosure. Some basic principles and useful conditions for MDA are described, for example, in Dean et al., Proc Natl. Acad. Sci. USA 99:5261-66 (2002); Lage et al., Genome Research 13:294-307 (2003); Walker et al., Molecular Methods for Virus Detection, Academic Press, Inc., 1995; Walker et al., Nucl. Acids Res. 20:1691-96 (1992); U.S. Pat. Nos. 5,455,166; 5,130,238; and U.S. Pat. No. 6,214,587, each of which is incorporated herein by reference. Primers used for MDA can be in solution or attached to a microbead at an amplification site. Again, the primers can be one or more of the universal primers described herein.

In particular embodiments a combination of the above-exemplified amplification techniques can be used. For example, RCA and MDA can be used in a combination wherein RCA is used to generate a concatameric amplicon in solution (e.g. using solution-phase primers). The amplicon can then be used as a template for MDA using primers that are attached to a microbead (e.g. universal primers). In this example, amplicons produced after the combined RCA and MDA steps will be attached to the microbead.

Nucleic acid probes that are used in a method set forth herein or present in an apparatus or composition of the present disclosure can include barcode sequences, and for embodiments that include a plurality of different nucleic acid probes, each of the probes can include a different barcode sequence from other probes in the plurality. Barcode sequences can be any of a variety of lengths.

Longer sequences can generally accommodate a larger number and variety of barcodes for a population. Generally, all probes in a plurality will have the same length barcode (albeit with different sequences), but it is also possible to use different length barcodes for different probes. A barcode sequence can be at least 2, 4, 6, 8, 10, 12, 15, 20 or more nucleotides in length. Alternatively or additionally, the length of the barcode sequence can be at most 20, 15, 12, 10, 8, 6, 4 or fewer nucleotides. Examples of barcode sequences that can be used are set forth, for example in, U.S. Patent Publication No. 2014/0342921 A1 and U.S. Pat. No. 8,460, 865, each of which is incorporated herein by reference.

A method of the present disclosure can include a step of performing a nucleic acid detection reaction on a microbead to determine barcode sequences of nucleic acid probes that are located on the microbead. In many embodiments the probes are randomly located on the microbead and the nucleic acid detection reaction provides information to locate each of the different probes. Exemplary nucleic acid detection methods include, but are not limited to nucleic acid sequencing of a probe, hybridization of nucleic acids to a probe, ligation of nucleic acids that are hybridized to a probe, extension of nucleic acids that are hybridized to a probe, extension of a first nucleic acid that is hybridized to a probe followed by ligation of the extended nucleic acid to a second nucleic acid that is hybridized to the probe, or other methods known in the art such as those set forth in U.S. Pat. No. 8,288,103 or 8,486,625, each of which is incorporated herein by reference.

Sequencing techniques, such as sequencing-by-synthesis (SBS) techniques, are a useful method for determining barcode sequences. SBS can be carried out as follows. To initiate a first SBS cycle, one or more labeled nucleotides, DNA polymerase, SBS primers etc., can be contacted with one or more features on a microbead (e.g. feature(s) where nucleic acid probes are attached to the microbead). Those features where SBS primer extension causes a labeled nucleotide to be incorporated can be detected. Optionally, the nucleotides can include a reversible termination moiety that terminates further primer extension once a nucleotide has been added to the SBS primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the microbead (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use with a composition, apparatus or method of the present disclosure are described, for example, in Bentley et al., Nature 456:53-59 (2008), PCT Publ. Nos. WO 91/06678, WO 04/018497 or WO 07/123744; U.S. Pat. Nos. 7,057,026, 7,329,492, 7,211,414, 7,315,019 or 7,405,281, and U.S. Patent Publication No. 2008/0108082, each of which is incorporated herein by reference.

Other sequencing procedures that use cyclic reactions can be used, such as pyrosequencing Pyrosequencing detects the release of inorganic pyrophosphate (PPi) as particular nucleotides are incorporated into a nascent nucleic acid strand (Ronaghi, et al., Analytical Biochemistry 242(1), 84-9 (1996); Ronaghi, Genome Res. 1 1 (1), 3-1 1 (2001); Ronaghi et al. Science 281 (5375), 363 (1998); or U.S. Pat. Nos. 6,210,891, 6,258,568 or 6,274,320, each of which is incorporated herein by reference). In pyrosequencing, released PPi can be detected by being immediately converted to adenosine triphosphate (ATP) by ATP sulfurylase, and the level of ATP generated can be detected via luciferase-produced photons. Thus, the sequencing reaction can be monitored via a luminescence detection system.

Bead-Attached Oligonucleotides

Certain aspects of the instant disclosure employ a nucleotide- or oligonucleotide-adorned bead (microbead), where the bead-attached oligonucleotide includes one or more of the following a linker (optionally a cleavable linker, optionally a photocleavable linker); an identical sequence for use as a sequencing priming site; a uniform or near-uniform nucleotide or oligonucleotide sequence; a Unique Molecular Identifier which differs for each priming site; a nucleic acid sequence capable of hybridizing to and capturing genomic DNA (optionally a random sequence that anneals to the targeted mammalian genome); and at least one oligonucleotide barcode which provides an substrate for identification of an individual bead's associated mammalian cell from which capture of genomic DNA has occurred. Exemplified bead-attached oligonucleotides of the instant disclosure include an oligonucleotide barcode designed to be unique to each bead within a bead array (or at least wherein the majority of such barcodes are unique to a bead within a bead population—e.g., it is expressly contemplated here and elsewhere herein that a bead population possessing only a small fraction of beads (e.g., even up to 10%, 20%, 30% or 40% or more of total beads) having non-unique barcodes (e.g., attributable to a relative lack of degeneracy within the bead population, e.g., due to a probabilistically determinable lack of sequence degeneracy calculated as possible within the bead population, as then compared to the number of total cells to which the bead population is ultimately applied and/or due to an artifact such as non-randomness of bead association occurring during pool-and-split rounds of oligonucleotide synthesis, etc.) could still yield a high proportion of valuable, single-cell-of-origin-defined sequence, even while removing (or otherwise adjusting for) any beads that turn out to be redundant in barcode within the population). This barcode provides a substrate for identification. Exemplified bead-attached oligonucleotides of the instant disclosure also include a linker (optionally a cleavable linker); MALBAC primers and/or sequences as described elsewhere herein; a Unique Molecular Identifier (UMI) which differs for each priming site (as known in the art, e.g., see WO 2016/040476); a barcode as described above and elsewhere herein; and a common sequence ("PCR handle") to enable PCR amplification after capture of targeted genomic DNA sequences upon beads.

Exemplary split-and-pool synthesis of the bead barcode: To generate a cell barcode of 12 nucleotides in length, a pool of microparticles (here, microbeads) is repeatedly split into four equally sized oligonucleotide synthesis reactions, to which one of the four DNA bases is added, and then pooled together after each cycle, in a total of 12 split-pool cycles. The barcode synthesized on any individual bead reflects that bead's unique (or sufficiently unique) path through the series of synthesis reactions. The result is a pool of microparticles, each possessing one of $4^{12}$ (16,777,216) possible sequences on its entire complement of primers. Extension of the split-pool process can provide for, e.g., production of an even greater number of possible barcode sequences for use in the compositions and methods of the instant disclosure. However, as noted above, functional use of bead-identifying barcodes does not require complete non-redundancy of barcodes among all beads of a bead population. Rather, provided that the majority of such barcodes are unique to a bead within a bead population, it is expressly contemplated that a bead population possessing only a small fraction of beads (e.g., even up to 10%, 20%, 30% or 40% or more of total beads) having non-unique barcodes (e.g., attributable to an artifact such as non-randomness of bead association having occurred during pool-and-split rounds of oligonucleotide synthesis, or simply to the likelihood that population of a million beads derived from a ten million-fold complex library would still be expected to include a number of beads having redundant barcodes in pairwise comparisons across a bead population that is (approximately) pairwise applied to a cellular population) could still yield highly valuable single-cell sequence information, where removal or other adjustment (averaging or other such adjustment) of any beads that turn out to be redundant in barcode within the population could be simply performed, e.g., during in silco association of resultant genomic DNA amplicon-derived sequences with their respective cell(s) of origin.

Exemplary synthesis of a unique molecular identifier (UMI). Following the completion of the "split-and-pool" synthesis cycles described above for generation of barcodes, all microparticles can optionally together b e subjected to eight rounds of degenerate synthesis with all four DNA bases available during each cycle, such that each individual primer receives one of $4^8$ (65,536) possible sequences (UMIs). A UMI is thereby provided that allows distinguishing between, e.g., individual bead-attached oligonucleotides upon the same bead which otherwise share a common barcode (being that such oligonucleotides are attached to the same bead and therefore receive the same barcode).

In some embodiments of the instant disclosure, the linker of a bead-attached oligonucleotide is a chemically-cleavable, straight-chain polymer. Optionally, the linker is a photolabile optionally substituted hydrocarbon polymer. In certain embodiments, the linker of a bead-attached oligonucleotide is a non-cleavable, straight-chain polymer. Optionally, the linker is a non-cleavable, optionally substituted hydrocarbon polymer. In certain embodiments, the linker is a polyethylene glycol. In one embodiment, the linker is a PEG-C3 to PEG-24.

A nucleic acid probe used in a composition or method set forth herein can include a target capture moiety. In particular embodiments, the target capture moiety is a target capture sequence. The target capture sequence is generally complementary to a target sequence such that target capture occurs by formation of a probe-target hybrid complex. A target capture sequence can be any of a variety of lengths including, for example, lengths exemplified above in the context of barcode sequences.

In certain embodiments, a plurality of different nucleic acid probes can include different target capture sequences that hybridize to different target nucleic acid sequences from a biological specimen. Different target capture sequences can be used to selectively bind to one or more desired target nucleic acids from a biological specimen. In some cases, the different nucleic acid probes can include a target capture sequence that is common to all or a subset of the probes on a bead, or the target capture sequences can be highly variable with one another, optionally random capture sequences, e.g., for capture of genomic DNA at a relatively high level of genomic representation.

Particular target sequences can optionally be selected from databases and appropriate capture sequences designed using techniques and databases known in the art.

A method set forth herein can include a step of hybridizing nucleic acid probes, that are on a microbead, to target genomic DNA of a single cell. A target-probe hybrid complex can form where the target nucleic acid encounters a complementary target capture sequence on a nucleic acid probe. The sequences of the target nucleic acids and associated barcodes applied during amplification steps will provide information about the cell of origin of a next-gen sequencing read obtained.

A method of the present disclosure can include a step of extending bead-attached probes (oligonucleotides) to which target nucleic acids are hybridized. In embodiments where the probes include barcode sequences, the resulting extended probes will include the barcode sequences and sequences from the target nucleic acids (albeit in complementary form). The extended probes are thus tagged versions of the target nucleic acids from the cellular population. The sequences of the extended probes identify what nucleic acids are in the cellular population and from which individual cell each of the sequence reads derives. It will be understood that other sequence elements that are present in the nucleic acid probes can also be included in the extended probes (see, e.g., description as provided elsewhere herein). Such elements include, for example, primer binding sites, cleavage sites, other tag sequences, capture sequences, recognition sites for nucleic acid binding proteins or nucleic acid enzymes, or the like.

Extension of probes can be carried out using methods exemplified herein or otherwise known in the art for amplification of nucleic acids or sequencing of nucleic acids. In particular embodiments one or more nucleotides can be added to the 3' end of a nucleic acid, for example, via polymerase catalysis (e.g. DNA polymerase). Chemical or enzymatic methods can be used to add one or more nucleotide to the 3' or 5' end of a nucleic acid. One or more oligonucleotides can be added to the 3' or 5' end of a nucleic acid, for example, via chemical or enzymatic (e.g. ligase catalysis) methods. A nucleic acid can be extended in a template directed manner, whereby the product of extension is complementary to a template nucleic acid that is hybridized to the nucleic acid that is extended. Exemplary methods for extending nucleic acids are set forth in US Pat. App. Publ. No. US 2005/0037393 A1 or U.S. Pat. No. 8,288,103 or 8,486,625, each of which is incorporated herein by reference.

All or part of a target nucleic acid that is hybridized to a nucleic acid probe can be copied by extension. For example, an extended probe can include at least, 1, 2, 5, 10, 25, 50, 100, 200, 500, 1000 or more nucleotides that are copied from a target nucleic acid. The length of the extension product can be controlled, for example, using reversibly terminated nucleotides in the extension reaction and running a limited number of extension cycles.

Accordingly, an extended probe produced in a method set forth herein can include no more than 1000, 500, 200, 100, 50, 25, 10, 5, 2 or 1 nucleotides that are copied from a target nucleic acid. Of course extended probes can be any length within or outside of the ranges set forth above.

It will be understood that probes used in a method, composition or apparatus set forth herein need not be nucleic acids. Other molecules can be used such as proteins, carbohydrates, small molecules, particles or the like. Probes can be a combination of a nucleic acid component (e.g having a barcode, primer binding site, cleavage site and/or other sequence element set forth herein) and another moiety (e.g. a moiety that captures or modifies a target nucleic acid).

A method of the present disclosure can further include a step of removing one or more extended probes from a bead. In particular embodiments, the probes will have included a cleavage site such that the product of extending the probes will also include the cleavage site. Alternatively, a cleavage site can be introduced into a probe during a modification step. For example a cleavage site can be introduced into an extended probe during the extension step.

Exemplary cleavage sites include, but are not limited to, moieties that are susceptible to a chemical, enzymatic or physical process that results in bond breakage. For example, the location can be a nucleotide sequence that is recognized by an endonuclease. Suitable endonucleases and their recognition sequences are well known in the art and in many cases are even commercially available (e.g. from New England Biolabs™, Beverley Mass.; ThermoFisher™, Waltham, Mass. or Sigma Aldrich™, St. Louis Mo.). A particularly useful endonuclease will break a bond in a nucleic acid strand at a site that is 3'-remote to its binding site in the nucleic acid, examples of which include Type II or Type I is restriction endonucleases. In some embodiments an endonuclease will cut only one strand in a duplex nucleic acid (e.g. a nicking enzyme). Examples of endonucleases that cleave only one strand include Nt.BstNBI and Nt.Alwl.

In some embodiments, a cleavage site is an abasic site or a nucleotide that has a base that is susceptible to being removed to create an abasic site. Examples of nucleotides that are susceptible to being removed to form an abasic site include uracil and 8-oxo-guanine. Abasic sites can be created by hydrolysis of nucleotide residues using chemical or enzymatic reagents. Once formed, abasic sites may be cleaved (e.g. by treatment with an endonuclease or other single-stranded cleaving enzyme, exposure to heat or alkali), providing a means for site-specific cleavage of a nucleic acid. An abasic site may be created at a uracil nucleotide on one strand of a nucleic acid. The enzyme uracil DNA glycosylase (UDG) may be used to remove the uracil base, generating an abasic site on the strand. The nucleic acid strand that has the abasic site may then be cleaved at the abasic site by treatment with endonuclease (e.g. EndoIV endonuclease, AP lyase, FPG glycosylase/AP lyase, EndoVIII glycosylase/AP lyase), heat or alkali. In a particular embodiment, the USER™ reagent available from New England Biolabs™ is used for the creation of a single nucleotide gap at a uracil base in a nucleic acid.

Abasic sites may also be generated at non-natural/modified deoxyribonucleotides other than uracil and cleaved in an analogous manner by treatment with endonuclease, heat or alkali. For example, 8-oxo-guanine can be converted to an abasic site by exposure to FPG glycosylase. Deoxyinosine can be converted to an abasic site by exposure to AlkA glycosylase. The abasic sites thus generated may then be cleaved, typically by treatment with a suitable endonuclease (e.g EndoIV or AP lyase).

Other examples of cleavage sites and methods that can be used to cleave nucleic acids are set forth, for example, in U.S. Pat. No. 7,960,120, which is incorporated herein by reference.

Modified nucleic acid probes (e.g. extended nucleic acid probes) that are released from a microbead can be pooled to form a fluidic mixture. The mixture can include, for example, at least 10, 100, $1\times10^3$, $1\times10^4$, $1\times10^5$, $1\times10^6$, $1\times10^7$, $1\times10^8$, $1\times10^9$ or more different modified probes. Alternatively or additionally, a fluidic mixture can include at most $1\times10^9$, $1\times10^8$, $1\times10^7$, $1\times10^6$, $1\times10^5$, $1\times10^4$, $1\times10^3$, 100, 10 or fewer different modified probes. The fluidic mixture can be manipulated to allow detection of the modified nucleic acid probes. For example, the modified nucleic acid probes can be separated spatially on a solid support (i.e. different from the microbead from which the nucleic acid probes were released after having been contacted with mammalian cell genomic DNA), or the probes can be separated temporally in a fluid stream.

Modified nucleic acid probes (e.g. extended nucleic acid probes) can be separated on a microbead in a capture or detection method commonly employed for microarray-based techniques or nucleic acid sequencing techniques such as those set forth previously and/or otherwise described herein. For example, modified probes can be attached to a microarray by hybridization to complementary nucleic acids. The modified probes can be attached to beads or to a flow cell surface and optionally amplified as is carried out in many nucleic acid sequencing platforms. Modified probes can be separated in a fluid stream using a microfluidic device, droplet manipulation device, or flow cytometer. Typically, detection is carried out on these separation devices, but detection is not necessary in all embodiments.

The number of bead-attached oligonucleotides present upon an individual bead can vary across a wide range, e.g., from tens to thousands, or millions, or more. Due to the genomic profiling nature of the instant disclosure, many capture oligonucleotides can be attached to an individual microbead (i.e., thousands, tens of thousands, or more, of oligonucleotides per individual microbead), provided that genomic DNA capture and amplification from a contacted cell is optimized. It is contemplated that optimization of the oligonucleotide-per-microbead metric can be readily performed by one of ordinary skill in the art.

It is further expressly contemplated that in addition to the above-described sequence features, oligonucleotides of the instant disclosure can possess any number of other art-recognized features while remaining within the scope of the instant disclosure.

Droplet Formation

Droplet formation can be performed by any art-recognized method. Exemplary methods of droplet formation include those set forth for microfluidic droplets/barcoded beads as implemented by Macosko et al. 2015's Drop-seq (see, e.g., Macosko et al. Cell. 161(5):1202-1214 [PMID: 26000488] and US Patent Application No. 2018/0030515) and 10× Genomics™, first-generation DNA technology ("GemCode™")(Zheng et al. Nat Biotechnol. 34(3): 303-11 [PMID: 26829319], including methods covered by several patents referenced elsewhere herein).

Sequencing Methods

Some of the methods and compositions provided herein employ methods of sequencing nucleic acids. A number of DNA sequencing techniques are known in the art, including fluorescence-based sequencing methodologies (See, e.g., Birren et al, Genome Analysis Analyzing DNA, 1, Cold Spring Harbor, N.Y., which is incorporated herein by reference in its entirety). In some embodiments, automated sequencing techniques understood in that art are utilized. In some embodiments, parallel sequencing of partitioned amplicons can be utilized (PCT Publication No WO2006084132, which is incorporated herein by reference in its entirety). In some embodiments, DNA sequencing is achieved by parallel oligonucleotide extension (See, e.g., U.S. Pat. Nos. 5,750,341; 6,306,597, which are incorporated herein by reference in their entireties). Additional examples of sequencing techniques include the Church polony technology (Mitra et al, 2003, Analytical Biochemistry 320, 55-65; Shendure et al, 2005 Science 309, 1728-1732; U.S. Pat. Nos. 6,432,360, 6,485,944, 6,511,803, which are incorporated by reference), the 454 picotiter pyrosequencing technology (Margulies et al, 2005 Nature 437, 376-380; US 20050130173, which are incorporated herein by reference in their entireties), the Solexa™ single base addition technology (Bennett et al, 2005, Pharmacogenomics, 6, 373-382; U.S. Pat. Nos. 6,787,308; 6,833,246, which are incorporated herein by reference in their entireties), the Lynx massively parallel signature sequencing technology (Brenner et al. (2000). Nat. Biotechnol. 18:630-634; U.S. Pat. Nos. 5,695, 934; 5,714,330, which are incorporated herein by reference in their entireties), and the Adessi PCR colony technology (Adessi et al. (2000). Nucleic Acid Res. 28, E87; WO 00018957, which are incorporated herein by reference in their entireties).

Next-generation sequencing (NGS) methods can be employed in certain aspects of the instant disclosure to obtain a high volume of sequence information (such as are particularly required to perform sequencing of bead-associated genomic DNA to useful genomic coverage following capture of genomic DNAs from treated single cells) in a highly efficient and cost effective manner. NGS methods share the common feature of massively parallel, high-throughput strategies, with the goal of lower costs in comparison to older sequencing methods (see, e.g., Voelkerding et al, Clinical Chem., 55: 641-658, 2009; MacLean et al, Nature Rev. Microbiol, 7-287-296; which are incorporated herein by reference in their entireties). NGS methods can be broadly divided into those that typically use template amplification and those that do not. Amplification-utilizing methods include pyrosequencing commercialized by Roche as the 454 technology platforms (e.g., GS 20 and GS FLX), the Solexa™ platform commercialized by Illumina™, and the Supported Oligonucleotide Ligation and Detection (SOLiD™) platform commercialized by Applied Biosystems. Non-amplification approaches, also known as single-molecule sequencing, are exemplified by the HeliScope™ platform commercialized by Helicos Biosciences™, SMRT™ sequencing commercialized by Pacific Biosciences™, and emerging platforms marketed by VisiGen™ and Oxford Nanopore Technologies™ Ltd.

In certain embodiments, droplet-based capture, amplification and next-gen sequencing is performed using processes and kits such as those described in e.g., WO 2018/075693, WO 2018071448, WO 2018/058073, WO 2018/049025, WO 2018/041749, WO 2018/041747, WO 2018/039338, WO 2018/037289, WO 2018/031631, WO 2018/017949, WO 2018/005691, WO 2017/192633, WO 2017/205691, WO 2017/205344, WO 2017/197343, WO 2017/197338, WO 2017/196728, WO 2017/192633, WO 2017/184776, WO 2017/151828, WO 2017/139690, WO 2017/138984, WO 2017/132291, WO 2017/124101, WO 2017/117358, WO 2017/096158, WO 2017/087910, WO 2017/075436, WO 2017/075294, WO 2017/070056, WO 2017/037657, WO 2017/037656, WO 2017/012544, WO 2017/004612, WO 2016/187256, WO 2016/187179, WO 2016/183029, WO 2016/149418, WO 2016/138148, WO 2016/137973, WO 2016/130578, WO 2016/115273, WO 2016/114970, WO 2016/069939, WO 2016/061416, WO 2015/200893, WO 2015/200893, WO 2015/200893, WO 2015/200871, WO 2015/200869, WO 2015/157567 and WO 2014/210353, of 10× Genomics™.

In pyrosequencing (U.S. Pat. Nos. 6,210,891; 6,258,568, which are incorporated herein by reference in their entireties), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa™/Illumina™ platform (Voelkerding et al, Clinical Chem., 55-641-658, 2009; MacLean et al, Nature Rev. Microbiol, 7:287-296; U.S. Pat. Nos. 6,833,246; 7,115,400; 6,969,488, which are incorporated herein by reference in their entireties), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluorophore and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLiD™ technology (Voelkerding et al, Clinical Chem., 55: 641-658, 2009; U.S. Pat. Nos. 5,912,148; and 6,130,073, which are incorporated herein by reference in their entireties) can initially involve fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD™ system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, nanopore sequencing is employed (see, e.g., Astier et al, J. Am. Chem. Soc. 2006 Feb. 8; 128(5): 1705-10, which is incorporated by reference). The theory behind nanopore sequencing has to do with what occurs when a nanopore is immersed in a conducting fluid and a potential (voltage) is applied across it. Under these conditions a slight electric current due to conduction of ions through the can be observed, and the amount of current is exceedingly sensitive to the size of the nanopore. As each base of a nucleic acid passes through the nanopore (or as individual nucleotides pass through the nanopore in the case of exonuclease-based techniques), this causes a change in the magnitude of the current through the nanopore that is distinct for each of the four bases, thereby allowing the sequence of the DNA molecule to be determined.

The Ion Torrent™ technology is a method of DNA sequencing based on the detection of hydrogen ions that are released during the polymerization of DNA (see, e.g., Science 327(5970): 1190 (2010); U.S. Pat. Appl. Pub. Nos. 20090026082, 20090127589, 20100301398, 20100197507, 20100188073, and 20100137143, which are incorporated herein by reference in their entireties). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per base accuracy of the Ion Torrent sequencer is approximately 99.6% for 50 base reads, with approximately 100 Mb generated per run. The read-length is 100 base pairs. The accuracy for homopolymer repeats of 5 repeats in length is approximately 98%. The benefits of ion semiconductor sequencing are rapid sequencing speed and low upfront and operating costs.

Haplotype Phasing and Identification of Recombination Events and Aneuploidy Events Haplotype phasing of genomic sequence data and identification of recombination events within genomic DNA sequence can be performed by any method known in the art. The instant examples describe identification of whole-chromosome length haplotypes, identification of recombination events, and identification of aneuploidy events, using software packages including Picard [Broad], GATK [Broad], bwa-mem [Broad], Drop-seq tools Macosko et al. Cell. 161(5):1202-1214 [PMID: 26000488], Genome STRiP [Broad; Handsaker et al. Nat Genet. 47(3):296-303 PMID: 25621458], and HapCUT (Bioinformatics (Oxford, England); 2008 Aug. 15; 24(16) i153-9 [PMID: 18689818] and Selvaraj et al. Nat Biotechnol. 31(12):1111-8 [PMID: 24185094]).

Kits

The instant disclosure also provides kits containing agents of this disclosure for use in the methods of the present disclosure. Kits of the instant disclosure may include one or more containers comprising an agent (e.g., β-mercaptoethanol, heparin, salt buffer, heparinase, amplification reagents, sequencing reagents) and/or composition (e.g., oligonucleotide-presenting microbeads, a microfluidic droplet formation apparatus, etc.) of this disclosure. In some embodiments, the kits further include instructions for use in accordance with the methods of this disclosure. In some embodiments, these instructions comprise a description of administration of the agent to diagnose, e.g., aneuploidy (and optionally idiopathic infertility) in an individual from which a tested cellular sample derives. In some embodiments, the instructions comprise a description of how to treat an input population of mammalian cells to obtain decondensed genomic DNA that remains sufficiently cellularly/nuclearly encapsulated to perform microfluidic sorting upon a population of such treated mammalian cells to sort individual cells/nuclei into individual droplets (together with associated oligonucleotide-presenting microbeads).

The instructions generally include information as to concentrations of reagents, duration of treatment, etc., for the intended use. Instructions supplied in the kits of the instant disclosure are typically written instructions on a label or package insert (e.g., a paper sheet included in the kit), but machine-readable instructions (e.g., instructions carried on a magnetic or optical storage disk) are also acceptable.

The label or package insert can indicate that the composition is used for obtaining single-cell genomic DNA sequence from a cellular population. Instructions may be provided for practicing any of the methods described herein.

The kits of this disclosure are in suitable packaging. Suitable packaging includes, but is not limited to, vials, bottles, jars, flexible packaging (e.g., sealed Mylar™ or plastic bags), and the like.

Kits may optionally provide additional components such as buffers and interpretive information. Normally, the kit comprises a container and a label or package insert(s) on or associated with the container.

REFERENCES

Bansal, V. & Bafna, V. HapCUT: an efficient and accurate algorithm for the haplotype assembly problem. *Bioinformatics* 24, i153-9 (2008). [PMID: 18689818]

Handsaker, R. E. et al. Large multiallelic copy number variations in humans. *Nat Genet* 47, 296303 (2015). [PMID: 25621458]

Kirkness, E. F. et al. Sequencing of isolated sperm cells for direct haplotyping of a human genome. *Genome Res* 23, 826-32 (2013). [PMID: 23282328]

Lu, S. et al. Probing meiotic recombination and aneuploidy of single sperm cells by whole-genome sequencing. *Science* 338, 1627-30 (2012). [PMID: 23258895]

Macosko, E. Z. et al. Highly Parallel Genome-wide Expression Profiling of Individual Cells Using Nanoliter Droplets. *Cell* 161, 1202-14 (2015). [PMID: 26000488]

Montag, M., Tok, V., Liow, S. L., Bongso, A. & Ng, S. C. In vitro decondensation of mammalian sperm and subsequent formation of pronuclei-like structures for micromanipulation. *Mol Reprod Dev* 33, 338-46 (1992). [PMID: 1449801]

Samocha-Bone, D. et al. In-vitro human spermatozoa nuclear decondensation assessed by flow cytometry. *Mol Hum Reprod* 4, 133-7 (1998). [PMID: 9542970]

Selvaraj, S., J, R. D., Bansal, V. & Ren, B. Whole-genome haplotype reconstruction using proximity-ligation and shotgun sequencing. *Nat Biotechnol* 31, 1111-8 (2013). [PMID: 24185094]

Wang, J., Fan, H. C., Behr, B. & Quake, S. R. Genome-wide single-cell analysis of recombination activity and de novo mutation rates in human sperm. *Cell* 150, 402-12 (2012). [PMID: 22817899]

Zheng, G. X. et al. Haplotyping germline and cancer genomes with high-throughput linked-read sequencing. *Nat. Biotechnol* 34, 303-11 (2016). [PMID: 26829319]

The practice of the present disclosure employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, Molecular Cloning (Cold Spring Harbor Laboratory Press, Cold Spring Harbor, N.Y.); Sambrook et al., 1989, Molecular Cloning, 2nd Ed. (Cold Spring Harbor Laboratory Press, Cold Spring Harbor, N.Y.); Sambrook and Russell, 2001, Molecular Cloning 3rd Ed. (Cold Spring Harbor Laboratory Press, Cold Spring Harbor, N.Y.); Ausubel et al., 1992), Current Protocols in Molecular Biology (John Wiley & Sons, including periodic updates); Glover, 1985, DNA Cloning (IRL Press, Oxford); Anand, 1992; Guthrie and Fink, 1991; Harlow and Lane, 1988, Antibodies, (Cold Spring Harbor Laboratory Press, Cold Spring Harbor, N.Y.); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986); Westerfield, M., The zebrafish book. A guide for the laboratory use of zebrafish (*Danio rerio*), (4th Ed., Univ. of Oregon Press, Eugene, 2000).

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Reference will now be made in detail to exemplary embodiments of the disclosure. While the disclosure will be described in conjunction with the exemplary embodiments, it will be understood that it is not intended to limit the disclosure to those embodiments. To the contrary, it is intended to cover alternatives, modifications, and equivalents as may be included within the spirit and scope of the disclosure as defined by the appended claims. Standard techniques well known in the art or the techniques specifically described below were utilized.

EXAMPLES

Example 1: Materials and Methods

Preparation and Decondensation of Sperm Cells

Sperm was stored in cryopreservation buffer in liquid nitrogen. Sperm was first removed from liquid nitrogen and thawed at room temperature until liquid. Sperm was then washed by centrifuging for 10 minutes at 400 g at 4° Celsius, and the supernatant was removed. Sperm was resuspended in an equal volume of phosphate buffered saline, then spun again for 10 minutes at 400 g at 4° Celsius. The supernatant was again removed, and then sperm was concentrated by resuspending in ¼ previous buffer volume of cryoprotective buffer SMT (250 mM Sucrose, 5 mM $MgCl_2$, 10 mM Tris Cl pH 7.5). Sperm was then freeze-thawed by submerging the tube containing the sperm into liquid nitrogen, holding the tube at 37° Celsius until thawed, and repeating for a total of 3 freeze-thaw cycles. Freeze-thawed sperm was then diluted 1:10 with decondensation buffer (consisting of a salt buffer [113 mM KCl, 12.5 mM $KH_2PO_4$, 2.5 mM $MgCl_2$, 20 mM Tris Cl pH 7.5] supplemented at time of use with β-mercaptoethanol to a final concentration of 1 mM and heparin to a final concentration of 40.5 micrograms/mL). This sperm mixture was heated at 37° Celsius for 30 minutes, then placed at room temperature. Heparinase I treatment was then performed by adding 0.5 Units of heparinase I per 25 microliters of sperm mixture; this mixture was left at room temperature for 2 hours.

In-Droplet Amplification 10,000 sperm prepared as above were combined with a whole genome amplification mixture (for example, 10× Genomics™ V1 or 1× Themopol Detergent Free Buffer, 0.1725 mM dNTPs, 2 mM $MgCl_2$, 0.25% Pluronic F98, and 0.85 units SD polymerase detergent free). This master mix was combined with barcoded beads in a microfluidic device (either 10× Genomics™ V1 beads or beads conjugated to primers with a UV linker; primers sequenced GTGAGT-GATGGTTGAGGTAGTGTGGAGJJJJJJJJJKKK (SEQ ID NO: 9), where J is a random base consistent across all primers on the bead (produced by the above-described split-and-pool synthesis process, as is also known in the art), N is a random base in each primer, and K is either G or T randomly in each primer). Droplets were then treated with 365 nM UV light for 5 minutes (for beads with photocleavable linkers). Then whole-genome amplification was performed via thermal cycling (for reagents from 10×: 5 minutes at 98° Celsius followed by 17 cycles of [30 seconds at 4° Celsius, 1 second at 45° Celsius, 20 seconds at 70° Celsius, 30 seconds at 98° Celsius], followed by holding at 4° Celsius. For photocleavable primer beads: 3 minutes at 94° Celsius followed by 8 cycles of [45 seconds at 10° Celsius, 45 seconds at 20° Celsius, 45 seconds at 30° Celsius, 45 seconds at 40° Celsius, 45 seconds at 50° Celsius, 2 minutes at 65° Celsius, 20 seconds at 94° Celsius, 20 seconds at 48° Celsius], followed by holding at 4° Celsius). Product was extracted from droplets using reagents from 10× Genomics™ or by addition of perfluorooctanoic acid and centrifugation. If beads with photocleavable linkers were used, an intermediate PCR amplification of product extracted from droplets was performed by combining 20 µL of sample with 1× ThermoPol® buffer, 0.2 mM dNTPs, 0.3 µM primer corresponding to the non-random section of the bead primer, and 1 µL Deep Vent exo-DNA Polymerase in a total volume of 45 µL and thermal cycling (30 seconds at 94° Celsius followed by 12-18 cycles of [20 seconds at 94° Celsius, 20 seconds at 59° Celsius, and 3 minutes at 72° Celsius], followed by holding at 4° Celsius). Then, sequencing libraries could be prepared from product extracted from droplets and optionally further amplified as described by ligating sequencing adapters and further PCR amplification using reagents from 10× Genomics™, Illumina™'s Nextera™ XT, or NuGen™ Ovation™.

Example 2: Development of Droplet-Based Single-Sperm Sequencing ("Sperm-seq")

Droplet-based sequencing approaches that employ microbead-attached oligonucleotides for nucleic acid capture, such as those set forth in WO 2016/040476 (PCT/US2015/049178), as well as, e.g., in WO 2018/075693, WO 2017/139690 and WO 2017/096158, have been previously used with great success to obtain single-cell RNA expression data across a population of cells. Such droplet-based approaches act in both a scalable and cost-efficient manner, as compared, e.g., to plate-based expression profiling approaches. Droplet-based sequencing methods commonly rely upon introduction of an oligonucleotide-supplied "barcode" nucleic acid to amplicons produced from captured nucleic acids (e.g., captured poly-A-tailed RNAs), where the introduced barcode aids in identification of a single bead, droplet, and/or cell from whence an individual amplified sequence derived.

While such droplet-based oligonucleotide capture and sequencing approaches have been successfully employed with regularity to obtain single-cell RNA expression data across large populations of individual cells by employing barcoding and bead-based "next-gen" sequencing techniques, such approaches have not been readily adaptable to obtainment of genomic DNA sequences from single cells across a large population. Specific difficulties confronted in adapting such droplet-based approaches to obtaining single cell genomic DNA sequences across a large population of cells include the fact that genomic DNA is more densely packed, more highly protein-associated (wrapped around histones, etc.) and/or is encapsulated within the nucleus, as well as the fact that while poly-A-presenting mRNAs may be captured and amplified via approaches that employ poly-T-presenting capture oligonucleotides (where the common poly-T sequences of such capture oligonucleotides ultimately aid the specificity, efficiency and sequence diversity represented in massively parallel amplification of such captured poly-A-tailed mRNAs), capture oligonucleotides presenting a much broader array of sequences (optionally presenting random sequences) are the ones employed to achieve genome-wide capture of genomic DNA. Use of such a wide variety of capture sequences tends to create unique issues for representative amplification, with regard to generating useful barcoded amplicons for the next-gen sequencing approach that is ultimately employed.

With the goal of successfully assessing the genomes of thousands of individual sperm at one time in a scalable and affordable manner, development of a droplet-based approach to sperm genomic DNA capture and sequencing was initiated. In view of the above-noted difficulties encountered during prior attempts to adapt droplet-based sequencing techniques used for RNA capture and sequencing to obtain and assess single cell genomic DNA sequence, development of new technologies for performance of droplet-based single sperm genomic DNA capture and sequencing was initiated.

Extant droplet-based sequencing approaches offer the advantages of small reaction volumes and barcoded beads, and yet it was unclear how to effectively access a single cell's (e.g., a sperm cell's) genomic DNA while maintaining the single-cell identity of the cell's nucleus, so that the single-cell nuclear DNA could be individually delivered to a droplet also containing a bead, without also disrupting droplet structure and/or inactivating amplification reagents during the process of freeing genomic DNA for bead-based capture within the droplet. Thus, as shown in FIG. 1, adaptation of a droplet-based sequencing approach that labels each cell/bead with a cell/bead-specific barcode that is then also imparted to cellular genomic DNA-derived amplicons, was attempted.

Sperm are very hardy cells (having a thick, protective protein coat) with especially compacted genomes (e.g., a sperm nucleus is about ten-fold more compact than the nucleus of a somatic cell, at least in part reflecting that sperm genomes exchange histones for protamines that disulfide bond with each other). To achieve single cell droplet-based capture of sperm genomic DNA and subsequent high-throughput sequencing, a reliable method of accessing decondensed nuclear DNA from sperm, while retaining the single-cell character of each nucleus, was needed. Initially, extraction and decondensation of sperm genomic DNA was attempted using agents such as dithiothreitol (DTT) and harsh salts, yet such agents failed to provide sperm nuclei (e.g., such treatments tended to burst the nucleus) having decondensed genomic DNA that could then be introduced to droplets to achieve single cell bead capture and amplification in droplets, followed by next-gen sequencing. Exemplary unsuccessful attempts at accessing sperm genomic DNA in a droplet context included:

Enclosing sperm in agarose droplets and flowing in different lysis buffers (generally DTT-containing buffers).
Inclusion of heparin inhibited PCR (an issue only overcome via the heparinase treatment that has been employed in the later, successful decondensing protocols described herein).
Various amplification primer-related issues were confronted, prior to arriving at MALBAC primers and approaches as being the most capable of achieving genomic amplification of decondensed sperm genomes in droplets.

After such failures, a consideration was made regarding whether the human egg uses a milder approach for accessing sperm nuclear DNA that might be attempted for use in the current process.

Figure 2:
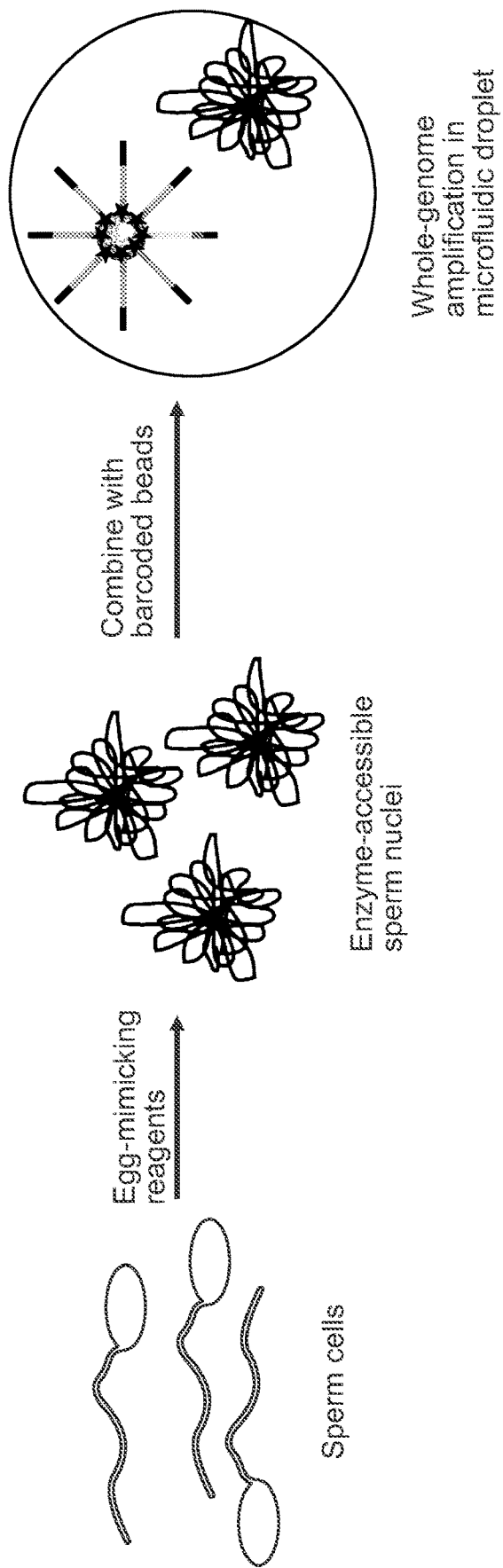
FIG. 2 shows a representative graphic of an effective approach of the instant disclosure to droplet-based single sperm cell genomic DNA capture and sequencing.

It was identified that reproductive biologists had previously described a process for decondensing sperm nuclear DNA for purpose of making it accessible for staining (e.g., FISH staining to detect aneuploidy; see Montag et al. Mol. Rep. and Dev. 1992; Samocha-Bone et al. Mol. Hum. Rep. 1998). The process involves first removing or cracking the sperm cell's protein coat, which the human oocyte achieves by performing an acrosome reaction during sperm docking to the egg membrane—such cracking can be achieved experimentally via rapid freeze-thaw cycles. The human egg then reduces the sperm genomic DNA's protamine disulfide bonds with glutathione and then accepts removed protamines, presumably via use of heparan sulfate—this disulfide reduction process and acceptance of removed protamines can also be achieved experimentally via administration of β-mercaptoethanol (for disulfide reduction) and heparin (for both reduction and acceptance processes). An attempt was then made to adapt such a sperm decondensation process to droplet-based sequencing of single sperm cells, as shown in FIG. 2.

The following process of decondensing sperm genomic DNA produced remarkably robust results in achieving retention of single-cell sperm nuclei that could be used in droplet-based single sperm nucleus genomic DNA capture, amplification and sequencing. First, rapid freeze-thawing was applied to a sample population of sperm cells, to crack the sperm's protein coat. β-mercaptoethanol and heparin were then administered in a salt buffer to the sperm cell population, and a heat treatment was applied, to remove the protamines that tightly pack sperm genomic DNA (as noted above, this decondensation method was adapted from the methods used in Montag et al. and Samocha-Bone et al.). Importantly, the sperm cell population was then heparinase treated to remove heparin, as heparin is a potent inhibitor of PCR.

Sperm cell nuclei were then individually delivered into individual droplets, together with individual microbeads that were coated with capture oligonucleotides harboring bead-specific barcode sequences, thereby creating a population of droplets within which a plurality of individual droplets contained both a single sperm cell nucleus and a single microbead. In-droplet bead-based nucleic acid capture and next-gen sequencing approaches have been extensively described previously, especially for capture of poly-A-tailed mRNAs (see, e.g., WO 2016/040476). In the instant process, bead-attached barcoded modified MALBAC primers were employed as capture oligonucleotides that allowed random annealing to genomic DNA, photocleavable linkers were used to attach the modified MALBAC primers to beads, and amplification was performed using slow-ramping temperature protocols (see, e.g., Zong et al. Science 338: 1622-6. [PMID 23258894], as well as WO 2012/166425, for MALBAC barcode handle sequence description and PCR/thermal cycling steps; it is noted, however, that no prior reference appears to have performed MALBAC in droplets and/or with photocleavable linkers, adding barcodes, optionally using a distinct polymerase, etc., as has been performed and/or described herein).

High-throughput sequencing was then performed upon barcoded amplicons obtained via droplet-based processes such as those described above. In particular, high-throughput single-sperm sequence was obtained from 20 individuals, with sequence from approximately 1000-2500 individual sperm cell libraries per individual obtained at a coverage of 1-2% of the genome of each sperm sequenced (a median of 13,000 heterozygous SNP sites as identified in an individual donor were therefore sequenced in each sperm). In sum, a total of 33,527 individual sperm were sequenced across 20 individuals, with a precise range of between 1,107 and 2,412 sperm sequenced per individual. While greater depth of genomic coverage for each sperm could technically have been obtained, the 1-2% coverage worked well for the haplotype-directed analyses of greatest interest, while also allowing for processing of a greater number of total cells—in particular, sufficient sequence across donor genome sites of heterozygosity was captured within each sperm to identify crossover events and determine chromosomal origin of sperm haplotypes.

Example 3: Analysis of Droplet-Based Single-Sperm Sequencing Data

Figure 3:
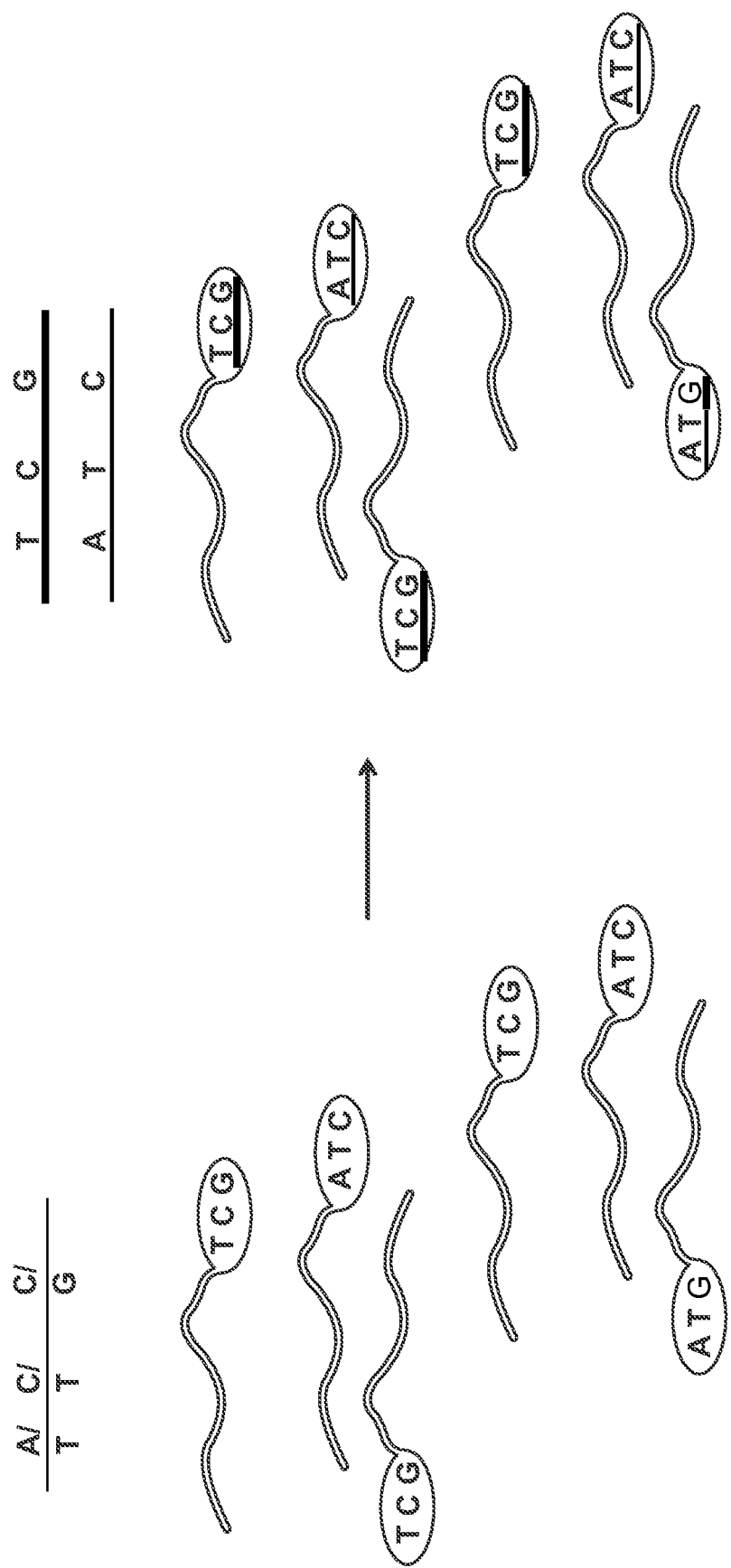
FIG. 3 shows a schematic approach for identifying whole chromosome phased haplotypes from single cell sequencing data (obtained via the processes of the instant disclosure).

As depicted in FIG. 3, whole chromosome phased haplotypes could be identified from single sperm sequence data obtained via the above-described "Sperm-seq" methods. In particular, the above-described Sperm-seq approach allowed for generation of whole genome sequencing (WGS) pooling data, which was then phased across all sites of heterozygosity. While genomic sequence of each donor was diploid (FIG. 3, left panel), sperm sequence should generally be haploid (on average/in theory), meaning that only variants deriving from one or the other chromosome of a donor should appear in each sperm sequence (indeed, if two alleles of a single heterozygous SNP are seen together in sequence of a single sperm, they were likely in cis in the donor genome). Resolution of donor haplotypes and identification of sites of crossover events occurring in individual sperm sequences were then performed upon the WGS data, via use of HapCUT software (Bansal & Bafna Bioinformatics 2008; Selvaraj et al Nat. Biotech. 2013) and an algorithm developed for sequencing read/hi-C data, which treated each cell as a "fragment" and tried to "break" as few fragments as possible in assigning haplotypes to sperm WGS sequence data (such haplotype phasing and identification of an exemplary sperm-based crossover event is depicted in the right-hand panel of FIG. 3). Thus, using Sperm-seq-derived sequence data, a completely phased version of the donor's genome (at chromosome scale) could be obtained, without using sequencing of a sperm donor's parents and/or relatives.

Figure 4:
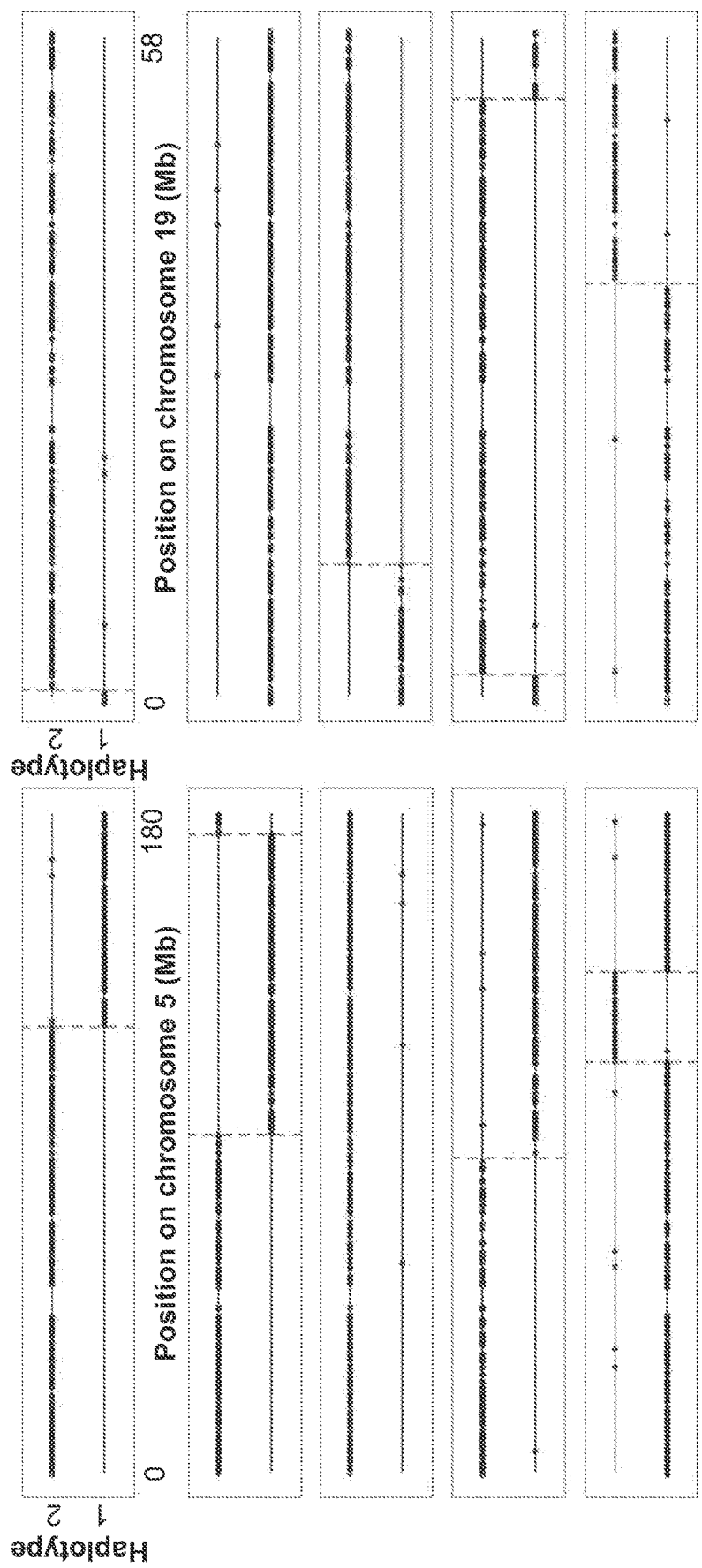
FIG. 4 shows chromosome-scale haplotype phasing, as enabled by the "Sperm-seq" processes of the instant disclosure (each plot corresponds to a single sperm cell, and all such single sperm cells shown derive from a single donor). At left, chromosome 5 from four sperm cells has been represented at chromosome scale, with crossover events determined and marked with dashed lines. At right, chromosome 19 from four sperm cells has been represented at chromosome scale, with crossover events determined and marked with dashed lines. Chromosome-length haplotype phasing enabled placement of individual sperm sequencing results onto haplotypes.

As shown in FIG. 4, identifying the haplotype of origin of each heterozygous SNP of each donor also enabled the identification of recombination events in each sperm cell. Notably, individual sperm cells of the same donor exhibited different numbers and locations of crossover events. The instant approaches and resultant sequence data therefore enabled determination of crossover events from large populations of individual cells, across a large number of individuals.

The total numbers of crossovers per sperm cell varied across the twenty (presumed healthy/likely fertile) donor individuals, exhibiting a Kruskal-Wallis $p<10^{-323}$ for the 851,678 total crossover events examined (FIG. 5), which is an observed effect that persisted even when cells were downsampled to include the same number of SNPs (FIG. 6), with downsampling performed to adjust for inter-donor differences in numbers of heterozygous SNP alleles available (which might otherwise therefore impact the ability to detect crossover events). For each individual donor, approximately 28,000 to 60,000 total crossover events were observed within the respective sperm cell populations examined. The median number of crossovers per cell on all autosomes ranged between 22 and 27 for each individual (it is noted that the median obtained in previous pedigree studies has generally been from about 25 to 27).

Figure 7:
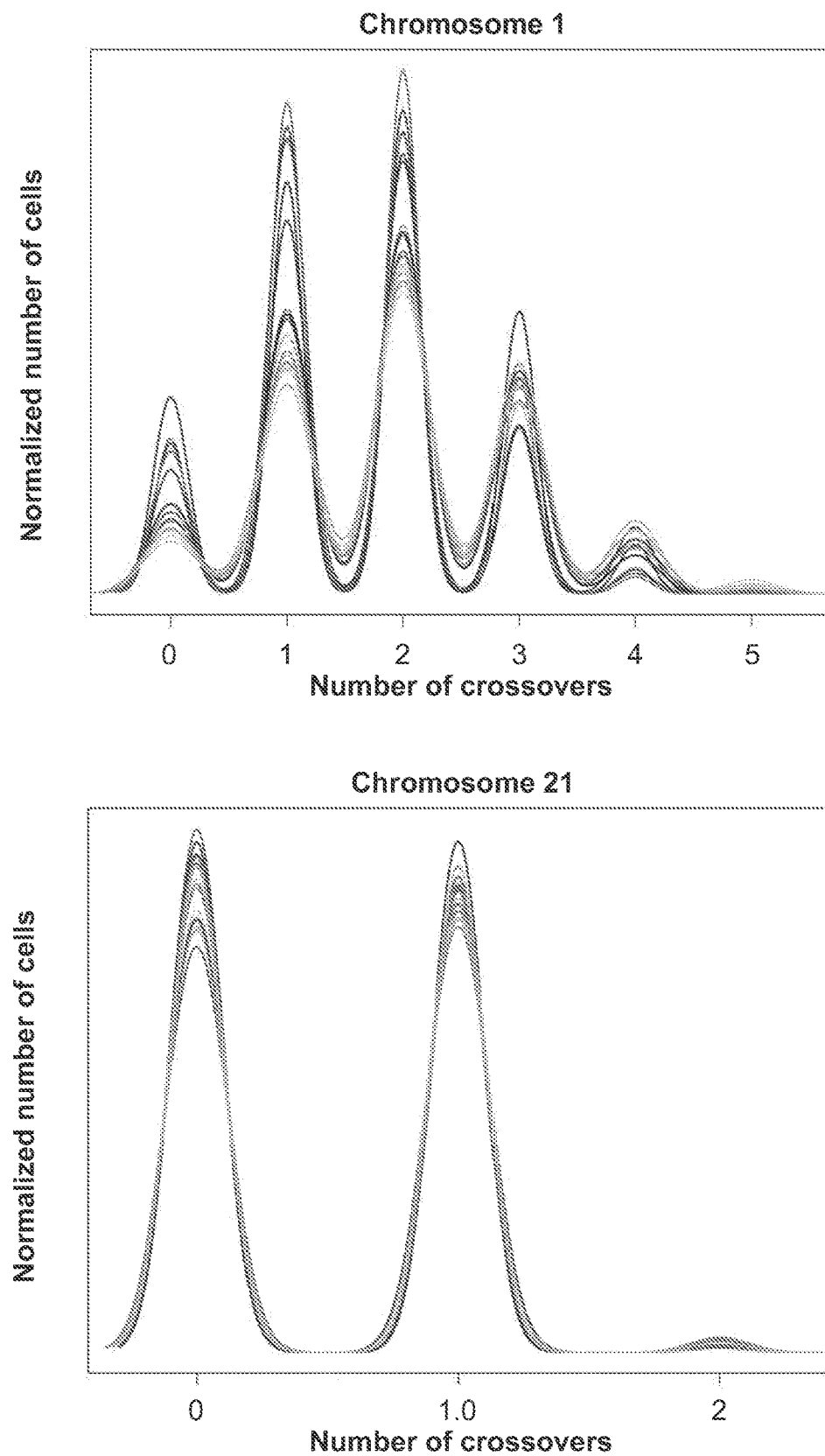
FIG. 7 shows aggregated crossover event count data for each individual donor, across both chromosome 1 (the longest human chromosome) and chromosome 21 (the shortest human chromosome). The number of crossovers per cell on chromosome 1 (top), and chromosome 21 (bottom) is shown for each individual. Individuals' crossover number distributions differed and have been plotted as lines colored by recombination rate: the bluest line represents the individual with the least mean crossovers per cell and the reddest line represents the individual with the most mean crossovers per cell. Inter-individual differences remained when controlling for differential SNP coverage.

The instant data set also provided enough crossover events to assess per chromosome patterns of crossover frequency. As shown in FIG. 7, the number of crossovers observed in chromosome 1 (the longest human chromosome) in sperm samples (as compared to donor haplotypes) tended to range from 0 to 4 events per cell, with five crossover events occurring infrequently in each individual; meanwhile, the number of crossovers observed in chromosome 21 (the shortest human chromosome) in sperm samples (as compared to donor haplotypes) tended to range from 0 to 1 event per cell, with two crossover events happening infrequently in each individual.

Figure 9:
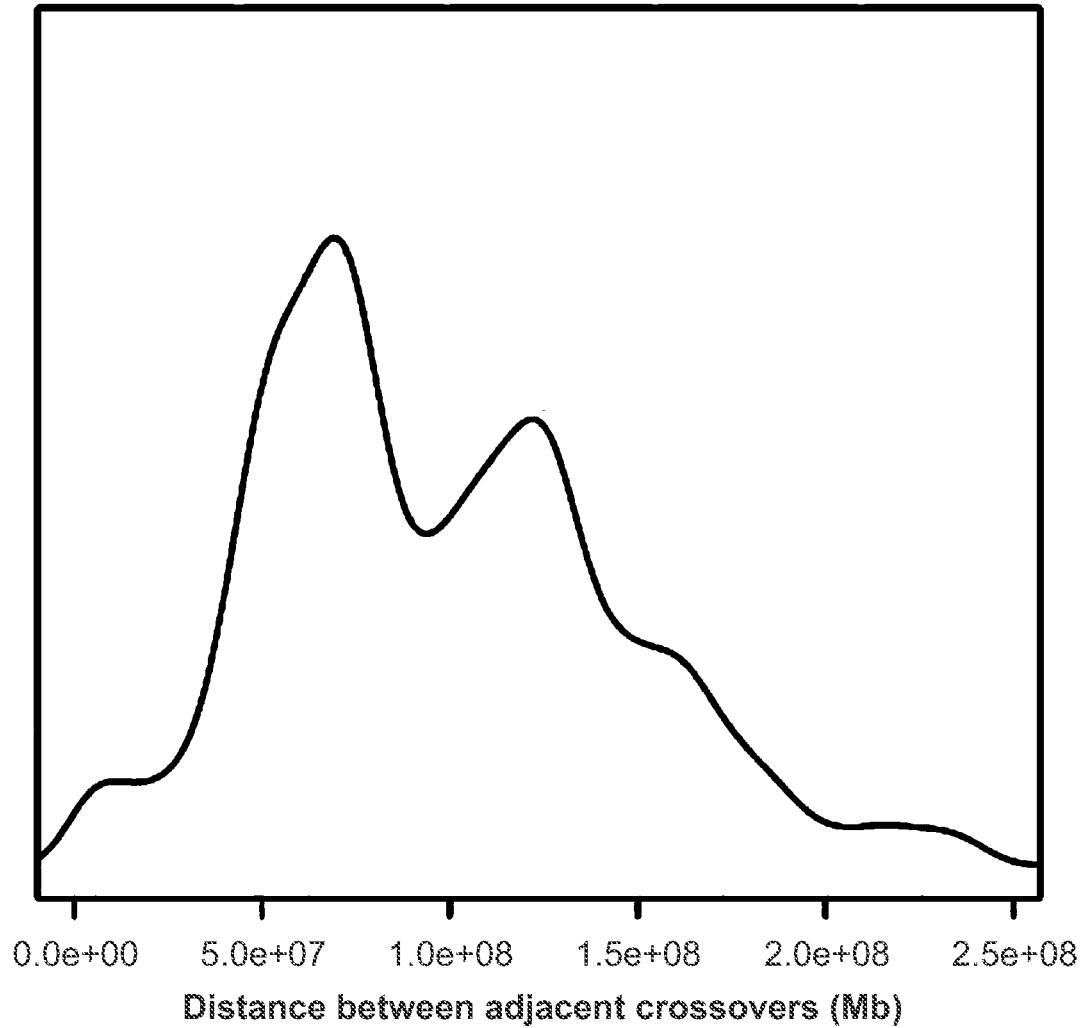
FIG. 9 shows crossover interference plotted for one male donor.
Figure 10:
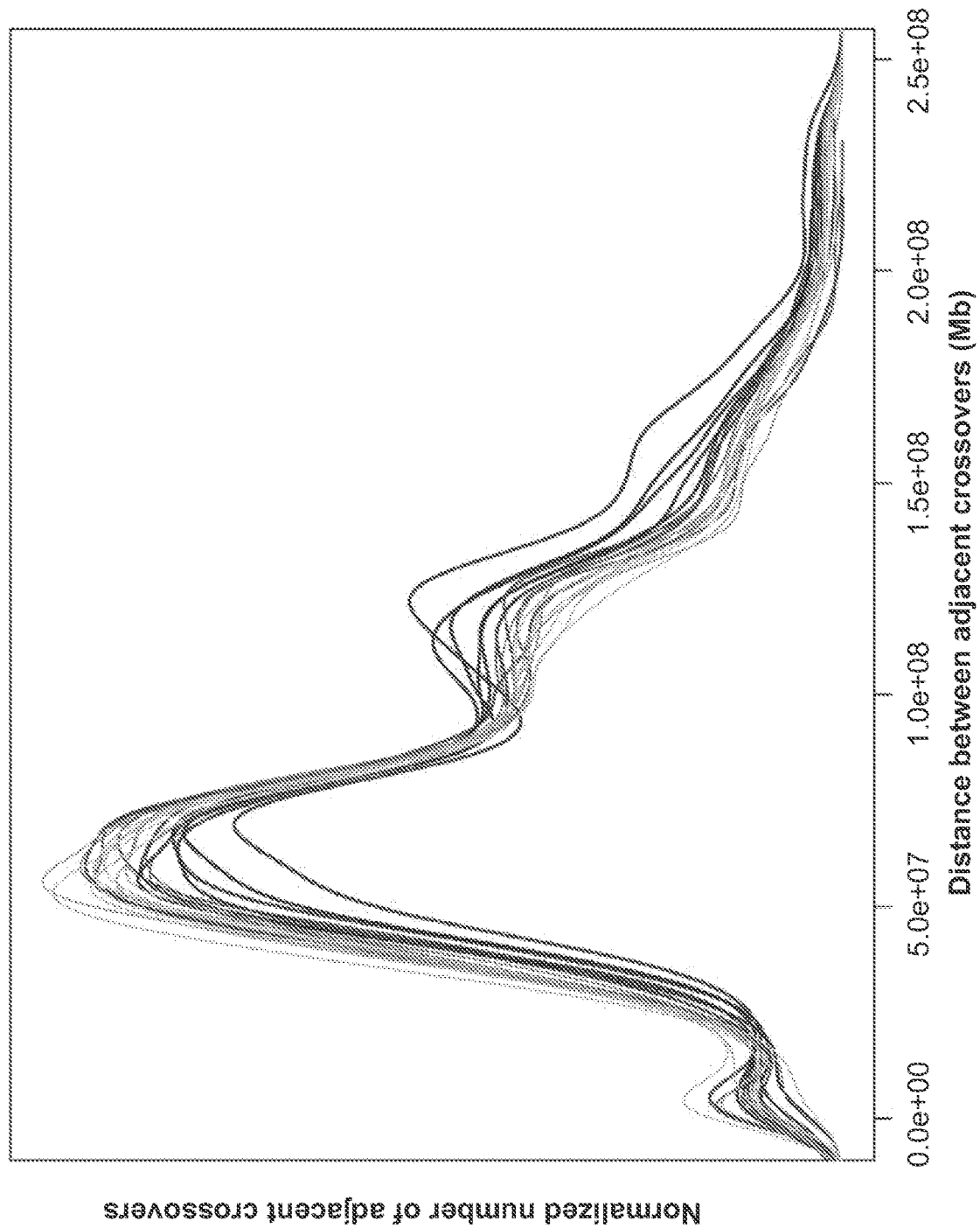
FIG. 10 shows that crossover interference differed among the individual male donors tested. In particular, a density plot of the above histograms was generated, and differences between donors were observed to remain when controlling for coverage of different numbers of SNPs across samples and cells. (Kruskal-Wallis $p<10^{-323}$).

In addition, the instant data set was used to provide insight into crossover interference. Crossover interference is the tendency of crossovers to occur farther apart than expected by chance. As shown in FIG. 8, the median distance between chromosome 7 crossover events was observed to be 73.4 Mb, which was determined to be a significantly greater distance than would have been predicted in the absence of crossover interference (random distributions of crossover events), with the observed occurrence of shorter distance crossover events relatively underrepresented relative to the random crossover model (in which median distance between adjacent crossovers was projected to be about 35 Mb). Thus, the distribution of distances between adjacent crossovers in the same cell was much larger than would be expected by chance in all 20 individuals (medians per individual 68-90 Mb, $p<<<10^{-4}$ in a permutation test randomly assigning crossovers to cells), which demonstrated crossover interference. The pattern of crossover interference differed among the 20 individuals (each line in FIG. 10 is the pattern from one individual colored as in FIG. 5; Kruskal-Wallis test $p<10^{-300}$). Between different individual male donors, crossover interference was observed to differ (FIG. 9 and FIG. 10) and was also highly negatively correlated with recombination rate (FIG. 11; Pearson's $R=-0.87$; $R^2=0.76$; $p=5.1\times10^{-7}$). Crossover interference (median distance) was observed to have correlated with crossover rate (median numbers of crossover events per cell); however, significant variation was also observed.

Figure 12:
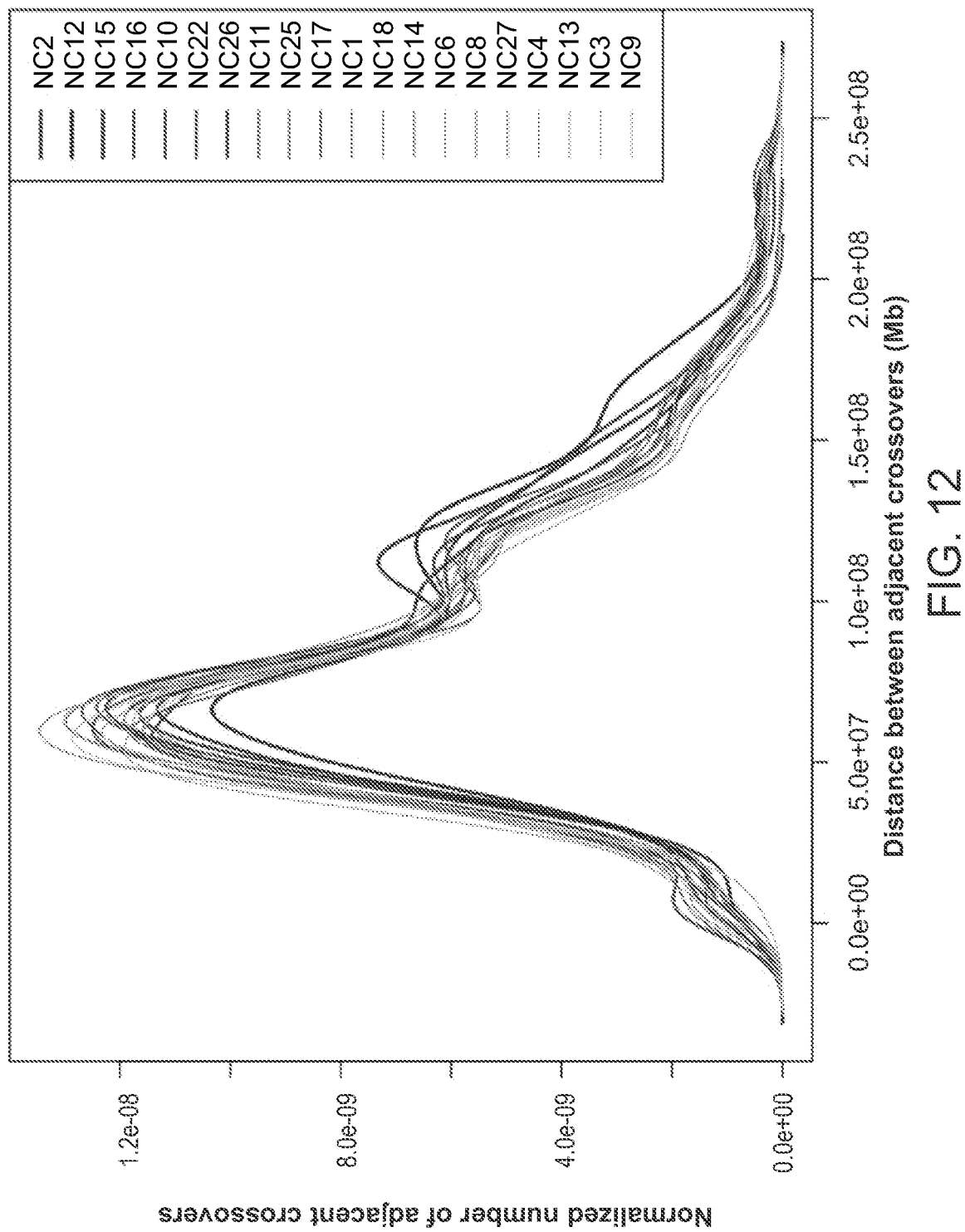
FIG. 12 shows that crossover interference varied even when recombination rate was held constant (Kruskal-Wallis $p<10^{-40}$).
Figure 13:
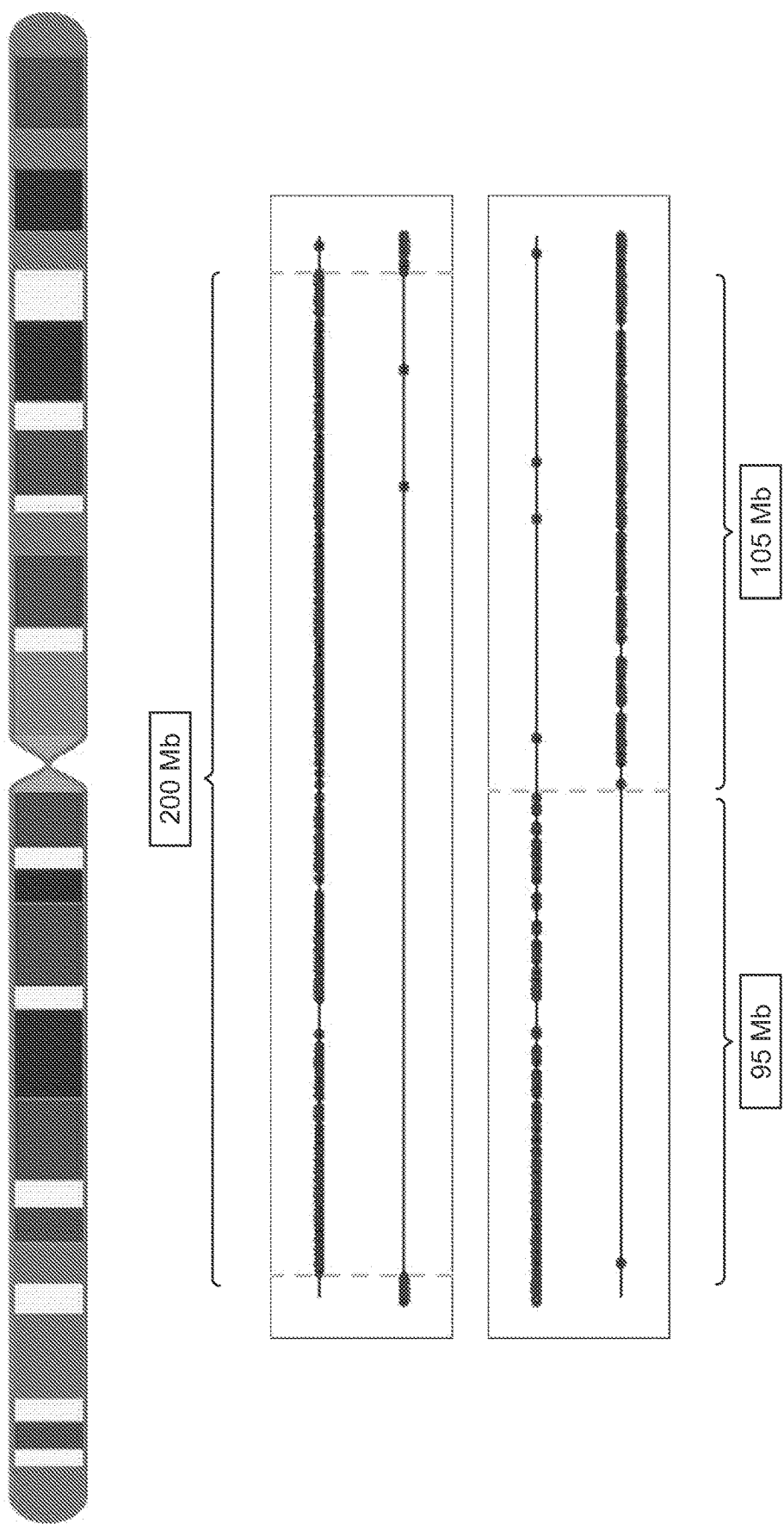
FIG. 13 shows that differential use of centers of large chromosomes for crossovers might explain the bimodality of adjacent crossover distances that were observed in the instant Sperm-seq data.
Figure 14:
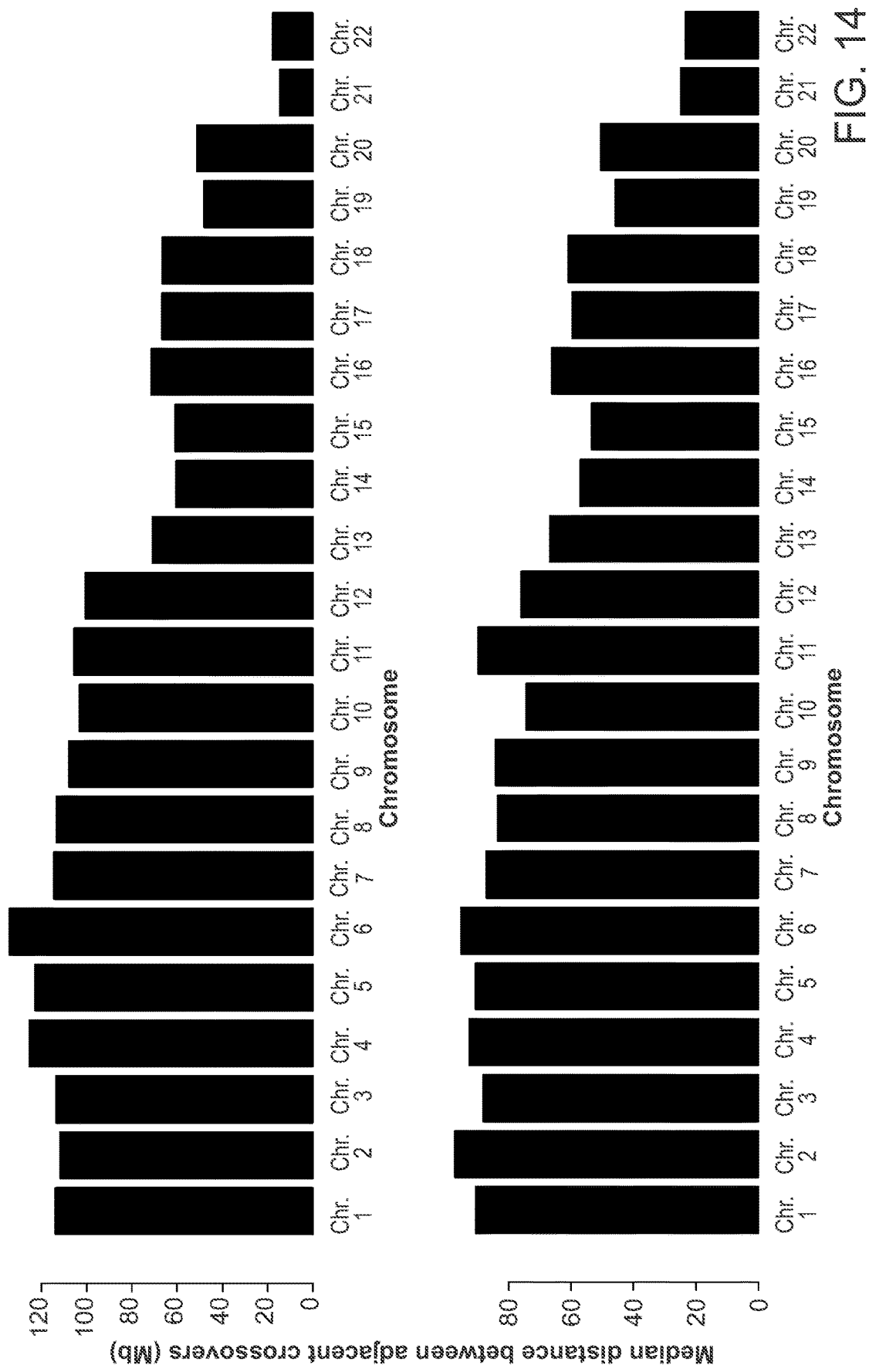
FIG. 14 shows a pair of bar graphs that present crossover interference across chromosome, with the top bar graph being from one individual donor and the bottom bar graph being from another individual donor (noting the differing y-axis scales).
Figure 15:
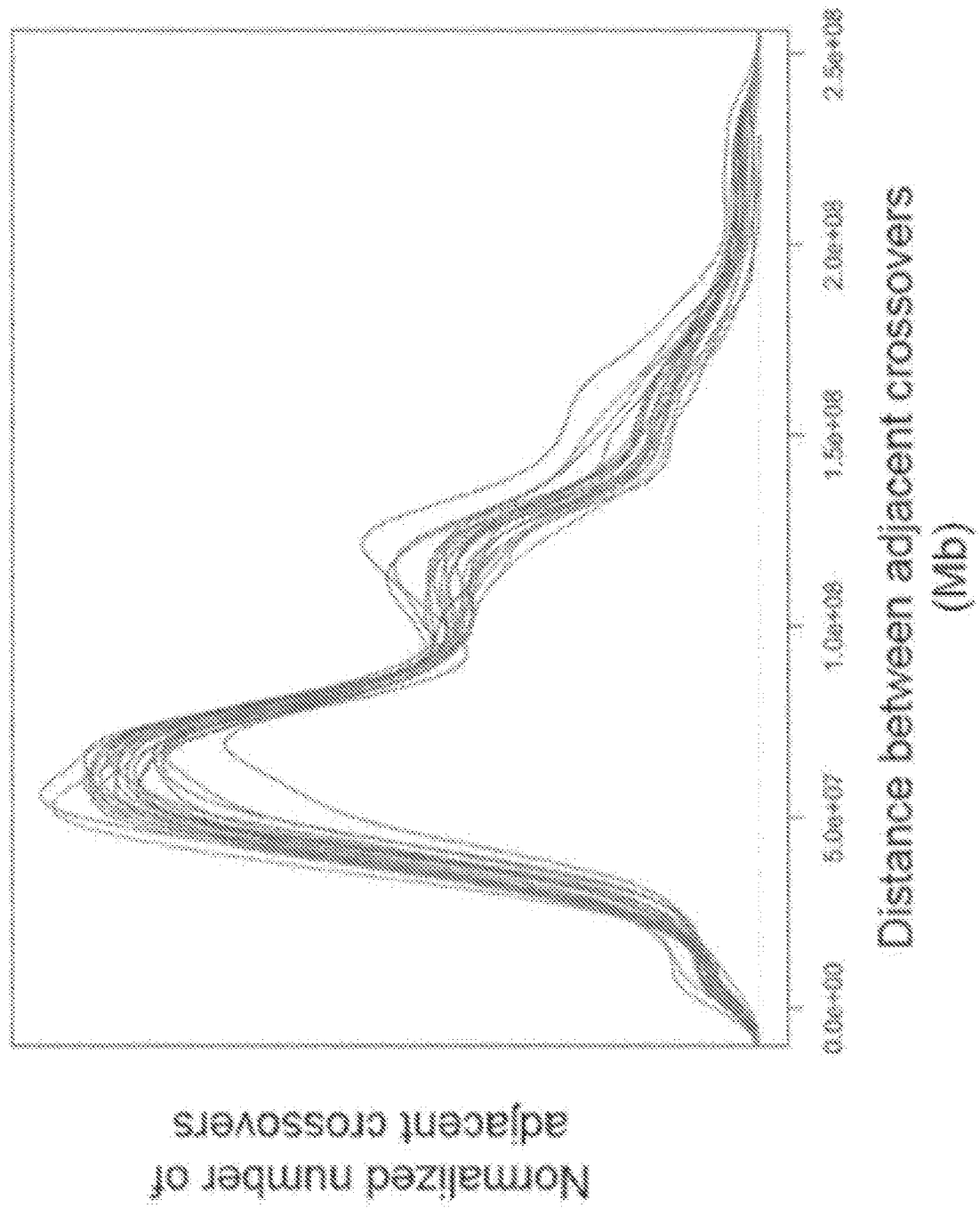
FIG. 15 shows that crossover interference differences among individual males persisted even when all cells were downsampled to have the same number of observed SNPs, with a Kruskal-Wallis $p<10^{-323}$.

Indeed, crossover interference varied even when the recombination rate was held constant (FIG. 12, 10% of cells with 26 crossovers examined, Kruskal-Wallis $p<10^{-40}$). When only cells that exhibited 26 crossovers were examined for crossover interference, crossover interference was identified to vary among individual male donors (FIG. 12). Differential use of centers of large chromosomes for crossovers also might explain the bimodality of adjacent crossover distances that were observed in the instant Sperm-seq data (FIG. 13). The single-sperm sequence data clearly established that crossover interference varied both across chromosomes of an individual donor, and between individual donors (FIG. 14), and this latter effect (crossover interference differing among individual male donors) remained even when all cells were downsampled to adjust for differing total SNP counts (FIG. 15). In such downscaling experiments, all crossovers were called from the same number of SNPs/chromosomes; 33,112 cells were included in such assessments (415 or 1.2% were dropped overall, while 6% of cells were dropped for the individual donor who exhibited the lowest SNP coverage).

Figure 16:
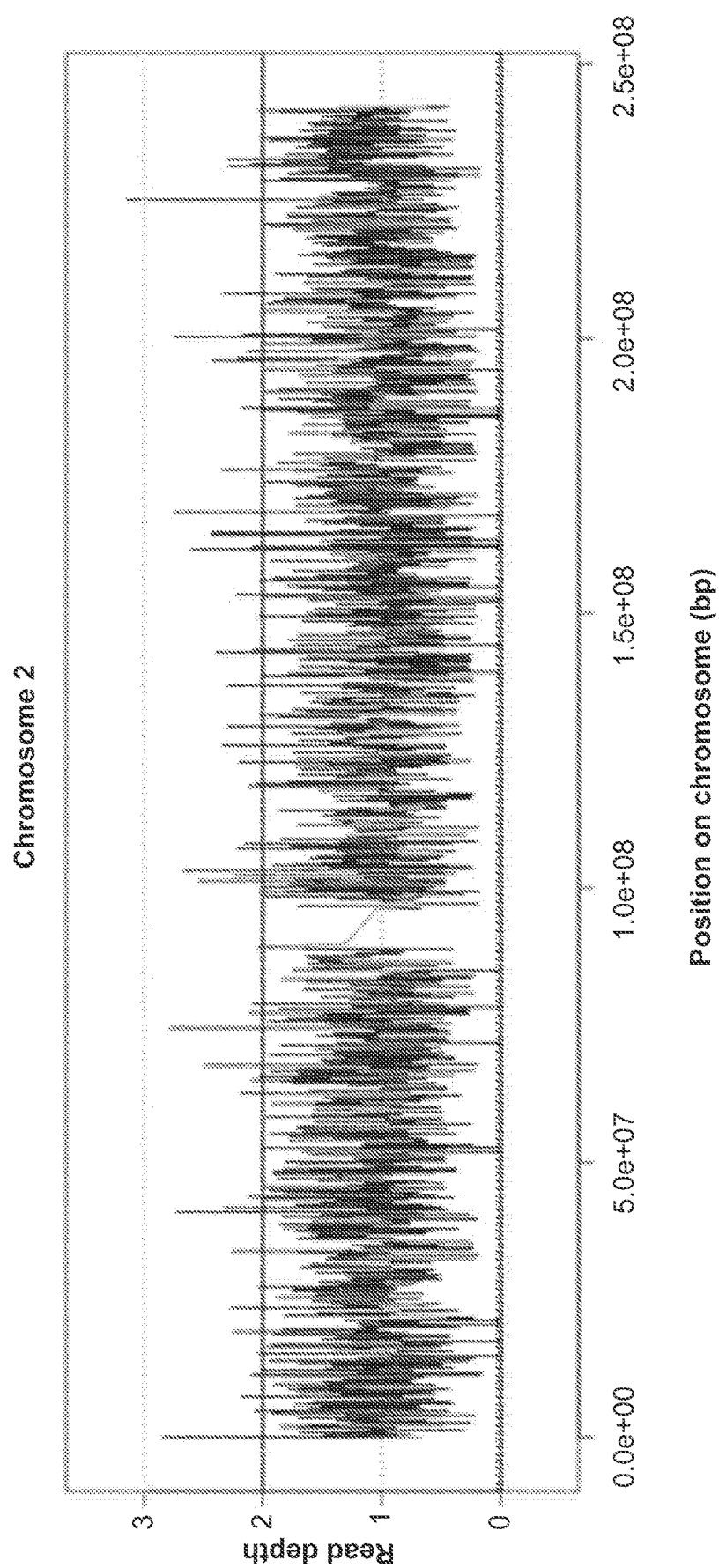
FIG. 16 shows data depicting the ploidy of chromosome 2 in one examined sperm cell, showing normal ploidy and demonstrating how ploidy can be inferred at each chromosome in each cell.
Figure 17:
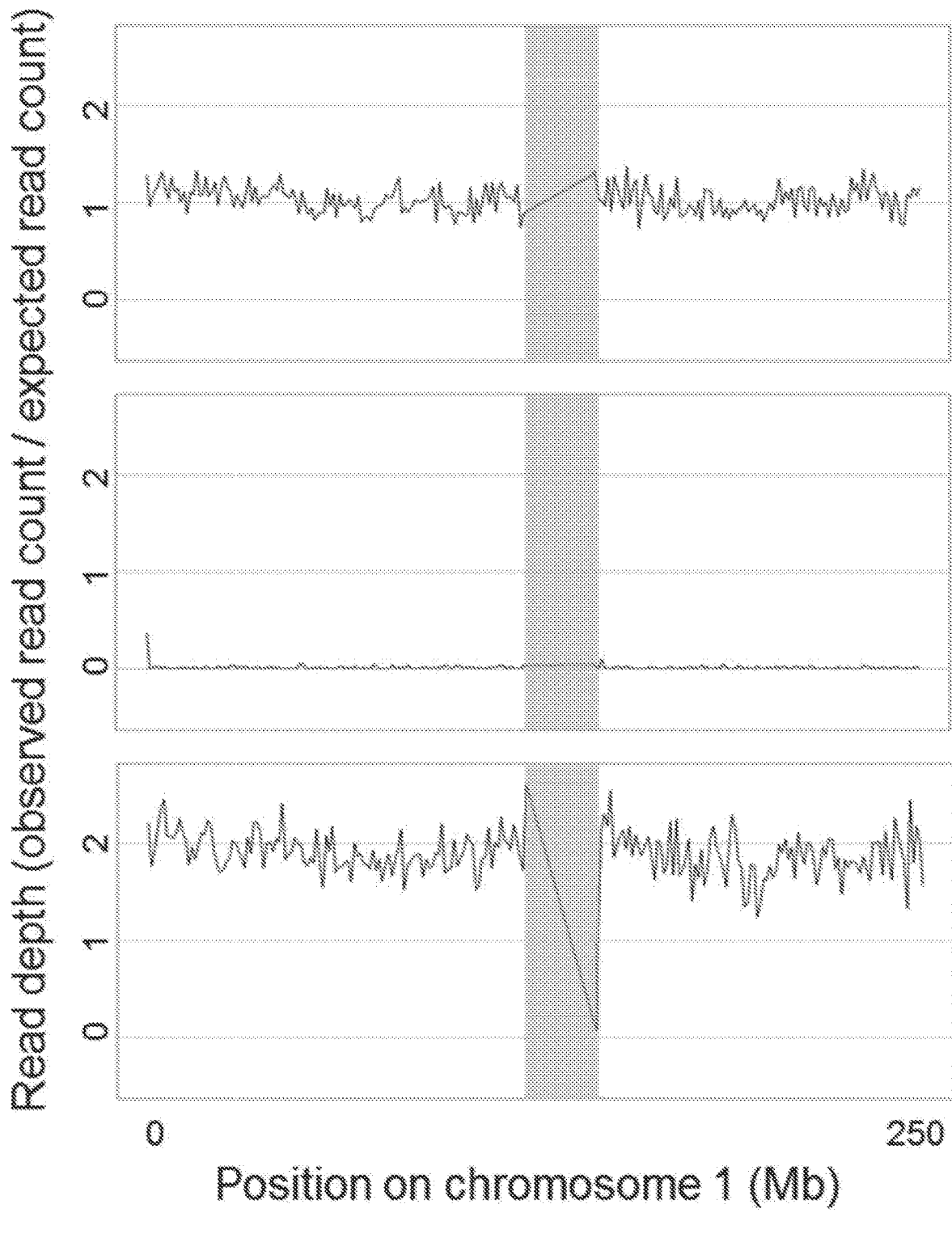
FIG. 17 shows read depth and the inferred ploidy results for a number of individual sperm across chromosome 1. These experiments revealed gains and losses of chromosomes when applied across the genome. Shown is an example sequence read depth across chromosome 1 for a cell with the expected observation of one copy of the chromosome (top), a cell with loss of the chromosome (middle), and a cell with an extra copy of the chromosome (bottom). Read depth has been plotted in 1 Mb bins as the number of observed reads in that bin divided by the number of reads expected in that bin based on library size and sequence context; a haploid read depth of 1 was expected at all chromosomes in sperm. Centromeres are located at gray rectangles. Aneuploidy occurred with variable frequency across sperm from all of the 20 individuals examined, with aneuploid cells typically comprising 0.5-3% of the total sperm population.

Perhaps most relevant to application of the current methods of the disclosure to diagnosis and analysis of male infertility, the sequence data of the instant disclosure enabled identification of single sperm cells that possessed alterations in chromosomal ploidy. In particular, normalized read depths were assessed across various chromosomes, with an expected value of 1 (for a haploid sperm genome) when read depths were calculated (see FIG. 16). However, in a number of individual sperm cells, cells possessing lost chromosomes and cells possessing an extra chromosome were also identified (FIG. 17 and FIG. 18).

Figure 19:
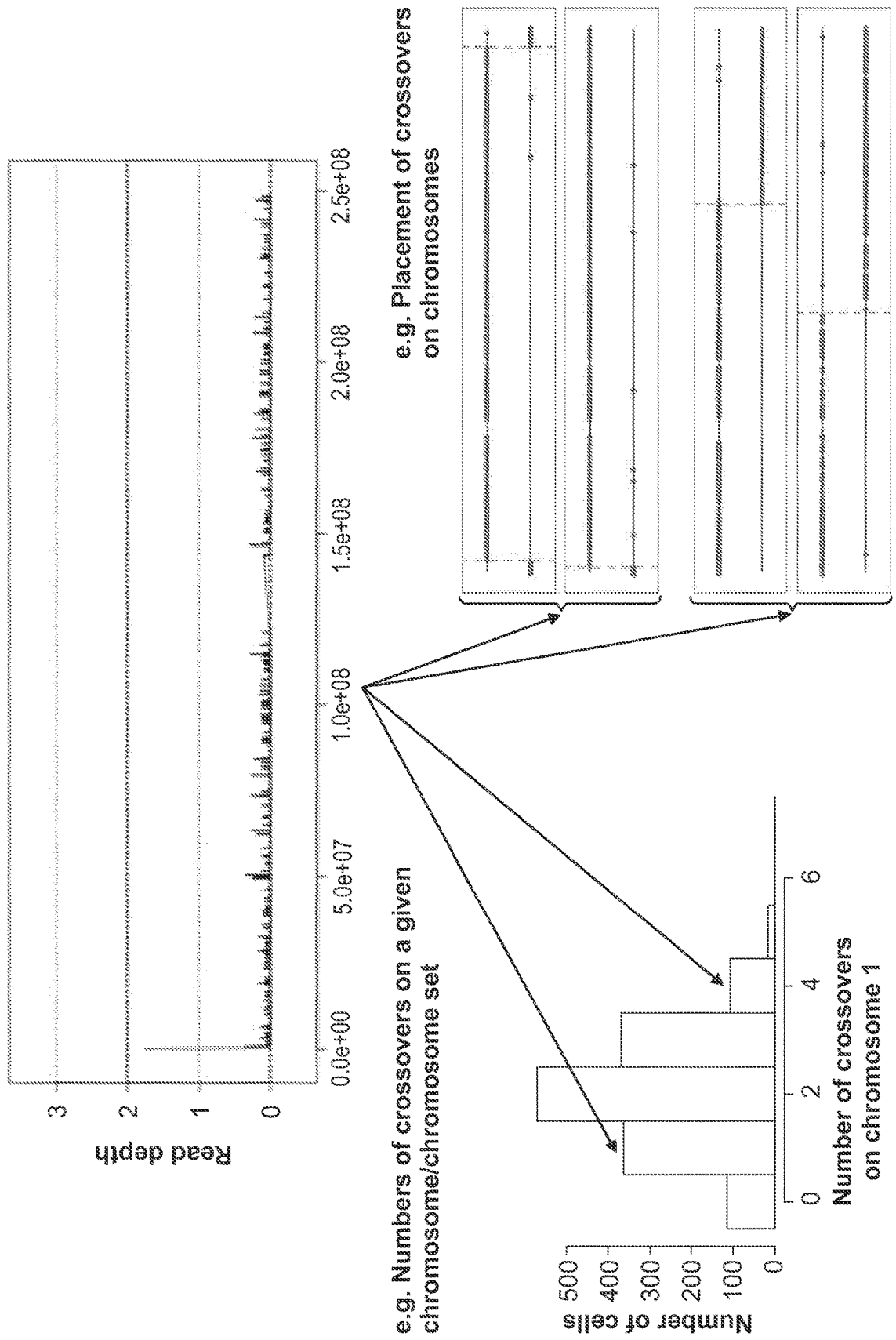
FIG. 19 shows that within-cell correlations may unmask meiotic relationships.
Figure 21:
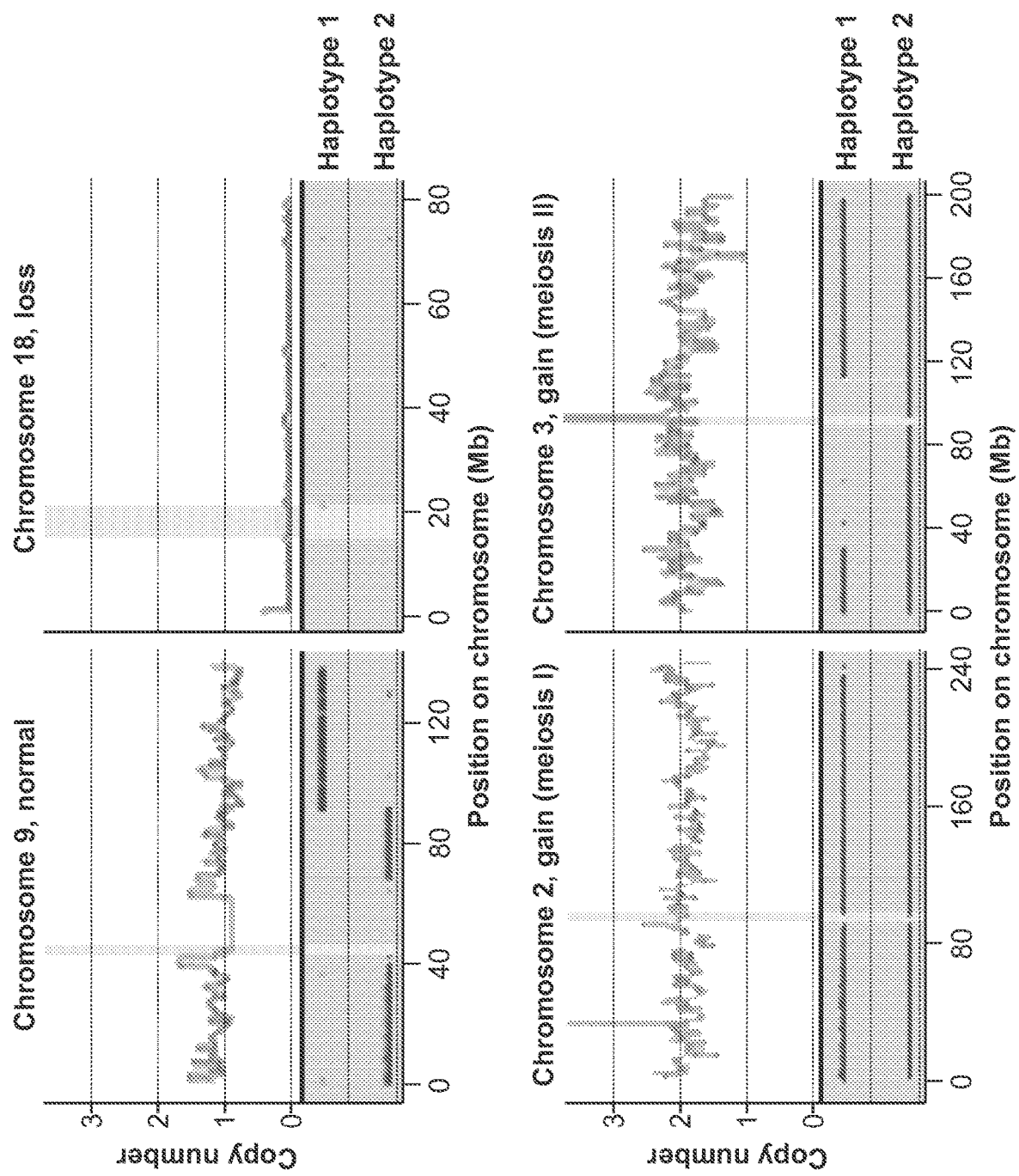
FIG. 21 shows aneuploidy detection examples. Example ploidy for normal and aneuploid chromosomes from different cells is presented (aneuploidy is detected as deviations from normal haploid copy number/depth of sequence coverage of 1). Copy number, thick gray line (1 Mb bins); observed heterozygous SNP alleles (blue dots); parental haplotype of origin (dashed blue lines in bottom blue region); centromeres, gray vertical boxes. Gains occurring during nondisjunction of homologs at meiosis I (MI) resulted in two chromosomes with different haplotypes at their centromere (see second panel from right). Gains occurring during nondisjunction of sister chromatids at meiosis II (MII) resulted in two chromosomes with identical haplotypes at their centromere (rightmost panel).

Additionally, where aneuploidy was observed, it was reasoned that within-cell correlations could unmask meiotic relationships—e.g., where something went wrong with crossover events (or there is a pattern and/or phenotype of interest), the current data could can be used to identify other such events (FIG. 19). It was reasoned likely that cells with aneuploidy would exhibit fewer crossovers elsewhere, and the current data have been further analyzed for numbers, patterns, etc., to see whether numbers and/or patterns of crossover events correlated or co-varied within the same cells, which could also suggest underlying biology. It was reasoned that failure of proper meiosis could likely cause genetically abnormal sperm and thus infertility. Indeed, various examples of aneuploidy detection were observed in the instant data set. As seen in FIG. 21, exemplary normal and aneuploid chromosomes from different cells were identified, with aneuploidy detected as deviations from normal haploid copy number/depth of sequence coverage of 1. Such examples included instances of gains that occurred during nondisjunction of homologs at meiosis I (MI), which resulted in two chromosomes possessing different haplotypes at their centromere (see FIG. 21, second panel from right). An example of gains occurring during nondisjunction of sister chromatids at meiosis II (MII) was also identified, which resulted in two chromosomes possessing identical haplotypes at their centromere (see FIG. 21, rightmost panel).

Figure 22A:
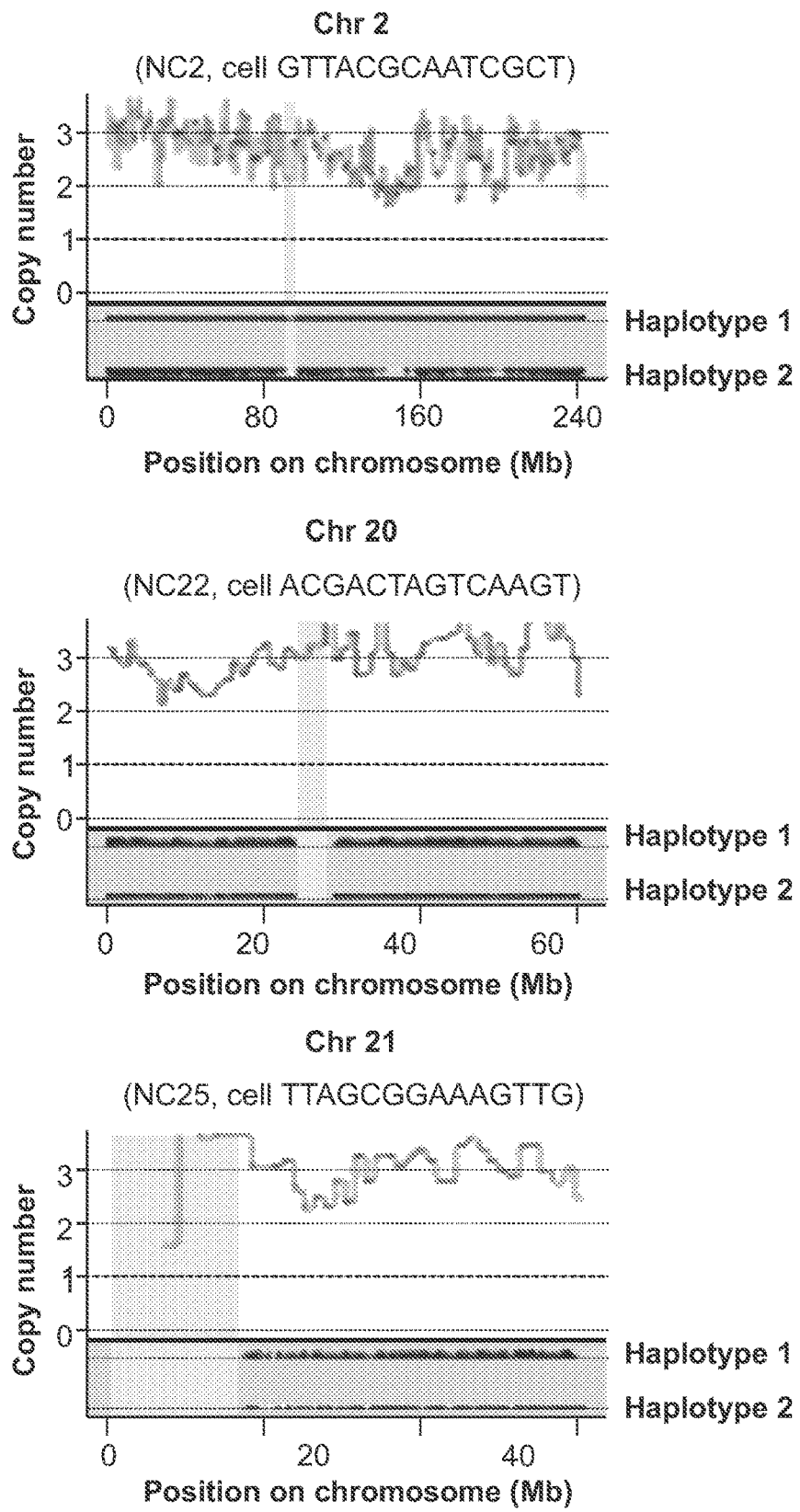
FIGS. 22A-22E show examples of non-canonical aneuploidy events detected with the "Sperm-seq" process of the instant disclosure. Copy number, SNPs, haplotypes, and centromeres (or centromeres and acrocentric arms) are plotted as in the FIG. 21 above.
Figure 22B:
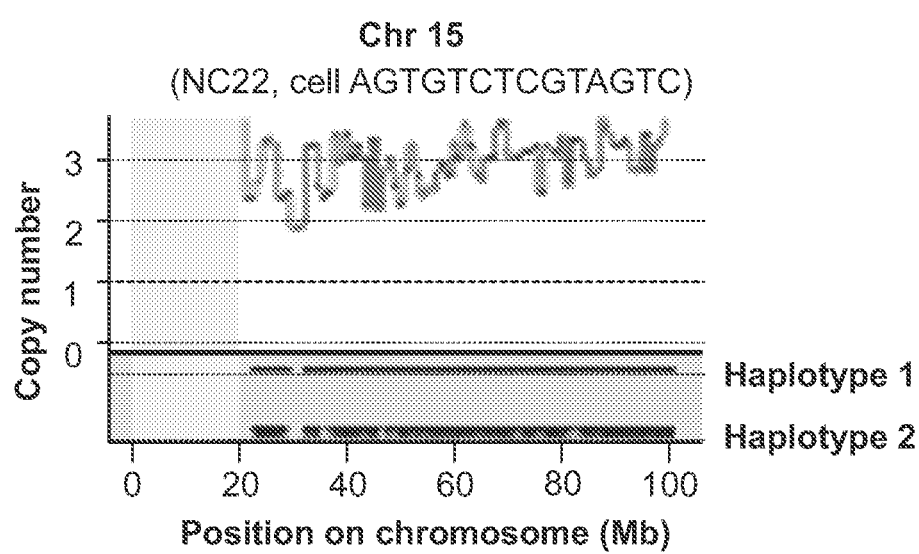
Figure 22C:
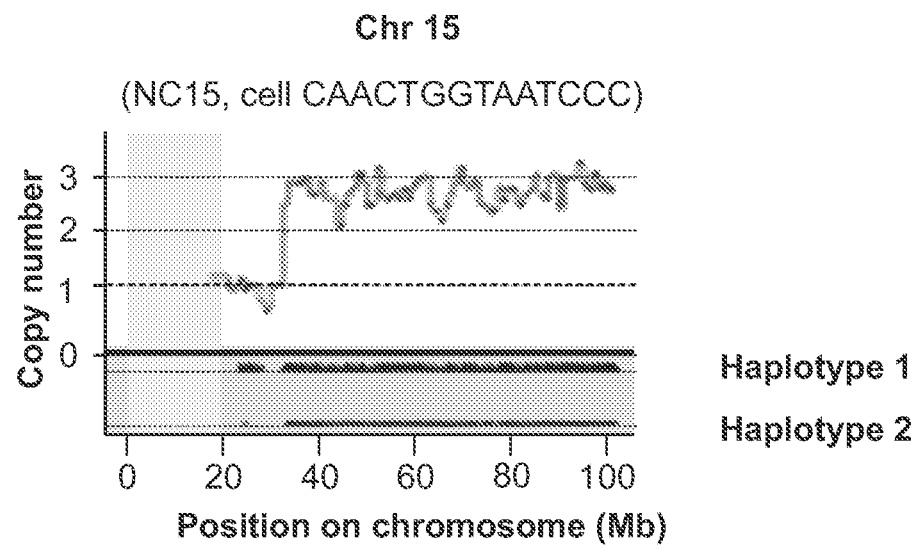
Figure 22D:
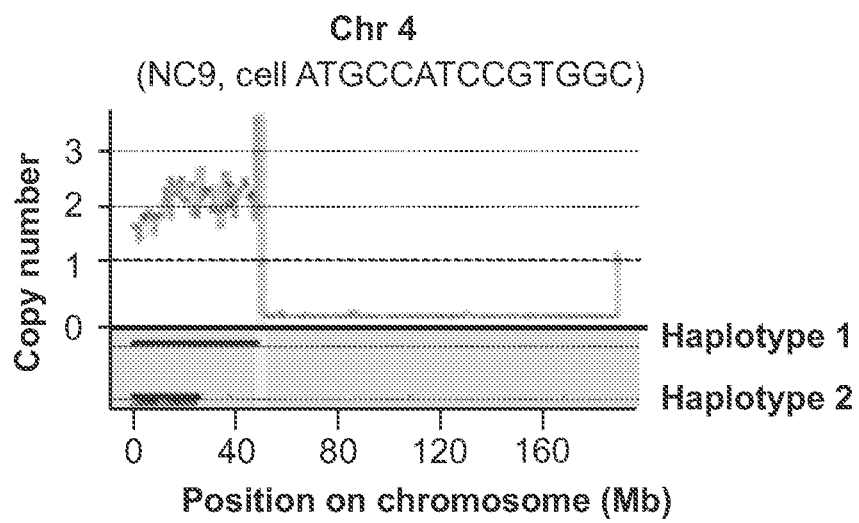
Figure 22E:
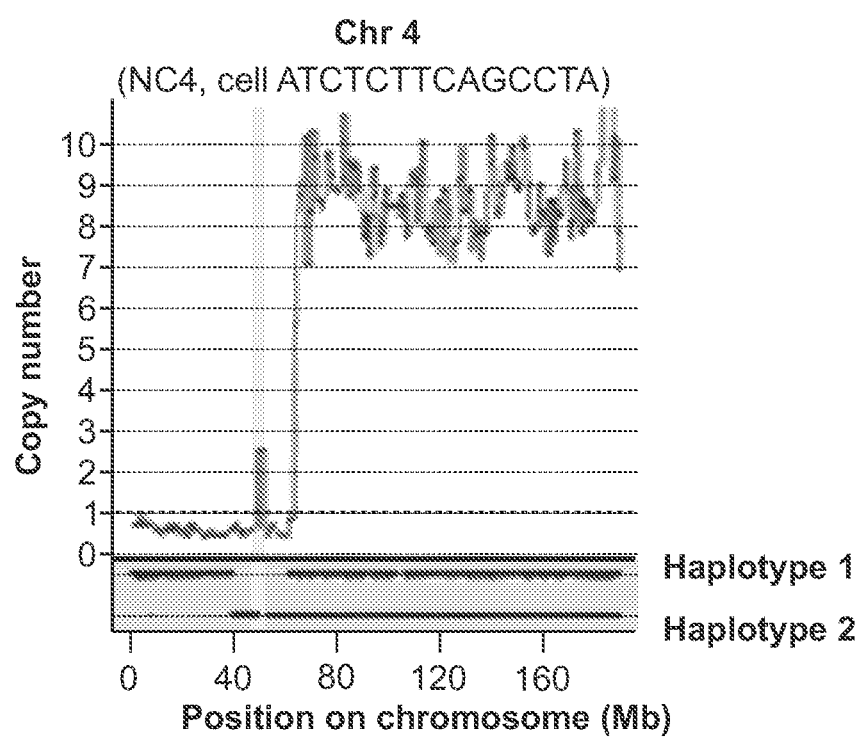

Examples of non-canonical aneuploidy events were also detected via the "Sperm-seq" process of the instant disclosure. In particular, examples where chromosomes 2, 20, 21, and 15, respectively, were sometimes present in an otherwise haploid sperm cell in three copies were each identified (FIGS. 22A and 22B). An example of a distinct triplication of chromosome 15, from ~33 Mb onwards, was also observed in cells from three donors (FIG. 22C shows exemplary data from one donor). An example of a compound gain of the p arm and loss of the q arm of chromosome 4 was also observed (FIG. 22D). In addition, an example of a many-copy (copy number is hard to precisely infer at high numbers) amplification of most of the q arm of chromosome 4 (~127 Mb) was also observed (FIG. 22E). Thus, the "Sperm-seq" methods of the instant disclosure were particularly robust in identifying a variety of different types of copy number variation across the individuals and total sperm numbers assessed (see FIG. 20 for a tabulated listing of sperm donor and single-sperm sequencing characteristics and results).

Because the methods and compositions of the instant disclosure can identify aneuploidy and/or meiotic failures at the single-sperm cell genomic level, clinical applications to aid in diagnosis and treatment of infertility are contemplated for the instant methods and compositions (where male partners of a couple experiencing infertility exhibit a normal sperm count, approximately 60% of such infertility cases are clinically attributed to the female; however, the remaining 40% of cases are described as idiopathic).

Figure 5:
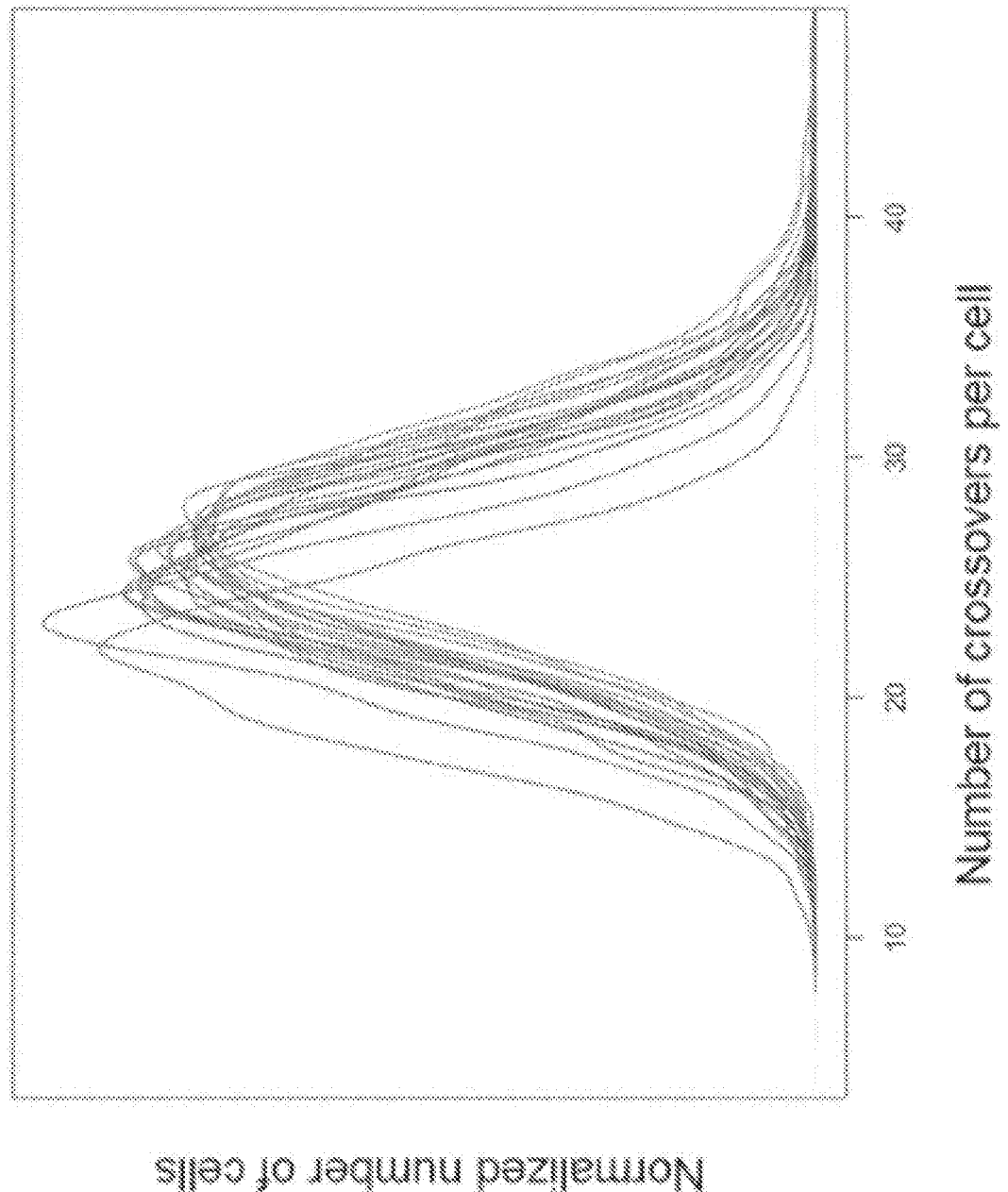
FIG. 5 shows that analysis of 851,678 crossover events identified using the instant "Sperm-seq" approach demonstrated that the total numbers of crossovers per sperm cell varied across the twenty donor individuals, exhibiting a Kruskal-Wallis $p<10^{-323}$. The number of crossovers per cell on all autosomes is shown for each individual. Individuals' crossover number distributions differed and have been plotted as lines colored by recombination rate: the bluest line represents the individual with the least mean crossovers per cell and the reddest line represents the individual with the most mean crossovers per cell. Inter-individual differences remained when controlling for differential SNP coverage.
Figure 6:
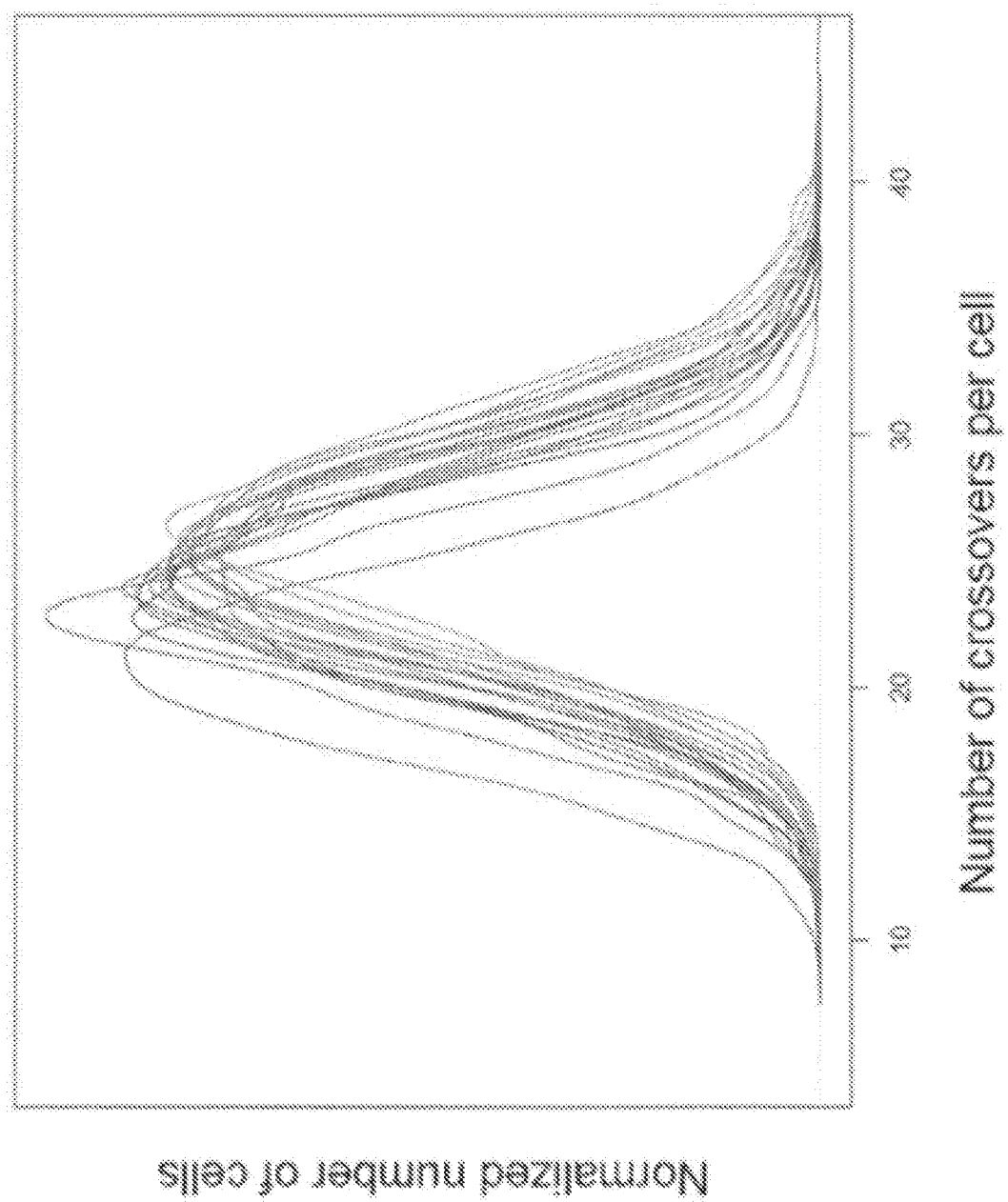
FIG. 6 shows that analysis of 851,678 crossover events identified using the instant "Sperm-seq" approach demonstrated that the total numbers of crossovers per sperm cell varied across the twenty donor individuals, even when controlling across individual donors for the total number of SNPs of each donor (which would have resulted in a differential ability to detect crossover events). When crossover events per cell results for each donor's cells were downsampled to include the same number of SNPs, variation similar to that shown in FIG. 5 still persisted, and again exhibited a Kruskal-Wallis $p<10^{-323}$.
Figure 11:
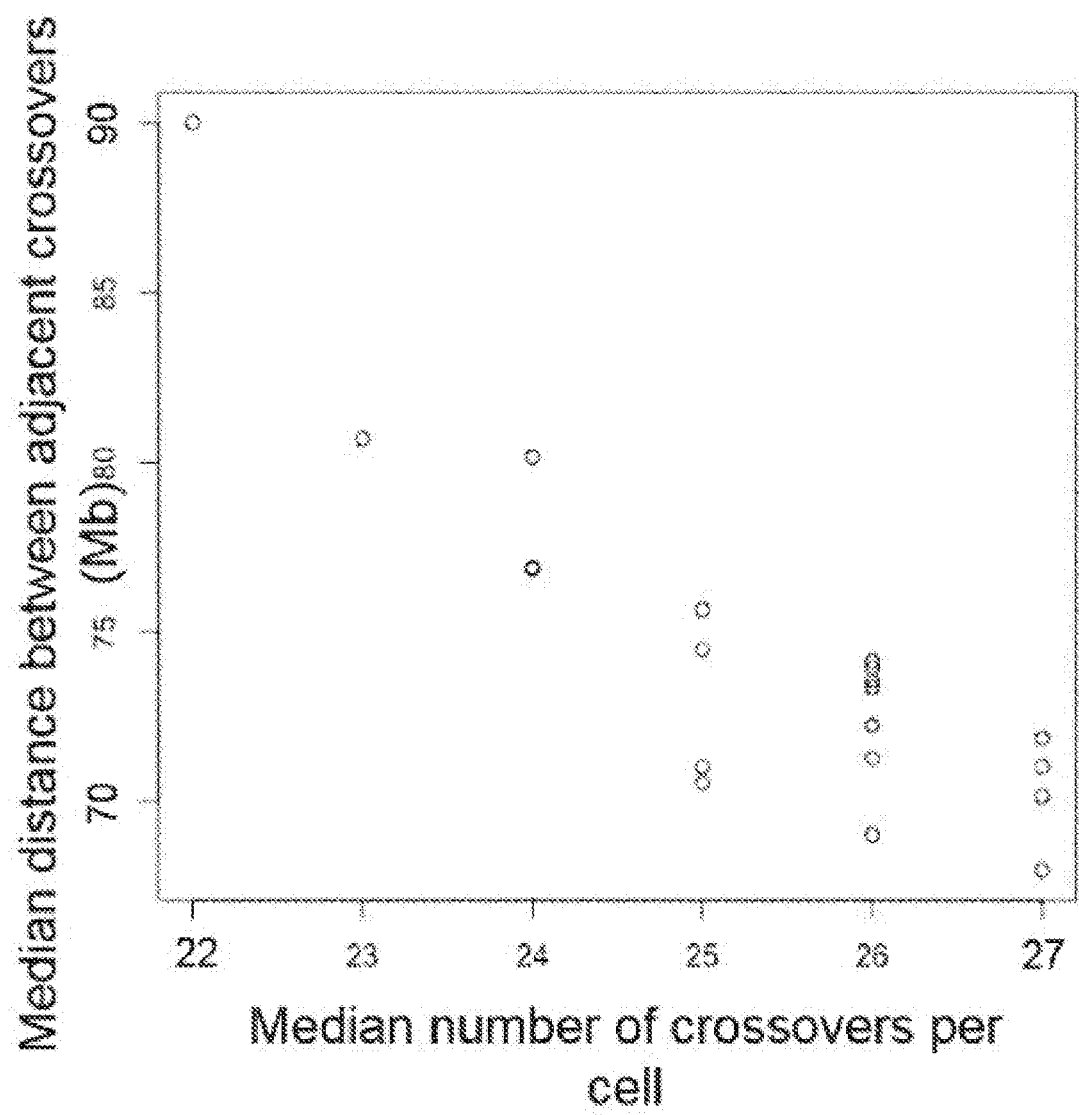
FIG. 11 shows that crossover interference was negatively correlated with recombination rate.

As exemplified above, high-throughput single-sperm sequencing has rendered newly visible the variability of meiotic processes within and among individuals, including number and placement of crossovers (FIGS. 5-7). The methods and compositions of the instant disclosure were used to quantify crossover interference in multiple individual germlines and observe differences in the patterns of crossover interference among individuals (FIGS. 10-12). The methods and compositions of the instant disclosure also have enabled discovery of aneuploidy events across all chromosomes and cells (FIGS. 17 and 18).

Analyses of the instant data have revealed new insights into meiosis. The methods and compositions of the instant disclosure also have enabled new investigations of male infertility. There are very few diagnostic tests for male partners of couples experiencing infertility beyond gross sperm count and motility. It is likely that there are genetic differences caused by abnormal meiosis in the sperm from male partners in idiopathic cases of infertility that can be diagnosed upon sequencing enough single sperm, and the instant disclosure has therefore provided a diagnostic technique that can be employed in examining male idiopathic infertility. For example, some embryos arrest development at the 8 cell stage, the first stage at which the paternal genetic contribution is required for development. Sperm from individuals with many such failures may have causal genetic defects discoverable via high-throughput single-sperm sequencing, i.e., via the approaches of the instant disclosure.

The methods and compositions of the instant disclosure also can be applied to genetic mapping and genome assembly in non-human species. For example, very large-scale genomic structural arrangements are made readily visible by single-sperm sequencing, enabling the creation of higher quality reference genomes.

All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

One skilled in the art would readily appreciate that the present disclosure is well adapted to carry out the objects and obtain the ends and advantages mentioned, as well as those inherent therein. The methods and compositions described herein as presently representative of preferred embodiments are exemplary and are not intended as limitations on the scope of the disclosure. Changes therein and other uses will occur to those skilled in the art, which are encompassed within the spirit of the disclosure, are defined by the scope of the claims.

In addition, where features or aspects of the disclosure are described in terms of Markush groups or other grouping of alternatives, those skilled in the art will recognize that the disclosure is also thereby described in terms of any individual member or subgroup of members of the Markush group or other group.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Embodiments of this disclosure are described herein, including the best mode known to the inventors for carrying out the disclosed invention. Variations of those embodiments may become apparent to those of ordinary skill in the art upon reading the foregoing description.

The disclosure illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present disclosure provides preferred embodiments, optional features, modification and variation of the concepts herein disclosed may be resorted to by those skilled in the art, and that such modifications and variations are considered to be within the scope of this disclosure as defined by the description and the appended claims.

It will be readily apparent to one skilled in the art that varying substitutions and modifications can be made to the invention disclosed herein without departing from the scope and spirit of the invention. Thus, such additional embodiments are within the scope of the present disclosure and the following claims. The present disclosure teaches one skilled in the art to test various combinations and/or substitutions of chemical modifications described herein toward generating conjugates possessing improved contrast, diagnostic and/or imaging activity. Therefore, the specific embodiments described herein are not limiting and one skilled in the art can readily appreciate that specific combinations of the modifications described herein can be tested without undue experimentation toward identifying conjugates possessing improved contrast, diagnostic and/or imaging activity.

The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context. Those skilled in the art will recognize, or be able to ascertain using no more than routine experimentation, many equivalents to the specific embodiments of the disclosure described herein. Such equivalents are intended to be encompassed by the following claims.

We claim:

1. A droplet comprising:
   i) a mammalian sperm cell nucleus of a mammalian sperm cell; and
   ii) a microbead comprising attached oligonucleotides, wherein the attached oligonucleotides comprise a nucleic acid sequence capable of hybridization and capture of genomic DNA and a microbead identification sequence that is common to all oligonucleotides attached to the microbead,
   wherein the mammalian sperm cell has been rapidly freeze-thawed and contacted with β-mercaptoethanol and heparin to make the mammalian sperm cell nucleus accessible to the microbead-attached oligonucleotides to an extent sufficient to allow for genomic DNA capture and amplification of genomic DNA to occur within the droplet.

2. The droplet of claim 1, wherein the sperm cell has been contacted with β-mercaptoethanol and heparin in an aqueous salt buffer, heated, then contacted with heparinase, thereby producing a sperm cell nucleus having genomic DNA that is accessible to the microbead-attached oligonucleotides.

3. The droplet of claim 1, wherein the microbead comprising attached oligonucleotides comprises at least 100 attached oligonucleotides, wherein the at least 100 attached oligonucleotides comprise a nucleic acid sequence capable of hybridization and capture of genomic DNA and a microbead identification sequence that is common to all at least 100 oligonucleotides on the microbead, optionally wherein the microbead-attached oligonucleotides are attached to the microbead via a cleavable linker, optionally via a photocleavable linker.

4. The droplet of claim 1, wherein the droplet is oil-encapsulated.

5. A droplet population comprising a plurality of droplets of claim 1.

6. The droplet population of claim 5, wherein a majority of the droplet population comprises droplets that individually comprise: i) a mammalian sperm cell nucleus; and ii) a microbead comprising attached oligonucleotides, wherein the attached oligonucleotides comprise a nucleic acid sequence capable of hybridization and capture of genomic DNA and a microbead identification sequence that is common to all oligonucleotides attached to the microbead, wherein the mammalian sperm cell nucleus is accessible to the microbead-attached oligonucleotides to an extent sufficient to allow for genomic DNA capture and amplification of genomic DNA to occur within the droplet.

7. The droplet population of claim 5, wherein each microbead comprises at least 100 attached oligonucleotides having a microbead identification sequence that is common to all at least 100 oligonucleotides on each microbead, wherein the microbead identification sequence that is common to all at least 100 oligonucleotides on each microbead is either a microbead identification sequence that is unique to each microbead within each droplet of the droplet population or is a microbead identification sequence that is a member of a population of microbead identification sequences that is sufficiently degenerate to the population of microbeads within the droplet population that a majority of microbeads within the droplet population each possesses a unique microbead identification sequence.

8. The droplet of claim 1, wherein the nucleic acid sequence capable of hybridization and capture of genomic DNA is a random sequence.

9. The droplet of claim 1, wherein the droplet further comprises reagents for performing mammalian genomic DNA amplification and is subjected to a slow-ramping amplification process to perform said amplification of genomic DNA.

10. The droplet of claim 1, wherein the mammalian sperm cell is a human sperm cell.

11. The droplet of claim 1, wherein the microbead is of 1-100 μm in diameter, optionally wherein the microbeads are 10 μm in diameter.

12. A method for making a droplet comprising a mammalian sperm cell nucleus and a microbead comprising attached oligonucleotides comprising:
   i) obtaining a mammalian sperm cell;
   ii) freeze-thawing the mammalian sperm cell;
   iii) contacting the mammalian sperm cell with β-mercaptoethanol and heparin in an aqueous salt buffer and applying heat;
   iv) contacting the mammalian sperm cell with heparinase in an amount sufficient to inactivate heparin,
   wherein steps (i)-(iv) thereby produce a mammalian sperm cell nucleus having genomic DNA that is accessible to microbead-attached oligonucleotides, and
   v) combining within a droplet the mammalian sperm cell nucleus and a microbead comprising attached oligonucleotides,
   thereby making a droplet comprising a mammalian sperm cell nucleus and a microbead comprising attached oligonucleotides.

13. The method of claim 12, wherein the oligonucleotides of the microbead comprising attached oligonucleotides comprise a nucleic acid sequence capable of hybridization and capture of genomic DNA and a microbead identification sequence that is common to all oligonucleotides attached to the microbead, optionally wherein the microbead-attached oligonucleotides are attached to the microbead via a cleavable linker, optionally via a photocleavable linker and/or optionally wherein the nucleic acid sequence capable of hybridization and capture of genomic DNA is a random sequence.

14. The method of claim 12, wherein the droplet comprises a single mammalian sperm cell nucleus and a single microbead comprising attached oligonucleotides.

15. The method of claim 12, wherein:
   the droplet further comprises reagents for mammalian genomic DNA amplification;
   the droplet is subjected to an amplification process to perform amplification of genomic DNA, optionally wherein the amplification process is a slow-ramping amplification process;
   the mammalian sperm cell nucleus genomic DNA is subjected to a next-generation sequencing technique, optionally wherein the mammalian sperm cell nucleus genomic DNA is sequenced to at least 1% genomic coverage, optionally wherein the next-generation sequencing technique is selected from the group consisting of solid-phase, reversible dye-terminator sequencing; massively parallel signature sequencing; pyro-sequencing; sequencing-by-ligation; ion semiconductor sequencing; Nanopore sequencing and DNA nanoball sequencing, optionally wherein the next-generation sequencing technique is solid-phase, reversible dye-terminator sequencing, optionally wherein the next-generation sequencing reveals the presence of aneuploidy and/or crossover patterns in the mammalian sperm cell, optionally wherein the next-generation sequencing reveals the presence of aneuploidy in the sperm cell of a male partner of an infertile couple, optionally wherein aneuploidy is detected in a chromosome other than chromosomes 21, 18 and 13;

the microbead comprising attached oligonucleotides comprises at least 100 attached oligonucleotides, wherein the at least 100 attached oligonucleotides comprise a nucleic acid sequence capable of hybridization and capture of genomic DNA and a microbead identification sequence that is common to all at least 100 oligonucleotides on the microbead;

the droplet is oil-encapsulated;

the mammalian sperm cell is a human sperm cell; and/or the microbead is of 1-100 µm in diameter, optionally wherein the microbeads are 10 µm in diameter.

16. A kit for obtaining sperm genomic DNA sequence comprising:
i) β-mercaptoethanol, heparin and heparinase; and
ii) a population of microbeads comprising attached oligonucleotides, wherein the attached oligonucleotides comprise a nucleic acid sequence capable of hybridization and capture of sperm genomic DNA and a microbead identification sequence that is common to all oligonucleotides attached to each individual microbead of the population of microbeads, and instructions for its use.

17. The kit of claim 16:
further comprising reagents for mammalian genomic DNA amplification; and/or
further comprising reagents for next-generation sequencing, optionally wherein the next-generation sequencing technique is selected from the group consisting of solid-phase, reversible dye-terminator sequencing; massively parallel signature sequencing; pyro-sequencing; sequencing-by-ligation; ion semiconductor sequencing; Nanopore sequencing and DNA nanoball sequencing, optionally wherein the next-generation sequencing technique is solid-phase, reversible dye-terminator sequencing.

18. The kit of claim 16, wherein:
each microbead of the population of microbeads comprising attached oligonucleotides comprises at least 100 attached oligonucleotides, wherein the at least 100 attached oligonucleotides comprise a nucleic acid sequence capable of hybridization and capture of genomic DNA and a microbead identification sequence that is common to all at least 100 oligonucleotides on the microbead, optionally wherein the microbead identification sequence that is common to all at least 100 oligonucleotides on each microbead is either a microbead identification sequence that is unique to each microbead within the population of microbeads or is a microbead identification sequence that is a member of a population of microbead identification sequences that is sufficiently degenerate to the population of microbeads that a majority of microbeads within the population of microbeads each possesses a unique microbead identification sequence, optionally wherein the microbead-attached oligonucleotides are attached to the microbead via a cleavable linker, optionally via a photocleavable linker;

the nucleic acid sequence capable of hybridization and capture of genomic DNA is a random sequence; and/or each microbead of the population of microbeads is of 1-100 µm in diameter, optionally wherein each microbead is approximately 10 µm in diameter.

* * * * *

SEQUENCE LISTING

```
<160> NUMBER OF SEQ ID NOS: 9

<210> SEQ ID NO 1
<211> LENGTH: 14
<212> TYPE: DNA
<213> ORGANISM: Artificial
<220> FEATURE:
<223> OTHER INFORMATION: Synthetic

<400> SEQUENCE: 1
gttacgcaat cgct                                                      14

<210> SEQ ID NO 2
<211> LENGTH: 14
<212> TYPE: DNA
<213> ORGANISM: Artificial
<220> FEATURE:
<223> OTHER INFORMATION: Synthetic

<400> SEQUENCE: 2
acgactagtc aagt                                                      14

<210> SEQ ID NO 3
<211> LENGTH: 14
<212> TYPE: DNA
<213> ORGANISM: Artificial
<220> FEATURE:
<223> OTHER INFORMATION: Synthetic

<400> SEQUENCE: 3
ttagcggaaa gttg                                                      14
```

```
<210> SEQ ID NO 4
<211> LENGTH: 14
<212> TYPE: DNA
<213> ORGANISM: Artificial
<220> FEATURE:
<223> OTHER INFORMATION: Synthetic

<400> SEQUENCE: 4
agtgtctcgt agtc                                                           14

<210> SEQ ID NO 5
<211> LENGTH: 14
<212> TYPE: DNA
<213> ORGANISM: Artificial
<220> FEATURE:
<223> OTHER INFORMATION: Synthetic

<400> SEQUENCE: 5
caactggtaa tccc                                                           14

<210> SEQ ID NO 6
<211> LENGTH: 14
<212> TYPE: DNA
<213> ORGANISM: Artificial
<220> FEATURE:
<223> OTHER INFORMATION: Synthetic

<400> SEQUENCE: 6
atgccatccg tggc                                                           14

<210> SEQ ID NO 7
<211> LENGTH: 14
<212> TYPE: DNA
<213> ORGANISM: Artificial
<220> FEATURE:
<223> OTHER INFORMATION: Synthetic

<400> SEQUENCE: 7
atctcttcag ccta                                                           14

<210> SEQ ID NO 8
<211> LENGTH: 27
<212> TYPE: DNA
<213> ORGANISM: Artificial
<220> FEATURE:
<223> OTHER INFORMATION: Synthetic

<400> SEQUENCE: 8
gtgagtgatg gttgaggtag tgtggag                                             27

<210> SEQ ID NO 9
<211> LENGTH: 44
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (28)..(41)
<223> OTHER INFORMATION: n is a, c, g, or t

<400> SEQUENCE: 9
gtgagtgatg gttgaggtag tgtggagnnn nnnnnnnnn nkkk                           44
```